United States Patent [19]

Beasley et al.

[11] Patent Number: 4,827,423

[45] Date of Patent: May 2, 1989

[54] COMPUTER INTEGRATED MANUFACTURING SYSTEM

[75] Inventors: Thomas B. Beasley, Pilot Mountain; Thomas W. Cearley, Clemmons; David A. Chandler; Kim A. Gondring, both of Winston-Salem; Richard A. Guarino; William G. Hutchins, both of Pfafftown; Marvin R. Martin, Winston-Salem; Eugene E. Norris, Winston-Salem; Lloyd T. Prout, Winston-Salem; Jeffrey R. Schlottman, Winston-Salem; Charlotte M. Smith, Winston-Salem; William F. Summers, Mocksville; David C. Twine, Winston-Salem; R. Victor Walsh, Winston-Salem, all of N.C.

[73] Assignee: R. J. Reynolds Tobacco Company, Winston-Salem, N.C.

[21] Appl. No.: 53,909

[22] Filed: May 26, 1987

Related U.S. Application Data

[63] Continuation-in-part of Ser. No. 5,172, Jan. 20, 1987.

[51] Int. Cl.$^4$ .................. G06F 15/46; G06F 15/16
[52] U.S. Cl. ................................ 364/468; 364/131; 364/200

[58] Field of Search ............... 364/468, 478, 131–135, 364/474, 475, 481, 402, 403, 200 MS File, 900 MS File

[56] References Cited

U.S. PATENT DOCUMENTS

| | | | |
|---|---|---|---|
| 4,237,598 | 12/1980 | Williamson | 364/474 X |
| 4,383,298 | 5/1983 | Huff | 364/200 X |
| 4,698,766 | 10/1987 | Entwistle | 364/132 X |
| 4,714,995 | 12/1987 | Materna et al. | 364/200 |

Primary Examiner—Joseph Ruggiero
Attorney, Agent, or Firm—Foley & Lardner, Schwartz, Jeffery, Schwaab, Mack, Blumenthal & Evans

[57] ABSTRACT

The Computer Integrated Manufacturing System includes a plurality of levels of computer control which organize and disseminate the information for controlling shop floor level systems. Both scheduling data and data relating to process, product, and material specifications as well as bills of material are generated in an upper level computer system and refined and down loaded as needed to lower level computers controlling the shop floor processes. The computers on the upper levels are capable of communication with the computers on the lower levels and computers on the same level are capable of communication with each other as needed to pass information back and forth.

44 Claims, 14 Drawing Sheets

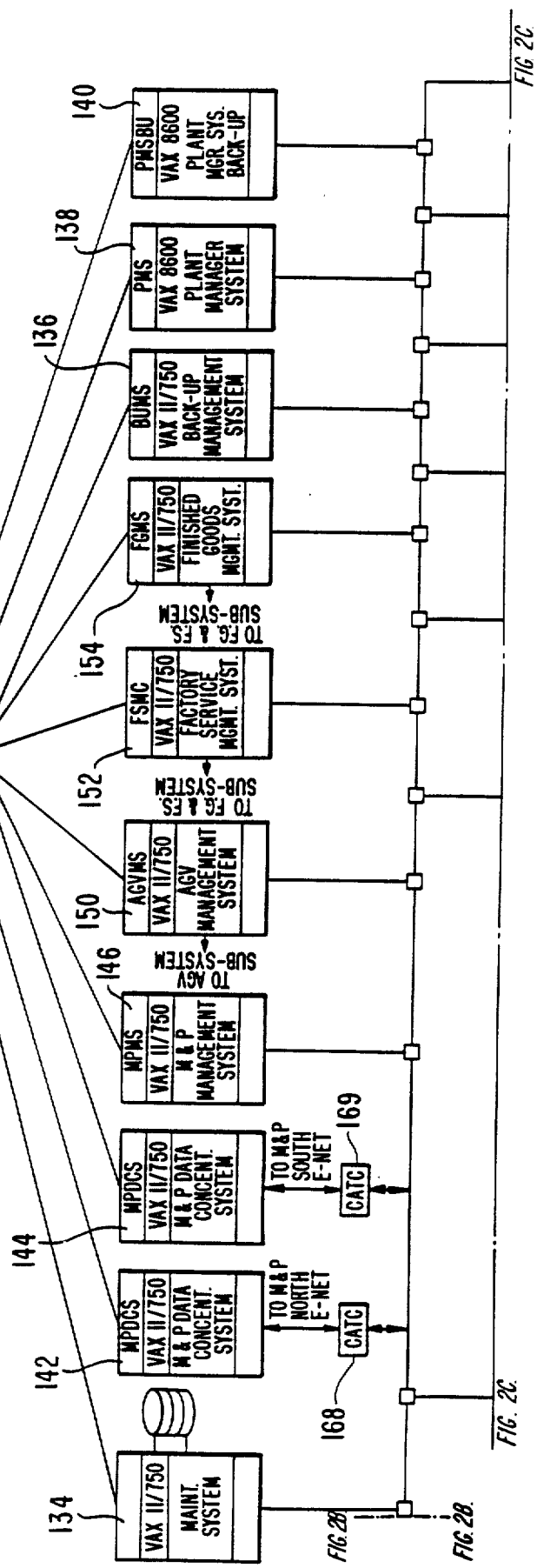
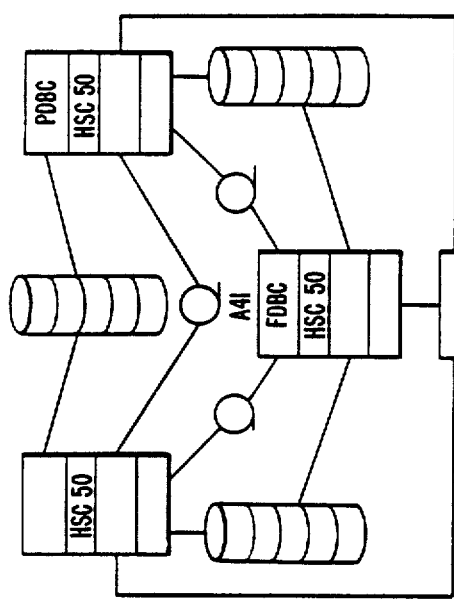
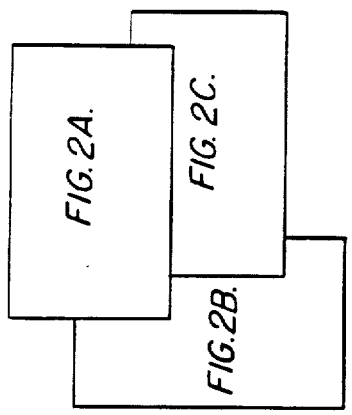
FIG. 2A.

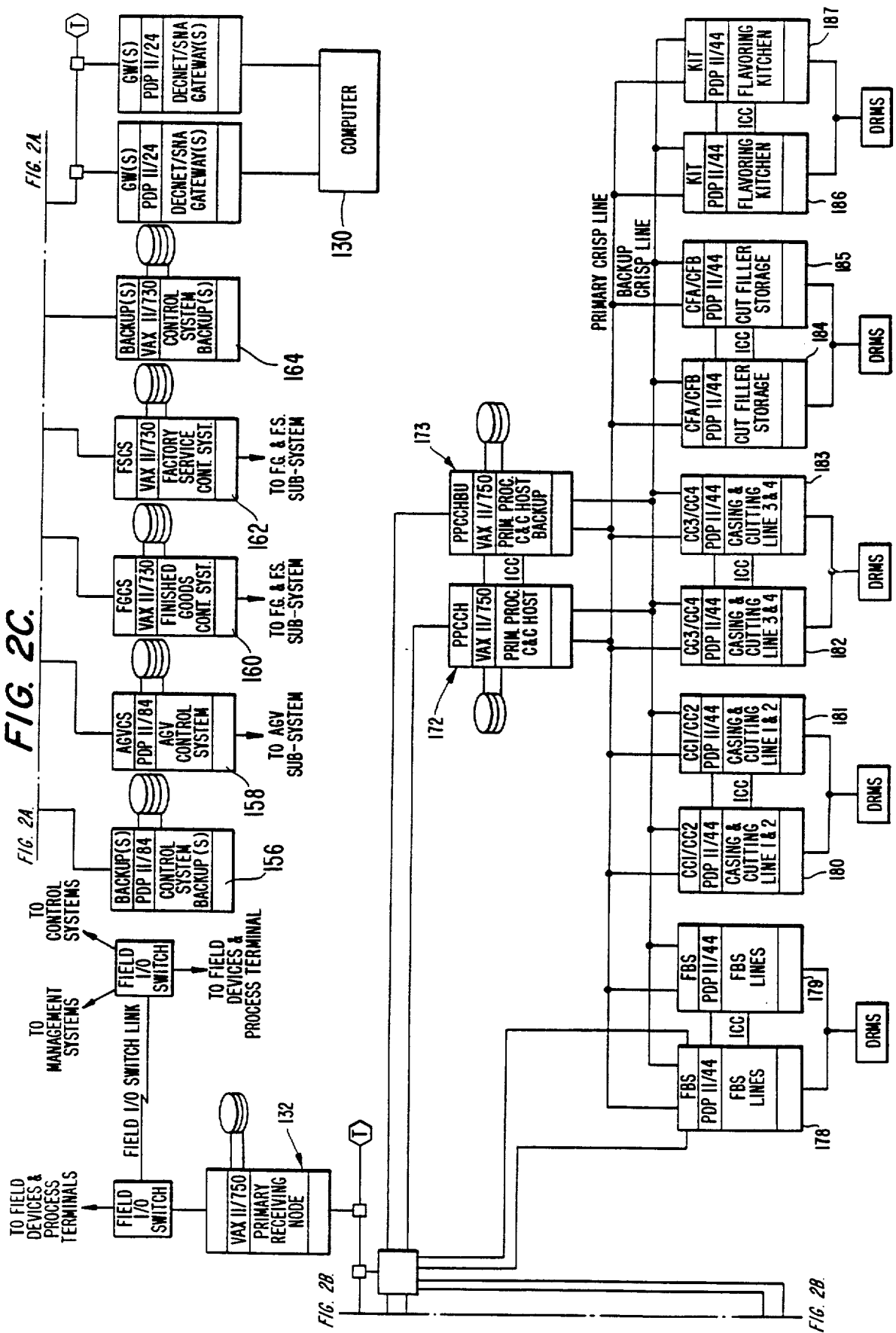

MANUFACTURING STANDARDS SYSTEM DATA STRUCTURE

FINISHED CASE ITEM ID + VERSION

FIG. 10.
CONFIGURATION MATRIX

| ITEM ID \ DATE (SHIFT) | JAN 10 (1) | JAN 10 (2) | JAN 1 (3) | JAN 10 (4) | JAN 11 (1) | JAN 11 (2) |
|---|---|---|---|---|---|---|
| 6924044 | VERSION 1 | 1 | 1 | 2 | 2 | 2 |
| 6924056 | VERSION | 2 | 2 | 2 | 2 | 2 |

PRODUCTION PLANNING FUNCTIONS

COMPUTER INTEGRATED MANUFACTURING SYSTEM

BACKGROUND OF THE INVENTION

Cross Reference To Related Application

This is a continuation-in-part of application Ser. No. 005,172, filed Jan. 20, 1987.

FIELD OF THE INVENTION

This invention relates to computerized control of manufacturing facilities and especially to control systems known as computer integrated manufacturing facilities in which an integrated computerized control is established from the management level through the shop floor level.

DISCUSSION OF RELATED ART

Computerized control systems have been known and widely used for a long time. In the manufacturing environment, these systems have generally been used in isolated areas to control a single machine or a single group of machines for producing a product, or used to control a line of machines in a process control. In addition, computer systems are commonly used to assist company accounting departments, sales departments, research and development departments and the like. Recently, it has been suggested that a hierarchy of control be established to integrate the various individual computer systems found in a plant. Such integration, however, has proved to be difficult and, while much has been written about the desirability of such a fully automated system, little has actually been accomplished to bring about an actual fully computerized integrated manufacturing facility.

SUMMARY OF THE INVENTION

One object of the present invention is to provide a computer integrated manufacturing facility.

Another object of the present invention is to provide a computer integrated manufacturing facility in which a novel manufacturing specifications system is used to define and disseminate bill of materials information as well as process control specifications.

A further object of the present invention is to provide a computer integrated manufacturing system in which scheduling information is combined with the bill of material and process control data to provide precise control data for manufacturing stations on the shop floor.

Another object of the present invention is to provide a computer integrated manufacturing system in which individual management centers are established to control various functions in the plant and the individual management centers are interconnected so that they can communicate with each other.

An additional object of the present invention is to provide a computer integrated manufacturing system in which changes in specifications and process control data can be made easily, can be verified and can be disseminated to the shop floor in a timely manner according to a predetermined implementation schedule.

Yet another object of the present invention is to provide a computer integrated manufacturing system in which a plurality of levels of computers are established with communication between computers on each level as well as communication between computers on adjacent levels.

An additional object of the present invention is to provide a computer integrated manufacturing system which implements just-in-time concepts for both machine scheduling and material ordering.

In accordance with the above and other objects, the present invention is a multilevel computerized control system, comprising a first level computer system having at least one first computer for controlling a plurality of individual processes for producing a plurality of different products. The first level computer system comprises a plurality of sensor inputs for receiving process monitoring sensor signals from sensors at respective process stations, a plurality of control outputs for providing control signals for processes to be controlled, storage for storing process control parameters for processes to being carried out, storage for storing bill of materials records containing indications of materials necessary for products being produced, storage for storing values of the sensor signals, and programs for producing the control signals to control the processes as a function of the sensor signal values and the process control parameters for processes being carried out. A second level computer system is also included. The second level computer system comprises at least one second computer connected to the first level computer system for storing a database having a plurality of files containing process control parameters associated with different processes which may be required to be performed by the first level computer system to produce different products. The files include a process specification file containing records indicating process control parameters necessary for producing the different products and a bill of materials file containing records indicating materials necessary for producing the different products. The second level computer system is connected to receive scheduling information indicative of scheduled process controls to be carried out by the first level computer system to produce scheduled products, is programmed to provide selected ones of the control parameters necessary to carry out the scheduled process controls to the first level computer system as the contrl parameters for processes being carried out and to provide selected records from the bill of materials file indicating materials necessary for producing the scheduled products as the materials for products being produced, and is programmed to receive indications of the values of the sensor signals. Finally, a third level computer system is included. The third level computer system is connected to the second level computer system and is programmed to generate the database and transmit the database to the second level computer system. The third level computer system is also connected to receive modification instructions for modifying records of the database. The modification instructions are contained in a modification instruction file containing information for modifying the records and information as to times at which modifications to the records are to be implemented.

In accordance with other aspects of the invention, the second level computer system includes monitor drivers for displaying the values of the sensor signals on operator console monitors.

Furthermore, the database may include a product specification file having records with data related to specifications of a product to be produced, a bill of materials file continuing a list of materials needed to produce a product, an item master file containing records having purchasing data, and accounting data related to products produced and materials purchased, and a revision control file containing information on revisions to any other file.

An automated material delivery system may be included for providing material to the process stations, and a further second level computer system may be provided for controlling operation of the automated material delivery system in response to commands for materials received from the processing stations.

Each first level computer system may comprise a lower level of computers having a plurality of identical computers programmed to carry out specific process functions, and a higher level computer connected to other first level computer systems in a communication network. The higher level computer is connected to the lower level computers and is programmed to receive process control parameters from the second level computer system required for the lower level computers to carry out their specific process functions, transmit the received process control parameters to the respective lower lever computers as required for the lower level computers to carry out their programmed specific process functions, receive sensor signal values from the respective lower level computers and transmit the received sensor signal values to the second level computer system.

The second level computer system may comprise a superior level computer and an inferior level of computers. The inferior level of computers comprises a plurality of identical computers connected together in a communication network and is connected to a respective plurality of higher level computers of the first level computer network. The inferior level of computers is programmed to display the received sensor signal values on display consoles, and receive from the superior level computer and store respective portions of the database required for the lower level computers to carry out their specific process functions.

The scheduling information may comprise a production schedule covering a first production period which comprises a first time period. The first production schedule is received by the superior level computer and the superior level computer provides scheduling information to the inferior level computers which covers a shorter period of time and the superior level computer provides the respective portions of the database to the inferior level computers which contain process parameters required over the shorter period of time to meet the production schedule.

The invention also includes a manufacturing control system comprising a computer database system for storing information relating to products to be manufactured and processes for manufacturing the products as well as information relating to changes in the products and processes. The database system includes a product file containing detail specification records for finished and intermediate products, a process file containing records with process parameters and instructions for machines or groups of machines used for producing the products in the product file, a material file containing records with detail specification data for purchased materials, and a change order file containing information relating to proposed changes in records of the other files. The change order file contains records indicating the type of change, change approval information and the effective date of the change.

The invention also includes the method of controlling the computer integrated manufacturing system and the method of manipulating the database.

BRIEF DESCRIPTION OF THE DRAWINGS

The above and other objects of the present invention will become more readily apparent when the invention becomes more fully understood from the detailed description set forth below, reference being had to the accompanying drawings in which like reference numerals represent like parts throughout and in which:

FIGS. 2a, 2b, 2c and 2d show an overview of the computer architecture used in the computer integrated manufacturing system of the present invention.

FIG. 7. shows the relationship of the change order file and the revision file to the other files of the manufacturing standards system.

FIG. 10. shows the structure of the configuration matrix of the factory manufacturing standards system of the present invention.

DETAILED DESCRIPTION OF THE PREFERRED EMBODIMENTS

The present invention will now be described in relation to a cigarette manufacturing facility, it being understood that the principles and concepts described herein are also application to other types of manufacturing plants.

Figure 1:
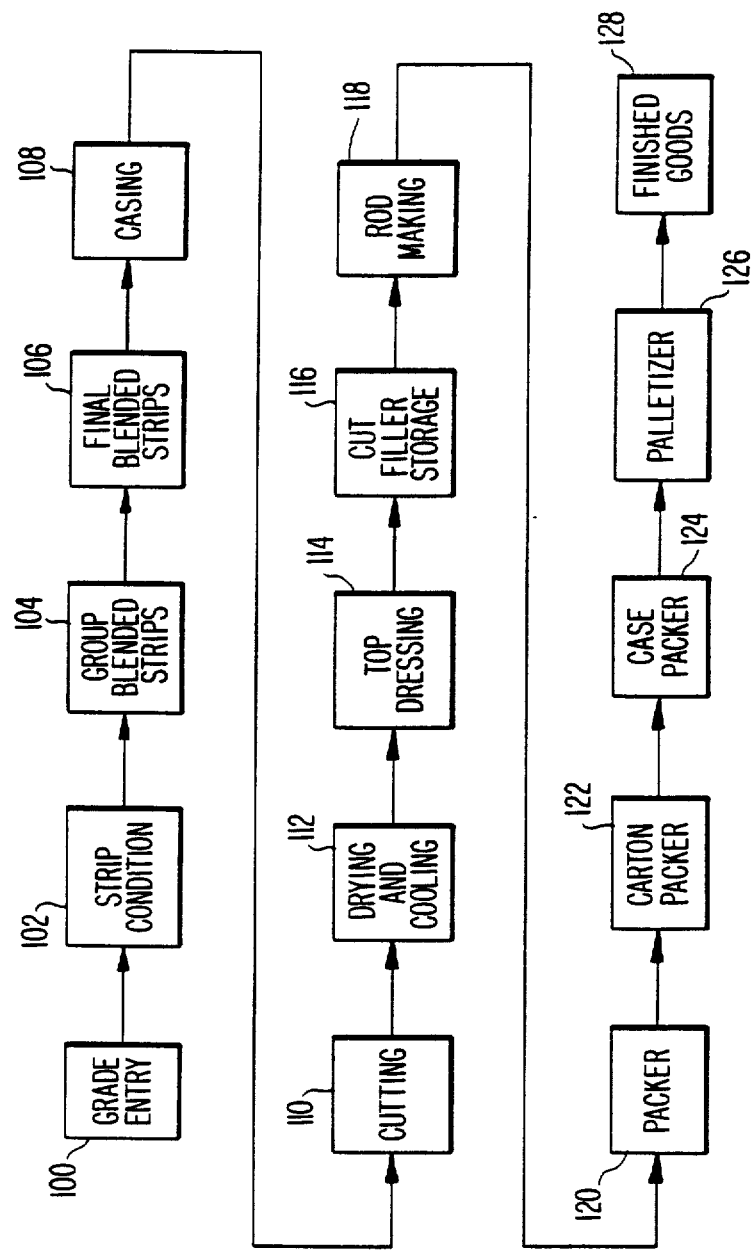
FIG. 1. shows an overview of a plant to be controlled by the computer integrated manufacturing system of the present invention.

In order to understand the concepts of the present invention, it is helpful to understand the major functions to be performed in the manufacture of a cigarette. FIG. 1 shows a block diagram flow chart of the operations to be performed in the manufacture of a cigarette.

First, tobacco is received at the grade entry area 100. Here, grded tobacco in bales is pulled according to a pull list which is displayed on a monitor according to a stored recipe. The tobacco has been previously marked with a bar code indicating the grade of the bale. As is well known, tobacco is graded according to grade, belt, and crop year. The actual grading of the tobacco is not the subject of the present invention and will not be discussed in detail here. In general there are two types of tobacco processed. These are Turkish tobacco and domestic tobacco. These two types may require different subsequent processing and therefore may be received at different grade entry areas 100.

The bar code on the bale is read and automatically compared with a grade code stored in the recipe file indicating the grade of tobacco required. If the received bale is acceptable, it is sliced into smaller sections which are weighed so as to in feed the appropriate amount required by the recipe, preconditioned to provide an appropriate amount of moisture for subsequent delamination, and then passed to the strip condition area 102.

In strip condition area 102, the slices are delaminated in a delaminating feeder which passes the tobacco to a conditioning drum. The conditioning drum increases the temperature and the moisture level of the tobacco to be within a predetermined range. After leaving the conditioning drum, the tobacco flow is divided into two equal parallel lines. Each of these lines has a separator in which the lighter, loosened lamina is separated from the heavier, unloosened leaf by an ascending air stream. Moreover, dirt particles are separated from the lighter lamina. The heavier lamina is exposed to another conditioning process in a steam flotation chamber. This results in an additional loosening up of the tobacco.

Grade entry area 100 together with strip condition area form the receiving and blending (R&B) zone. There may be a plurality of R&B lines depending on the total amount of tobacco to be processed.

From the R&B zone the conditioned tobacco is fed to the group blended strips area 104 (GBS zone). The GBS zone comprises three infeed lines which feed 20 bins arranged in two groups of five bin pairs. The bins of the GBS zone provide intermediate storage for various tobacco blends, which are not yet final blends according to the stored recipe. The various R&B zones communicate by conveyors to the three infeed lines of the GBS zone in order to fill the GBS bins. The various bin pairs are assigned to different types of blends. For example, four of the bin pairs may contain a Burley tobacco blend, three of the bin pairs may contain a Flue Cured tobacco blend, one bin pair may contain a Maryland tobacco blend, one bin pair may contain a Turkish tobacco blend, etc.

Each bin pair of the GBS zone is connected by conveyor to feed either one of two infeed lines to the final blended strips area 106 (FBS zone). The FBS zone comprises four bin pairs which are fed with tobacco from the bin pairs of the GBS zone according to a recipe. That is, the tobacco being stored in the intermediate storage of the FBS zone is moved upon demand to the FBS zone in controlled quantities so that a final blend is obtained in each of the FBS zone bin pairs.

The final blended tobacco is passed from one of the bin pairs of the FBS zone according to the recipe to the casing area 108. The casing area comprises a casing drum into which steam, moisture and casing are provided. After being cased, the tobacco is passed to the cutting area 110 where it is cut to the proper size for the tobacco product being produced, according to the recipe. The cut tobacco is then dried and cooled in the drying and cooling area 112 and then passed to the top dressing area 114. The casing area 108, cutting area 110, drying and cooling area 112 and top dressing area 114 form the cutting and casing zone (C&C) of the process.

Further details of the C&C zone are set forth in copending application Ser. No. 865,483, filed May 20, 1986, abandoned, and assigned to the assignee of the present invention, the disclosure of which is incorporated herein by reference thereto.

The portion of the system made up by the R&B, GBS, FBS and C&C constitutes the primary processing portion of the cigarette manufacturing process.

From the C&C zone, the tobacco is transported to the cut filler storage area 116. This area comprises a plurality of bins for storing the cut filler until it is needed for the final cigarette making step.

When needed, the cut filler is transported via conveyor to the rod making area 118 where the cigarette rods are formed. After formation of the rods, the rods are packed together usually 20 to a pack in the packing area 120. The packs of cigarettes are then packed into a carton in the carton packing area 122. The cartons of cigarettes are then packed into a case in the case packing area 124. The cases are then assembled together on pallets in the pelletizing area 126. One rod making machine, one packer, one carton packer, one case packer and one palletizer are assembled into a single making and packing (M&P) complex. A single plant may contain 72 or more such complexes. The M&P complexes are fed from bins which are themselves fed from the FBS bins. The M&P bins are connected such that three bins feed six complexes. This provides sufficient flexibility for the simultaneous manufacture of a plurality of cigareete brands even if one or more of the complexes become disabled.

Finally, the palletized product is moved to the finished goods area 128 for storage or shipment for sale.

As will be discussed in further detail below, a plant also may include an automatic guided vehicle (AGV) system comprising a plurality of guided vehicles which operate under computer control to bring materials to the M&P complexes when needed and to transport finished product to the finished goods area when the cases have been palletized. The plant also includes an automated materials storage and retrieval system known as a factory service system (FSS) which takes the form of a computerized warehouse for storing and retrieving the materials to be delivered to the M&P complexes by the AGV system.

The foregoing provides an overview of the cigarette making process controlled by the present invention. In general this comprises primary processing, making and packing and finished goods. It should be understood that the foregoing describes the activities of a single plant. However, a plurality of plants may be operating at the same time. It is also possible that some of the activities discussed above may be carried out at a first plant and some of the activities may be carried out at a second plant with the product of the first plant being shipped to the second plant for further processing. All of these possibilities are contemplated by the present invention.

COMPUTER ARCHITECTURE

FIG. 2 shows the general architecture of the computer system used in the present invention. The system includes a mainframe computer system 130 located at corporate headquarters. This computer system is referred to as the level IV system and is used to generate the material specifications, product specifications, and process specifications which are eventually used to produce product art the shop floor. The level IV system could be any mainframe but in this particular instance is shown to be an IBM computer system.

It should be noted that the term "material" is used hereafter to refer to a material which is purchased for use in manufacturing a product. A "product" is something which is manufactured even if the "product" is only used for the manufacture of another product. Accordingly, as will be discussed in more detail below, both materials and products are used in the manufacture of other products.

The level IV computer system 130 may be connected to a plurality of plants. A single plant is shown in FIG. 2 to comprise a level III computer system made up of Digital Equipment Corporation (DEC) VAX 11/750 computers 132 and 134 as well as DEC VAX 8600 computers 136, 138 and 140. The level IV system is shown to communicate to the level III system through one or more DECnet/SNA gateways at 56 KB. This communication link is served by one or more DEC PDP 11/24 computers.

The computers of the level III system communicate to each other through an ETHERNET communication link. This is a conventional collision detection type communication link provided by DEC. It is not essential that the computers of the level III system be from the same manufacturer. However, it is imperative that they be capable of communication with each other. Accordingly, by having the computers originate from the same vendor, the communication between computers is easily achieved by using vendor supplied systems.

The level III systems perform functions to be discussed below. These functions may be assigned to individual computers or several functions may be performed by a single computer. For example, as shown in FIG. 2, computer 132 performs all primary processing management functions, computer 134 performs maintenance functions, computer 138 performs plant management system functions, computer 136 performs back-up management systems functions and computer 140 acts as a plant management system back-up computer.

Below the level III system there is a level II system. As shown in FIG. 2, the level II system comprises VAX 11/750 computers 142, 144, 146, 150, 152, 154, and 170-173. These computers are from a single vendor to facilitate communication between systems which is essential for a computer integrated system to operate properly. Computers 142 and 144 are assigned the task of data concentration. Each of these computers is connected to receive data signals from 36 M&P complexes. The data signals from the 36 M&P complexes are routed to a common disc storage area 166 by each computer 142, 144.

It should be understood that the division of functions between computers on Level II is based on the processing capacity of the computers. It is not necessary that separate VAX 11/750 computers be used for the Making and Packing Management System and the Factory Service Management, as shown in FIG. 2a, if one computer can handle all of the processing needs of both systems. Also, the use of VAX 11/750 computers is optional. Computers having greater computing power can be substituted for the VAX 11/750 computers. For example, VAX 8600 computers are now available and can be used in place of the VAX 11/750 computers.

The disc storage area 166 may be accessed by the level III and level II computers as shown in FIG. 2 in order to pass data between these systems as necessary, as will become more apparent below.

Several of the level II computers act as management systems for the manufacturing processes. Computer 146 is the M&P management system and is programmed to pass data on to the M&P complexes on the shop floor, as will be discussed below. Computer 152 is the factory service management system (FSM). This computer receives requests from the M&P management system (MPMS) for specific materials such as case blanks, cigarette paper etc to be used in the M&P complexes and sends instructions to computer 162 which forms the factory service contrl system. The factory service control system (FSCS) controls the automated warehouse and automatically stores and retrieves materials in response to the instructions from the FSM system. Further, the FSM system sends requests to computer 150 which forms the automatic guided vehicle management system (AGVMS) for an automatic guided vehicle to deliver the retrieved goods to the requesting M&P complex.

Computer 150 receives requests from the FSM system for guided vehicles to deliver materials to an M&P complex or receives requests directly from the M&P management system to carry palletized goods to the finished goods area. The AGV management system sends instructions to the AGV control system in computer 158. The AGV control system carries out the instructions by causing a series of guided vehicles to deliver materials to the various M&P complexes upon request, or transport products to the finished goods area upon request. The AGV management system keeps track of the progress of the guided vehicles and reports back to the M&P management system when a request to deliver goods to a specific M&P complex has been met, and also keeps track of finished goods being transported to the finished goods area and instructs the finished goods management system of the identity of the goods if such a request is made.

The finished goods management system (FGMS) resides in computer 154 and sends instructions to the finished goods control system resident in computer 160. The finished goods control system operates a series of conveyors which transport the finished goods to a series of loading docks for loading onto vehicles for transportation to various locations and controls several elevators for moving the finished goods to storage locations, if necessary. The finished goods control system also checks the cases for proper seal and informs the finished goods management system of any defects. The finished goods management system determines the dock onto which the cases should be loaded and determines which cases are to be temporarily stored based on the state of the loading docks and the defects in the cases reported by the finished goods control system.

Computers 156 and 164 act as control system back-up computers and can take over the responsibilities of the control system computers if the need should arise due to failure of one of the control system computers.

There is a level I computer system below the level II system. The level I system comprises computers 156, 158, 160, 162 and 164, discussed above, and a single computer at each M&P complex, which may be a PDP 11/83 computer. Each of these M&P computers is referred to as a computer at the complex (CATC). One such CATC 168, 169 is shown connected to each data concentrator system 142, 144. However, there are actually 36 such CATCs connected to each data concentrator, as discussed above. Each CATC communicates with a data concentrator through the ethernet communication link and to the MPMS through the data concentrator. The transmission of production data or the like is carried out by the data concentrator accessing the common storage area 166 to store or receive data. Communication of requests or the like is referred to as a transaction and is carried out by the data concentrator communicating directly with the MPMS through the MPMS.

Every 15 seconds the CATC receives information in the form of production data and the like from the complex. This information is stored in the CATC and every5 minutes the CATC sends data to the data concentrator for storage in the disc storage area 166.

As discussed above, the level II system includes primary processing host computers 170 and 172. Each host computer has a backup computer available to take over operation in the even of a failure. Host backup computer 171 backs up computer 170 and host backup computer 173 backs up host computer 172.

Host computer 170 together with backup computer 171 control the receiving and blending portion of primary processing through a pair of redundant node computers 174, 175 and 176, 177, which are level I computers. Computers 174 and 176 are primary control computers and computers 175 and 177 back up the primary computers 174 and 176. Computers 174 and 175 control the grade entry functions through the infeed to the GBS bins. Computers 176 and 177 control the outfeed of the GBS bins.

Similarly, host computers 172 and 173 control the primary processing functions from the outfeed of the FBS bins to the infeed to the cut filler storage. Additionally, these computers control the flavoring kitchen in which the flavorings such as the top dressing and the casing are prepared. Host computers 172 and 173 operate through level I node computers 178–187 which are connected as primary control computers 178, 180, 182, 184, and 186, and backup computers 181, 183, 185, and 187. Computers 178 and 179 control the outfeed of the FBS bins, computers 180 and 181 control four cutting and casing lines, computers 184 and 185 control the infeed to the cut filler storage, and computers 186 and 187 control the flavoring kitchen.

There is also a level 0 computer system controlled by the level I computer system. In the case of primary processing, the level 0 system comprises a plurality of distributed remote modules (DRMs) which interconnect directly to motors, sensors, valves, etc on the processing equipment. The DRMS may be individual computers connected with backup computers and should also be DEC equipment to facilitate communication.

Communication between the primary processing management system computer 132 and the host computers is through an Ethernet collision system while communication between the host computers and the node computers is through a polling type communication link. Communication between the node computer and the DRMs is also carried out via a polling system. The sensor signal values read by the DRMs are stored in memory and periodically read by the controlling node computer. Similarly, these values are then periodically read by the controlling host computer. Conversely, data relating to materials specifications, product specifications, bill of materials lists and process specifications is periodically passed down from the management computer to the host computers, to the node computers and then to the DRMs.

In the case of making and packing, the level 0 system comprises computer control system provided by the equipment manufacturer. This equipment must be modified to be certain of compatibility with the DEC equipment used in the rest of the system. Such modification would be readily apparent to one of ordinary skill in the art. As with primary processing, data relating to sensed variables is periodically polled by the CATC (corresponding to the node computer) and passed up to the host system. Also, data relating to specifications for products, processes, materials and bills of material is passed down to the level 0 computers on a periodic basis as needed.

Figure 3:
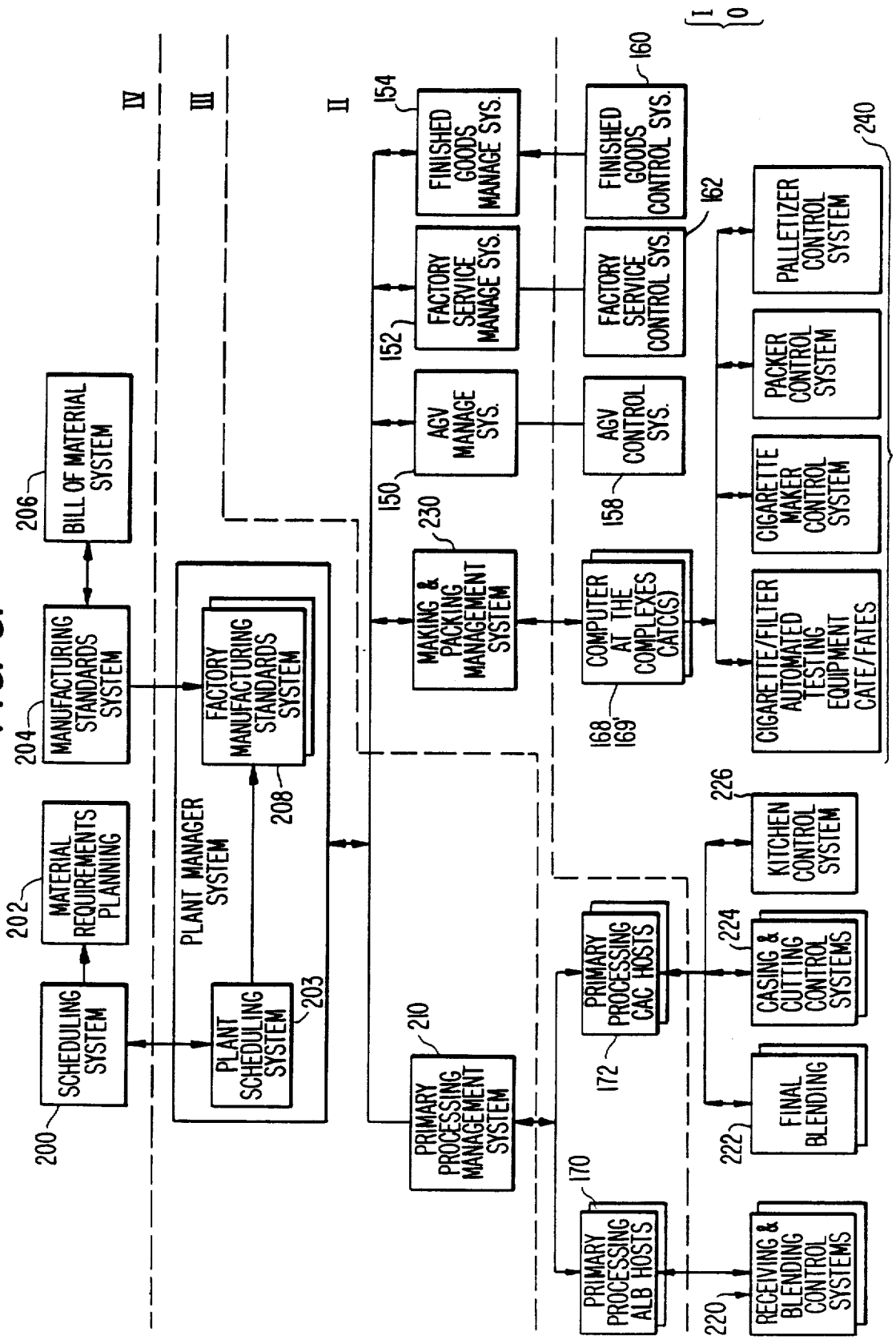
FIG. 3. shows an overview of the organization of the software systems of the computer integrated manufacturing system of the present invention.

FIG. 3 gives a clearer picture of the relationship of the different computer levels and the functions performed at each level. The blocks in FIG. 3 indicate software systems. It should be remembered that level IV is at corporate headquarters and is primarily concerned with corporate objectives. Levels 0–III are at the plant sites and are concerned with carrying out the corporate objectives in the plants. The corporate headquarters is usually removed from the plant site and the information generated at level IV is passed to a plurality of plant sites. Thus, it can be seen that the levels 0–III would be duplicated for each plant site.

As seen in FIG. 3, level IV includes a scheduling system 200 which interfaces with a materials requirement planning system 202. The scheduling system 200 together with the material requirements planning system 202 are designed to manage the manufacturing capacities, machines, people and material to meet the marketing and inventory objectives as stated in the business and strategic plans of the company. The result of this effort at level IV is a master schedule, a portion of which is passed down to a plant scheduling system 203 at the plant level. The master schedule includes a long range portion which matches machine capacity to brand requirement. The long range portion covers a period of approximately 2 to 10 years.

The master schedule also includes a mid-range portion which covers a period of from 1 to 2 years. The mid-range portion applies inventory objectives and calculates the machines and people required. The mid-range plan also sets plant goals.

Furthermore, the master schedule includes a near term portion which covers 1 to 2 quarters. This portion sets near term objectives in terms of inventory level to utilize all employees and establishes machine line-up to accomplish these requirements.

Based on the master schedule, each plant produces a plant schedule covering 1 to 6 weeks. Each plant also creates a daily schedule by finished goods to support the near term master schedule, distribution, advertising promotions and international distribution requirements.

The plant schedule system 203 provides plant execution schedules on a 1 to 6 week horizon. This system assigns machine capacity to achieve the plant demand objectives set by the master schedule.

The manufacturing standards system (MSS) and the bill of materials system interact to produce a database containing all of the specifications and bill of material information needed to produce a finished product. The MSS system contains the capability to issue revisions to specifications and implement the revised specifications according to a predetermined date of implementation.

The database generated in the MSS is passed to the factory manufacturing standards system (FMS) at level III in the plant. The FMS duplicates the majority of the database in the level IV system and also generates an additional file which contains data organized in a manner which can readily interface with the plant scheduling system. This additional file, known as the product definition file, contains records assessable according to scheduable products. Each record contains references or pointers to the specifications and bills of material information necessary to produce a version of one schedulable product. The plant scheduling system operates by accessing the records of the products to be manufactured and passing this information down to the management system(s) involved in making that item.

The plant scheduling system and the factory manufacturing standards system are shown as being a part of an overall block labelled plant manager system. This is because the plant manager system performs functions in addition to the scheduling and FMS functions. These additional functions include those performed by a plant inventory control system and a plant production data base system. These systems gather data and analyze data according to plant and corporate needs. The gathered data may be used in the plant scheduling system and passed to the corporate level IV as the need arises.

The primary processing manager 210 is also a part of the level III systems. The primary processing manager (PPM) receives a product definition file containing the pointers to the specification data from the FMS and converts it into recipes for the various machines under its control. To produce these recipes, the PPM accesses the data indicated by the pointers in the records of the product definition file and assembles this data into recipe file records.

Different machines may be provided on the shop floor to perform the same function and, therefore, may require slightly different operating parameters to function properly. If the data relating to machine settings is associated with a product or group of products, this information is contained in the file passed down from the FMS but the information is not readily usable to directly control the machines. The PPM converts this information into recipes for the various machines by accessing the data and accumulating it in the appropriate recipe record. Also, some operating instructions and machine specifications may be maintained only at the plant level and are not passed down from above since these operating instructions do not relate to any particular product or group of products. These instructions are merged into the recipe by the PPM so that the recipe contains all instructions necessary for operating each machine on the shop floor.

The PPM contains all of the recipes which are scheduled to be run by the machines under its control for a period of about six weeks. These recipes are passed to the host computers 170 and 172 when they are needed. The host computers are at level II and store all of the recipes. The host computers pass down only the recipe for the current run and the recipe for the next subsequent run which are stored in current run and subsequent run registers at level I. As soon as the current run is completed, the recipe for the subsequent run is loaded into the current run registers at level I and the recipe for the next subsequent run is loaded into the subsequent run registers. This is true for both the R&B host 170 and the C&C host 172.

The host computers may store algorithms which are used to convert the recipes into actual set points for the machines on the shop floor. The set points define actual opening degree of valves, speeds of motors, etc used by the control systems. This conversion is made and the set points are passed to the level I systems which are shown to be the receiving and blending control systems 220 connected to the host 170 and the final blending control systems 222, casing and cutting control systems 224 and the kitchen control system 226 connected to host 172.

Data in the form of control variables is sensed by the level 0 system and passed up the levels as discussed above. This data makes its way up to the level III system to be used in the plant scheduling function and is passed up to the level IV system on a selective basis.

The making and packing management system 230 is also part of the level II systems. Management system 230 functions in a manner somewhat similar to the operation of the host computers in that it passes specification data to the 36 level I CATCs as needed to control the present run and the next subsequent run. In this context, the term "run" refers to the production of a scheduled product during a scheduled time period. The CATCs pass the run information on to the computer controls on the machines themselves (indicated generally by 240) which operate on the 0 level.

The CATCs perform data gathering functions by receiving sensor signal data from the machines and then pass this information to the M&P management. The CATCs also receive signals from the machine operator when additional materials are required for the M&P complexes to operate. These requests are passed to the M&P management system which communicates the request to the factory service management system. Since the CATCs store all specification data relating to the current run, when a signal is received that, for example, new cigarette paper is required, the CATC knows the exact specifications of the paper and passes this information along to the M&P management system and then to the factory service management system.

The AGV management system 150, factory service management system 152 and finished goods management system 154 will be discussed in greater detail below.

THE MANUFACTURING STANDARDS SYSTEM (MSS)

Figure 4:
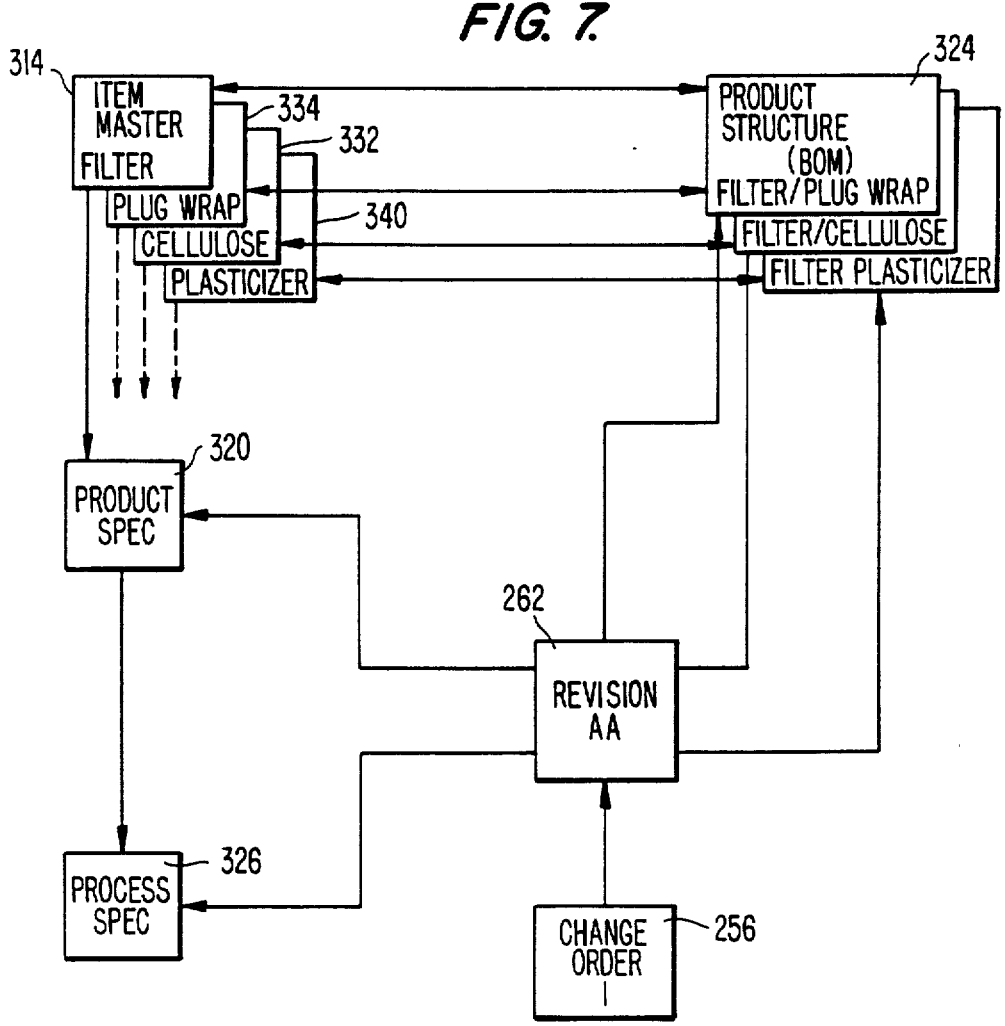
FIG. 4. is a table showing the relationship of the access keys for the manufacturing standards system as they relate to the files of the manufacturing standards system.

The MSS comprises a database containing files which store the various specifications needed for making product. The files are shown in FIG. 4 to comprise a product file 250, a process file 252, a material file 254, a change order file 256, a product structure file 258 (also known as a bill of materials file), an item master file 260, and a revision file 262. The content of each of these files is discussed below.

Before discussing the files themselves, it is helpful to understand the terminology to be used. Accordingly, a brief glossary will now be set forth to ensure an accurate understanding of the present invention.

DEFINITIONS

Terms

1. Product Definition—the assemblage of all Product, Process and Material Specifications, and Bill of Material for a given product.
2. Product—the end result of any manufacturing process (may also be used as a component in the manufacturing of another product).
3. Process—the act of manufacturing a product. Within the scope of the system, it refers to the machine or groups of machines that may be used to manufacture the product.

4. Material—a component in a manufacturing processes that is purchased or in a form that does not require processing prior to use.
5. Product Structure—a list of all materials and intermediate products used to manufacture a product.
6. Active—identifies an approved specification that has not yet reached its expiration date. A specification in an active status could be either approved for future implementation or current, but not obsolete.
7. Inactive—identifies a specification that has not yet been approved for release or is obsolete (expired). A specification in inactive status could be either planned for future implementation or obsolete, but, not current.
8. Current—identifies the one specification for a given product, process or material that is in effect at the point of inquiry. A specification is current if it is approved, its effective date has transpired and no other specification has superseded it at the time of inquiry.
9. Retired—identifies specifications that are no longer in effect or have been superseded. These specifications may still be accessed, as required, due to location dependent phasing in of the new specifications.
10. Future—identifies a specification that is not current yet because either the implementation date has not been approved or the implementation date has not yet arrived.
11. Item-specific—indicates the data in the specification record relates to one item-id only.
12. Generic—indicates that the data in the specification record applies to multiple item-id's that are related by a common parameter, such as grade of paper or machine type.
13. Control—Indicates that the associated data will apply to all records of each specification type. Control records contain maximum and minimum values acceptable for variables in each specification record of a given type.
14. Find number—used in the Product Structure File to indicate the sequence in which a component is to be listed. Used to organize the order in which components of a product are displayed. Also known as line number.
15. Assembly Item-Id—a synonym for the item id of a product.
16. Component Item-Id—a synonym for the item-id of a product for a material that is used as a component in the manufacturing of another product.
17. Finished Good Id—a synonym for the item-id of a final marketable product.
18. Function—a program or series of programs used to accomplish a specific task.

DATA ELEMENTS USED IN ACCESS KEYS

The following data elements are the used in the composition of the main access keys into the files.
1. ITEM-ID—15 bytes alphanumeric—contains the code (identity) by which a product or material is identified. In most cases only the first 8 bytes of this field are used.
2. REV-LEVEL—2 bytes alphanumeric—identifies the revision level of a product spec, process spec, material spec or bill of material of an ITEM-ID. Revisions are assigned in ascending sequence starting from 'AA' and continuing through '99'. At the end of the sequence, the revision level is restarted at 'AA'.
3. SPEC-TYPE—3 bytes alphanumeric—identifies each type of specification by a unique mnemonic code. The spec-type code for each type of specification will appear throughout the rest of these materials after the descriptive name of the record.
4. CURRENT-FLAG—1 byte alphanumeric—is an "on" ('1') and "off" ('blank') switch to indicate whether a specification record is Current.
5. BRAND—4 bytes alphanumeric—contains the brand code which is one of many methods of identifying cigarette products. This data element applies to cigarettes, packages of cigarettes, of cases of cigarettes.
6. MACHINE—15 bytes alphanumeric—used to identify a particular machine type, style or equipment grouping.
7. CHANGE-ORDER-NO—7 bytes alphanumeric—a number issued by the system and assigned by the user to each change. Can be used to relate multiple changes to one or more products, materials, processes, or bills of material such that new specifications can be released together. Field will contain numeric data only.
8. GRADE—24 bytes alphanumeric—defined for materials only and is used to relate multiple ITEM-ID's together in one general classification of materials.
9. APPROVAL-STATUS—1 byte alphanumeric—indicates the approval status of a specification record: incomplete ('I'), pending approval ('P'), approved ('A'), disapproved ('D'), or retired ('R').
10. EFFECTIVE-DATE—6 byte numeric—indicates the date a change contained in a specification record can be implemented in the factories (i.e., becomes current).

ACCESS KEYS

The primary access keys used in the MSS system are defined below with their acutal name and the component data elements that comprise the key.
1. ITEM-REV-KEY=(ITEM ID+REV-LEVEL—Uniquely identifies any specification record for Products and Materials and all Processes related to a specific revision for a Product.
2. CURRENT-ITEM=(ITEM-ID+CURRENT-FLAG)—identifies the Current (in effect at the time of inquiry) revision to a specification for a given ITEM-ID.
3. CURRENT-BRAND=(BRAND+CURRENT-FLAG)—identifies the Current revision to a product specification by BRAND for all cigarette products (including finished goods).
4. CURRENT-SPEC(a)=(SPEC-TYPE+CURRENT-FLAG)—identifies all Current records for a SPEC-TYPE in Selection modules for Products and Materials.
5. CURRENT-SPEC(b)=(SPEC-TYPE+MACHINE+EFFECTIVE-FLAG)—identifies all Current records for a SPEC-TYPE in Selection modules for processes.
6. PROCESS-KEY=(ITEM ID+MACHINE+REV-LEVEL)—Uniquely identifies any specification record for Processes.
7. STRUCTURE-KEY=(ASSEMBLY-ITEM-ID+FIND-NO+COMPONENT-ITEM-ID+REV-LEVEL-IN)—Uniquely identifies any Product Structure record.
8. ITEM-ID is defined as a stand-alone key.

9. CHANGE-ORDER-NO is defined as a stand-alone key.
10. GRADE is defined as a stand-alone key.
11. EFFECTIVE-DATE is defined as a stand-alone key.

FIG. 4 shows the relationship between the keys and the files. The content of the files themselves will now be discussed.

PRODUCT FILE

This file contains the detail specification records for finished and intermediate products. The specifications in this file include specifications for products such as cigarettes (CGT), manufactured filters (FLR), and cut filter tobacco (CFT). In addition, there is a control record for each type of specification. The control record contains the maximum high and low values for specific variables (i.e., reasonableness limits).

The Product file also contains the processes for making the product together with a code indicating the machine on which the processes can be run. From the product file, the process file can be accessed to obtain the specs for carrying out the process. For example under the item id for a particular cigarette, item ids for the processes of cigarette rod making (CRM) and tipping (TPR) would be included together with an indication of the machines on which these processes can be carried out. There may be multiple entries if there are several machines on which the processes can be carried out.

Detail specification records can exist in Retired, Current, or Future status. One record in each file exists for each ITEM-ID/REV-LEVEL combination. Each revision to a specification exists in its entirety.

DETAIL SPECIFICATION RECORDS

Detail specification records contain the detail specifications for cigarettes, filters and cut filler tobacco. The records contain an indication of the SPEC-TYPE. As shown above, the SPEC-TYPE for finished cigarettes is CGT, the SPEC-TYPE for manufactured filers is FLR and the SPEC-TYPE for cut filler tobacco is CFT. The purpose of the SPEC-TYPE is to group all spec records of the same type to facilitate access to all spec records of the same time.

The content of the detail specification records it item-specific. For each ITEM-ID in the Item Master file, to be discussed below, there is only one product specification record identified as current. As shown in FIG. 4, in addition to the ITEM-ID each record of the product file may contain a BRAND code, if applicable, a REV LEVEL code, a CHANGE ORDER #, an EFFECTIVE-DATE-IN code indicating the effective date of the specification, and SPEC DATA indicating the actual specifications of the product. For example, for a finished cigarette, the SPEC DATA may contain the tar and nicotine levels of the cigarette, the moisture content of the cigarette, as well as the length, diameter and other descriptive specifications of the cigarette.

For each detail specification record in the product file, the following information can be accessed directly using the following access keys:

ITEM-REV-KEY—Uniquely identifies each specification revision of any product.
CURRENT-ITEM—Identifies the one Current product specification for an ITEM-ID.
CURRENT-BRAND—Identifies the one Current product specification for each relative SPEC-TYPE for a specific BRAND, if applicable.
CURRENT-SPEC(a)—Identifies all Current product specifications by SPEC-TYPE.
CHANGE-ORDER-NO—Identifies product specifications associated with a Change Order.
EFFECTIVE-DATE—Identifies the date a product specification can be implemented in production.

CONTROL RECORDS

Control records are also provided in the product file. These records contain the reasonableness limits for certain variables in the detail specification records. There will only be one Control record per SPEC-TYPE. The control records can contain, for example, the upper and lower reasonableness limits on tar and nicotine content of the cigarette and the upper and lower reasonableness limits on the diameter or length of the cigarette. The term "reasonableness limits" is used to indicate the upper and lower bounds which any entered spec may have. These limits may be used to test entered specs to be certain that they are not clearly in error.

The control record can be accessed directly by using the following access key:
CURRENT-ITEM—uniquely identifies the current product control record.

PROCESS FILE

The process file 252 contains two types of detail process specifications: item-specific and generic. Item-specific process specifications for each machine type or configuration of machines contain process parameters and instructions for machine setting, etc necesary to produce the desired product. The process parameters and instructions may vary depending on the product to be produced. The machine type or configuration of machines is indicated by a MACHINE data element. Generic process specifications for each machine type or configuration of machines contain process parameters and instructions that will always apply regardless of the product to be produced.

Both item-specific and generic process specifications are included for tipping (TPR), cigarette rod making (CRM), filter rod making (FRM), and cut filter tobacco blending (CFL).

Since only certain machine types are applicable to a manufacturing process, all uses of the MACHINE data element may be validated against values for MACHINE and SPEC-TYPE in a Process Equipment Identification Table maintained for that purpose.

There can be multiple process specification records of the same SPEC-TYPE (e.g., TPR, CRM, CFL) for any ITEM-ID on the Product Specification File. This is due to the differences in producing the same product on two (or more) different types of machines.

Generic and Item-specific specification records can exist in Retired, Current, or Future status. There is one record on file for each ITEM-ID/MACHINE/REV-LEVEL combination. Each revision to a specification exists in its entirety.

DETAIL SPECIFICATION RECORDS

The detail specification records contain the item-specific process specification data. For ech ITEM-ID in the Product file there will be at least one process specification record containing the manufacturing instructions necessary to produce the product. There can be multiple detail process specification recods for an ITEM-ID depending on whether there are any documented machine-related differences.

As shown in FIG. 4, each process file record contains an ITEM-ID code indicating a particular process, a BRAND code, if applicable, a REV LEVEL code indicating the revision level of that particular specification record, a CHANGE ORDER number code, an EFFECTIVE-DATE-IN code indicating the date the specification record is effective, and SPEC DATA indicating the specifications such as the set up instructions, etc for the recorded process. If applicable, the SPEC DATA will have a MACHINE code appended to it to indicate the machine for which the data is valid.

The following information in the detail specification records can be accessed directly using the following access keys:

PROCESS-KEY—Uniquely identifies each specification revision of any process.
CURRENT-SPEC(b)—identifies all Current process specification records by SPEC-TYPE.
CHANGE-ORDER-NO—Identifies Process specifications associated with a Change Order.
EFFECTIVE-DATE—Identifies the date a process specification can be implemented in production.
ITEM-REV-KEY—Identifies all Process specifications associated with a specific revision to an ITEM-ID.

GENERIC SPECIFICATION RECORDS

The generic specification records contain the process specification data that is appliable to a specific machine or configuration of machines regardless of the product being produced on the machine(s). Generic process specification records do not have any references to a specific ITEM-ID. A special value ('GENERIC-' & SPEC-TYPE) is stored in the ITEM-ID. The generic specification records can be accessed directly by using the following access keys:

PROCESS-KEY—Uniquely identifies a Generic Process Specification Record.
CURRENT-SPEC(b)—Identifies the Current Generic Process Specification Record.

CONTROL RECORDS

The control records contain the reasonableness limits for certain variables in the generic and item specific process specification records. There will be only one Control Record per process SPEC-TYPE.

The access key to Control Records has a special value ('CONROL-' & SPEC-TYPE) in ITEM-ID. The access key is:
CURRENT-SPEC(b)—Identifies the Current Control Record for a SPEC-TYPE.

MATERIAL FILE

The material file contains two types of detail specification data for purchased materials: item-specific and generic. Item-specific material specifications contain physical and chemical parameters and supplier instructions that vary depending on the item purchased. Generic material specifications contain process parameters and supplier instructions that will apply to all variations of the same grade regardless of the item purchased.

Material specification data is provided for items such as filter tow (FT), closures (CL), cigarette paper (CP), carton blanks (CR), case blanks (CS), crushproof boxes (CX), foil (FO), purchased filters (FR), inner frame stock (IF), labels (LA), poly wraps (OW), plug wrap (PW), tipping paper (TP), and tear tape (TT). The specification data is similar to that provided in the Product file. That is, descriptive specifications are given for such characteristics as density, color, size, etc. Also, a grade designation is provided, if applicable.

Generic and item-specific specification records can exist in Retired, Current, or Future status. There is one physical record on file for each ITEM-ID/REV-LEVEL combination. Each revision to a specification exists in its entirety.

DETAIL SPECIFICATION RECORDS

The detail specification records contain the item-specific specification data for purchased materials. For each ITEM-ID, there is one Current material specification record. The following information in the detail specification records can be accessed directly using the following access keys:

ITEM-REV-KEY—Uniquely identifies each spec revision of any material.
CURRENT-ITEM—Identifies the one Current material specification for an ITEM-ID.
CURRENT-SPEC(a)—Identifies all Current specifications by SPEC-TYPE.
CHANGE-ORDER-NO—Identifies Material specification revisions associated with a Change Order.
EFFECTIVE-DATE—Identifis the date a material specification may be used to purchase materials.

GENERIC SPECIFICATION RECORDS

The generic specification records contain the generic material specification data for general types of purchased materials. The types included are:
CP—Cigarette paper specifications are related by their grade.
TP—Tipping paper specifications are related by their grade.
OW—Poly wrap specifications are related by their grade.

Generic material specifications have a corresponding entry in the Item Master file. They are linked to the material specifications by the SPEC-TYPE and GRADE. Generic material specifications use the value of the grade in the ITEM-ID.

The generic material specifications can be accessed directly using the following access keys:
ITEM-REV-KEY—uniquely identifies each spec rev of any material.
CURRENT-ITEM—identifies the Current specification for any generic material.

CONTROL RECORDS

The control records contain the reasonableness limits for certain variables in the item-specific and generic material specification records. There is only one Control Record per SPEC-TYPE.

The access key to Control Records has a special value ('CONTROL-' & SPEC-TYPE) in ITEM-ID). The access key is:
CURRENT-ITEM—identifies the Current control record.

CHANGE ORDER FILE

The change order file contains information about each Change Order Number. A Change Order Number is issued by the system and assigned by the user to a specification or bill change or related group of changes.

It is used as a 'connector' into the Revision file to identify all revisions associated with the Change Order.

A Change Order Number must be assigned to each change prior to the creation of a new or revised spec or bill. The system will prohibit updating or creation of specifications or product structures without a valid Change Order Number. The actual implementation of all changes is initiated and controlled through the Change Order as opposed to individual specification revisions.

A Change Order recored contains summary information about the entire change (i.e. effective date, change reason code, approvers, reason description). Each specification record contains its own detail change documentation for that part of the overall change.

The information in the Change Order file can be accessed directly using the following access keys:

CHANGE-ORDER-NO—Uniquely identifies a Change Order record.

STATUS—Identifies the status of Change Order records and is used to group changes by status for display (e.g.. Unapproved, approved, implemented).

EFFECTIVE-DATE—Used to produce chronological lists of pending Change Order records.

PRODUCT STRUCTURE (BILL OF MATERIAL) FILE

The product Structure File is a modified version of the product structure file of a commercially available software package sold by Comserv Corporation of Cincinnati, Ohio under the name AMAPS (Advanced Manufacturing and Production System).

The Product Structure File contains all of the prior, current and future components fo a product by ITEM-ID number and serves two purposes: to provide the relationship of an assembled product to its components (intermediate products and/or purchased materials) and to provide replacement instructions for any component of the assembly. MSS uses this file to generate component lists for selected products. In order to determine which revisions of a component to use, a date selection criteria is applied to each record.

The entries of the product structure file are in terms of product/component. The item id for each component is given but the current rev level for each component is not set forth in the product structure file. This information can be obtained from the item master file or the product, process, or material file containing the specs for the component. The proper product/component relationship to use is determined based on the date selection criteria applied. An example of a product structure record is set forth below.

| PROD/COMP | REV-IN | DATE | REV-OUT | DATE |
|---|---|---|---|---|
| CGT1/TP1 | AA | 1/1/86 | AB | 2/2/86 |
| CGT1/CP1 | AA | 1/1/86 | | |
| CGT1/FLR1 | AA | 1/1/86 | AC | 3/1/86 |
| CGT1/TP2 | AB | 2/1/86 | | |
| CGT1/FLR2 | AC | 3/1/86 | | |

From the foregoing, it can be seen that the first revision AA of the product definition for the cigarette CGT1 established that the tipping paper TP1, cigarette paper CP1 and the filter FLT1 are components. This revision was made effective on 1/1/86. However, this revision was superseded by revision AB which replaced tipping paper TP1 with tipping paper TP2. Accordingly, the REV LEVEL-IN for CGT/TP1 is AA since revision AA called for TP1 as a component and the REV LEVEL-OUT for CGT/TP1 is AB since this revision replaced TP1 with TP2 as of 2/2/86. In a similar manner, revision AC replaced FLR1 with FLR2 so that the REV LEVEL-IN for FLR1 is AA and the REV LEVEL-OUT for FLR1 is AB.

The date criteria is used by accessing the product structure records according to a particular date and using only the components which are in effect as of that date. Actually, only the rev level need be stored in the product structure records, with the effective dates being stored in the rev file. The system is designed to determine the components of the product structure file which are effective on the requested date by reconciling the rev levels with the effective dates stored in the rev file. The component item ids are used to access the item master file to determine the rev level effective on the date requested and the material or product files are accessed to determine the specs for the components as well as the processes needed to produce the component products.

The information in a product structure record can be accessed by using the following access key:

STRUCTURE-KEY—Uniquely identifies a Product Structure record.

ITEM MASTER FILE

The Item Master file is a modified version of an item master file found in the AMAPS software package mentioned above.

The Item Master file contains one record for each assembled product or purchased material referenced in the Product Structure. The record contains information about that item not found in the Product, Process or Material files. For example, the record contains item-specific purchasing data, planning data, and accounting data.

Each item has a unique identifier-its ITEM-ID. Each time a new item is entered into the system, the next available ITEM-ID code is automatically assigned to the new item according to rules established for each spec type.

Item Master records for the assembly and its components must be in this file prior to the creation of a new Product Structure file record. The system includes a function which performs a reference check to ensure that the Assembly ITEM-ID and all Component ITEM-IDs exist before being included in Product Structure file record.

The data in the Item Master file can be accessed directly using the following keys such as the following:

ITEM-ID—Used to obtain any item Master record.

BRAND—accesses information by brand code.

An example of the type of information which may be stored in the Item Master file is as follows:

DESCRIPTIVE INFORMATION

Accounting Information (Inventory Category, Total Budget cost, Cost Control Code, etc.)

Material Control Information (Item Type, Planner/Buyer Code, Make/Buy Code, Order Policy Code, Safety Stock, etc.)

Lead Time Information (Planner Time, Buyer Time, Queue Time, Vendor Time, etc.)

Spec type

Brand code

REVISION FILE

The Revision file is also a modified version of a file contained in the AMAPS software package.

This file is used to track the revisions to any information about each item in the Item Master file. Changes that cause a new revision record to be created for an item include component additions or replacements in its Product Structure or updates to its specification(s). A revision control record must exist prior to accepting any changes to a specification or product structure file.

The Revision file stores codes indicating the revision levels to a spec or bill as well as the effective dates of the spec or bill, and points to the spec or bill data associated with each revision. In this way, the Revision file archives and keeps are record of all changes so that old specs and bills can be accessed and compared to new specs and bills. The following information is stored in this file:

Item-id
Revision level
Effective-date-in
Approval status
Change order number

The information in the Revision file can be accessed directly using the following access keys:

ITEM-REV-KEY—Uniquely identifies a Revision record

CHANGE-ORDER-NO—Identifies all revision records associated with a specific Change Order.

Figure 6:
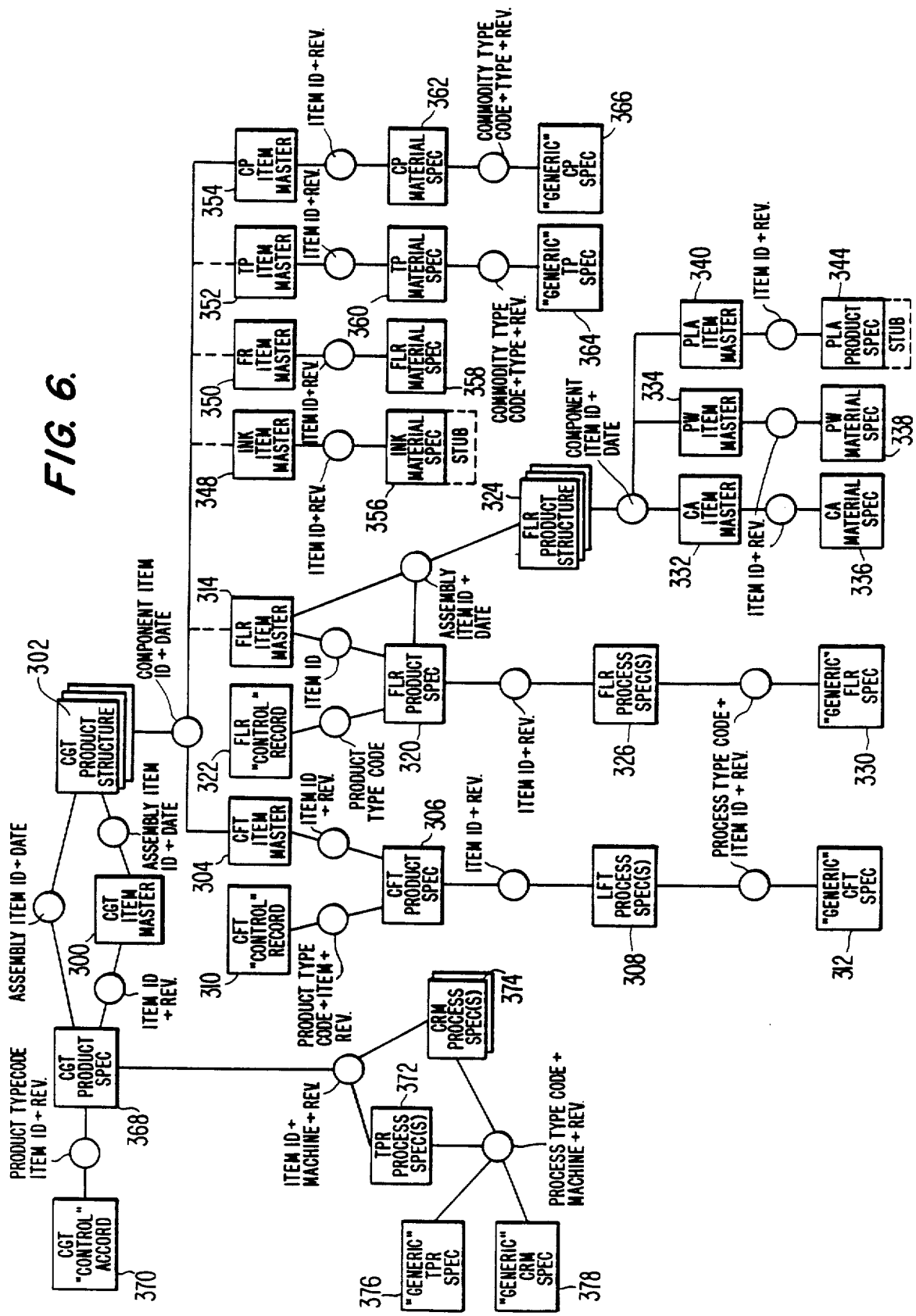
FIG. 6. shows the relationship of the various files of the manufacturing standards system.

By use of the various files discussed above, all information necessary for manufacture and testing of all final products can easily be obtained. FIG. 6 gives an example of the manner in which the information for a particular product can be accessed through the files. FIG. 6 shows th total product definition for a manufactured cigaretted. The record 300 for the particular cigaretted in the Item master file can be accessed with the cigarette brand or any of the other access keys given above together with the date of interest to obtain the item id of the cigarette, if this is unknown, and the rev level of the cigarette. With the item id, and the date of interest, the cigarette record 302 in the product structure file can be accessed as shown in the drawing and the components of the cigarette can be determined. It will be understood that the circular blocks of FIG. 6 indicate the information required to access records in the files and the square blocks indicate the data in the records.

The product structure record 303 for the cigarette of interest lists all of the components of that cigarette together with the item id for each component. Using the various component item id numbers and the date of interest, the item master record for each component can be accessed to determine if the component in question is a material or a product and to obtain the effective rev level as of the date. Then the appropriate material or product record can be accessed. For example, one component of the cigarette is cut filler tobacco (CFT). The CFT item master record may then be accessed using the CFT item id code. From the item master record, it can be determined that the CFT is a product and the CFT product spec 306 can be accessed as well ass the CFL process spec record 308. From the product spec record 306, the control record 310 using the product type code with the item id and rev, and from the process spec record 308, the generic CFT spec record can be accessed using the process type and item id with rev.

In the same manner, the filter (FLR) item master record can be accessed to determine that the filter is a product. From here, the FLR product spec record 320 can be accessed to determine the specifications of the product and the processes used to make the product. Also, the control record spec 322 for the product can be determined. The FLR product structure record 324 can also be accessed using the filter item id and the date to determine the components of the filter. The FLR process spec record 326 can be accessed to determine how to carry out the processes combine the components of the filter and the generic spec can be determined from this record.

In like manner the filter tow (FT) item master record and the plug wrap (PW) item master record can be accessed from the FLR product structure file and then the material spec records 336 and 338 for these materials can be obtained. The same procedure can be used to obtain the item master 340 and product spec record 344 for the plasticizer (PLA).

Likewise, the same procedure can be used to obtain the item master 348, 350, 352 and 354 and material spec records 356, 358, 360 and 362 for the cigarette ink (INK), purchased filter (FR), tipping paper (TP) and cigarette paper (CP), as well as the generic specs for TP and CP.

The cigarette product file recored is accessed to obtain the product specifications and the control record 370 information. Finally, the process spec records for the manufacturing process can be found in the process spec file. This information shows up as tipping process specs (TPR) and cigarette rod process specs (CRM). The generic process specs for the TPR 376 and for the CRM 378 can be found in these records.

From the foregoing example, it can be seen that all information concerning a product can be found using the item id and a date of interest by looking in the correct file. The item id and type of spec can be found in the item master file thus making this the focal point of the connectivity of the files.

Figure 5:
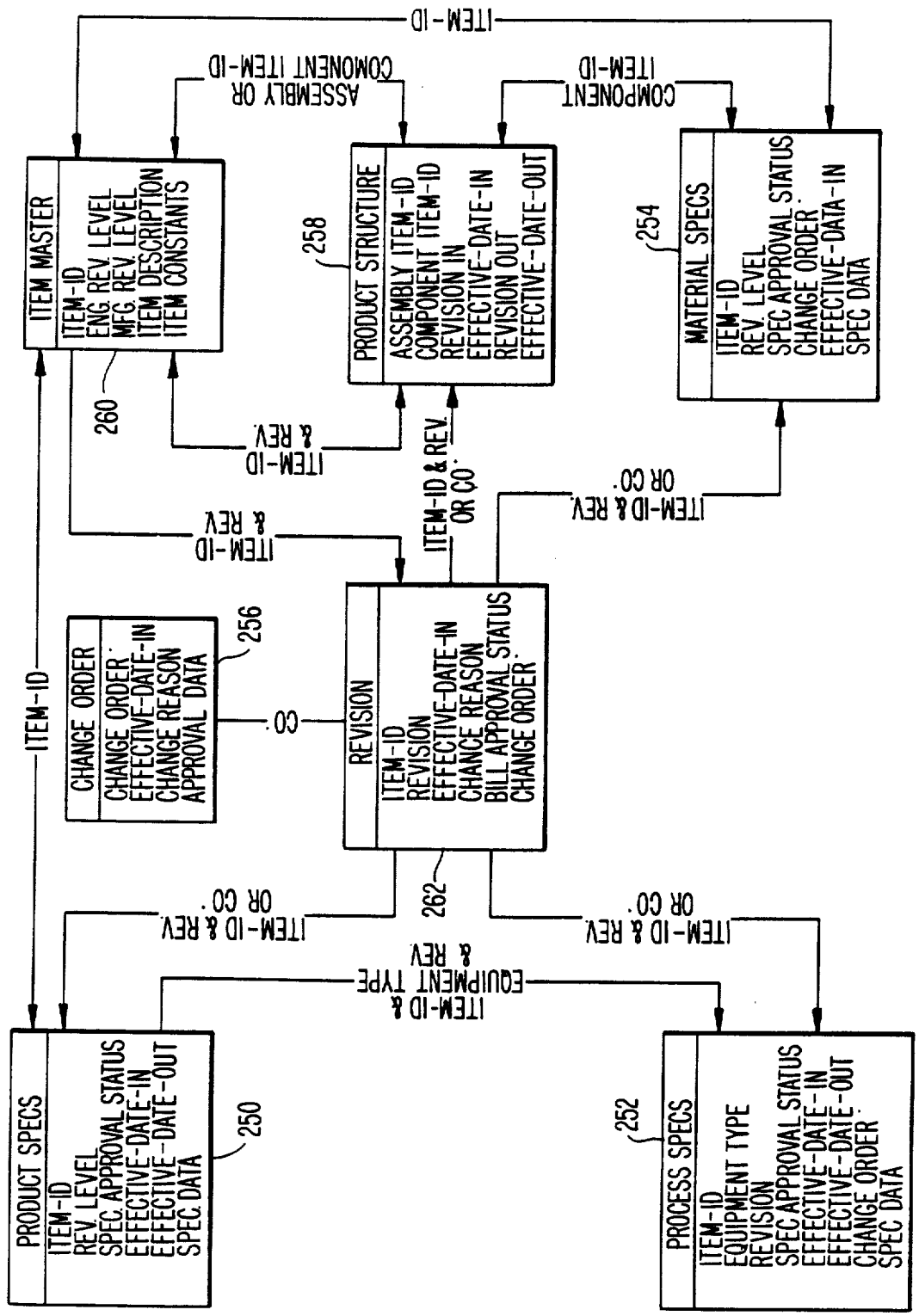
FIG. 5. shows the file organization of the manufacturing standards system of the computer integrated manufacturing system of the present invention.

FIG. 7 shows the relationship between the revision file, the change order file and the other files. The revision file lists all revisions for any item id. The files in FIG. 7 include a portion of the files for the filter as shown in FIG. 5. In addition, the revision file 262 is shown and the change order file 256 is shown. In the revision file a record is maintained for each previous and proposed revision to the specs or bills for each item id. For example, the item master file record for the filter may include revision AC as the current revision implemented for the filter. The revision file would show revision AC is the latest implemented revision under the item id code and would also include entries for the previous revisions AA and AB as well as any other revisions which may be pending but not yet approved, approved but not yet implemented or the like. These same revisions are contained in the appropriate specifications records.

Revisions are produced through use of change orders. A change order is an authorization to create a new product, process, material or bill, or revise an existing spec or bill. For example, if the filter in FIG. 7 was to be changed from a length of 10 mm to a length of 15 mm, a change order must be issued first. The change order number would be required to initiate new specs. These new specs would include changes to all specifications affected by the change in length of the filter. This may include revisions in the product specs and the process specs for making the filter. All these changes would be grouped under the same change order number, for example, change order number 1. In addition, there would be created an entry in the revision file under the item id code corresponding to each item being changed and a new rev designation would be assigned to each change. The changes would also be entered in the appropriate product spec file, process spec file and product structure file by producing a new record under the item id number with the new rev designation.

Under the change order number, there is included effective date information. The effective date of the change order is the date on which the change order should be implemented in the plants. As soon as the change order is approved, the change order and the corresponding new specs and bills are passed down from level IV to the lower level systems so that the plant level is notified of the implementation date of the change order. In this manner, the scheduling systems in the plants can take the change order into account. The actual time of the change order implementation, that is, the shift at which the change order should be implemented, may be left to the plant management system to correspond to the best use of available inventory, machines, etc. all previous revisions of these specs will be used in FMS until such time as the plant level management systems determine when the revisions associated with the change order should be effected.

Figure 8:
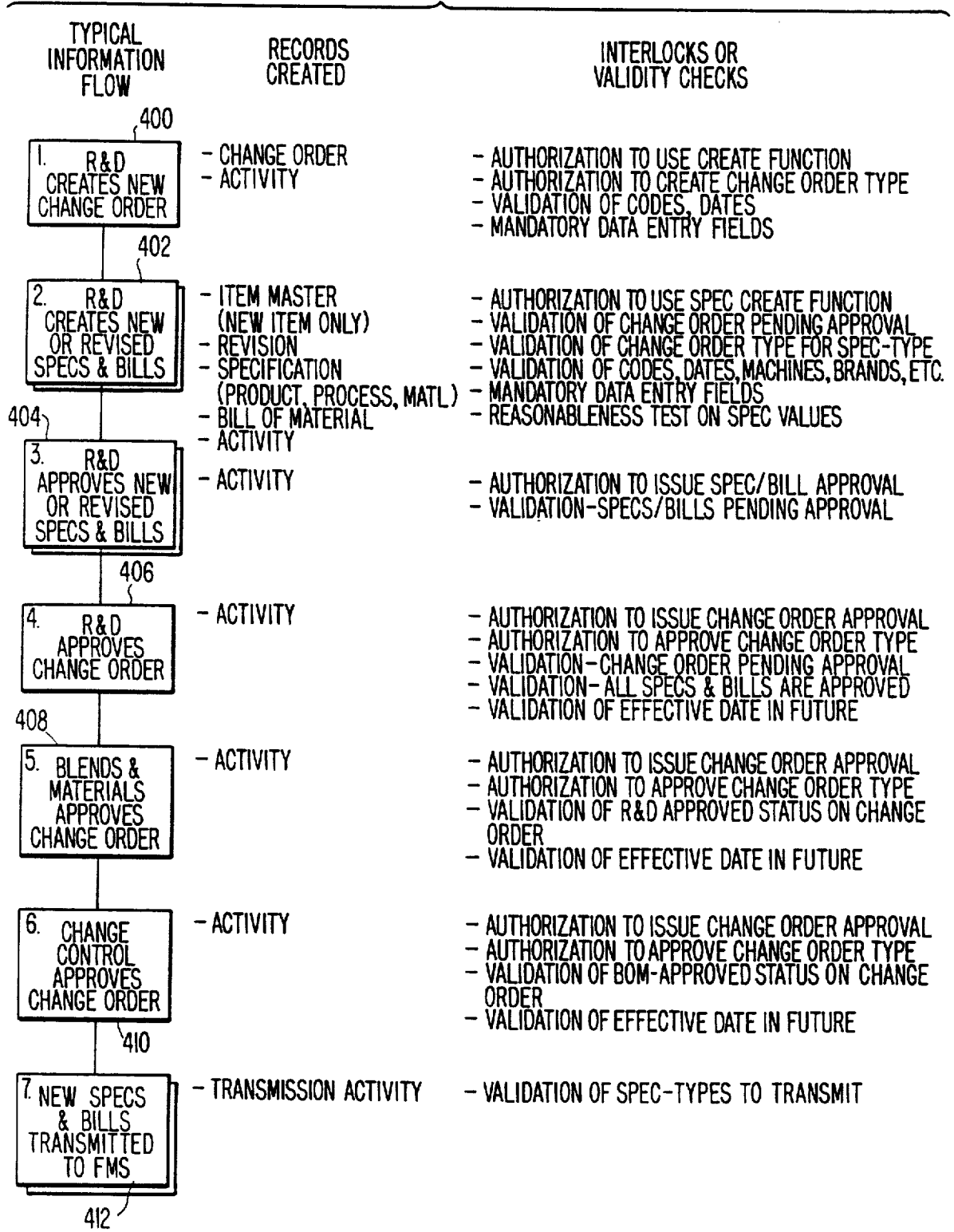
FIG. 8 shows a flow chart depicting the change order implementation sequence of the manufacturing standards system.

FIG. 8 shows the steps to be followed to create and implement a change order. First, in step 400 approval must be obtained to create a change order and a valid change order number must be obtained from the system. In FIG. 8, the steps are shown as being undertaken by the R&D department. Of course, other departments may also be authorized to obtain valid change order numbers. Once a valid change order number is obtained, the user is authorized to input spec or bill data into the system.

In step 402, data is permitted to be input into the appropriate files. Before modification of the specs, the system automatically checks for authorization to use the spec create function, validates the change order as pending approval, and validates the change order as having the proper spec type.

In the event that a new item is being added to the system, MSS automatically creates a new item master file record to obtain a new item id number. The new item id number is then automatically entered into the revision file and the first revision designation AA is assigned to the specs or bills being entered for that item.

If the specs for an already existing item are being revised, the system generates the next rev level entry in the revision file. If the last revision designation for the item id involved was Ac, the new designation would be AD, for example, Data is then entered into the files involved. For example, a new entry may be made in the product specification file under the item id for cigarettes and the new revision level to indicate a new length for the cigarette. All corresponding entries in other files affected must be made at this time. These entries would all come under the same change order number but may have different rev designations depending on the last rev designation assigned to the particular item id number. All entries made at this time are accompanied by an unapproved status code indicating that final approval of the new specs has not yet been obtained.

During modification of the specs, the system validates code, dates (expiration date, etc), machine types, brands, etc. The system also may perform a reasonableness test on the spec values being enetered to be sure that they are not outside of some unacceptable range. Further, particularly if the specs being entered include changes or additions to specs in the bill of materials file, the system may perform a check to see that all fields affected by the entered change receive corresponding changes. Such validations and tests may be performed as deemed necessary to ensure the integrity of the database after the data entry is completed.

At this point, the change order has an unapproved status and each of the data entries has an unapproved status. In step 404, a manual review of each data entry is undertaken by subject matter experts and, if the inspected data entries appear to be correct, the unapproved status of each entry is removed individually. However, the unapproved status of the entire change order remains in effect.

In step 406, the division of the corporation which initiated the change order reviews the specs and bills associated with the change order to ensure that all necessary data entries have been made and that all data entries are correct. The initiating division then approves the change order and may modify the original effective date associated with the change order to implement the change order. If the effective date is modified, the change order and the specifications in the various files are updated en-masse with the new date.

In step 408 and in step 410, other divisions or groups in the organization affected by the change order review the new specs and approve or disapprove of the change order as a whole. Once all involved groups have approved of the change order, the status of the change order is changed to approved. At this point, the change order is automatically transmitted to the plant level in step 412.

Once a change order has been approved and sent down to the level III systems, modifications may still be made. Using the same change order number, the approval can be removed, the change order can be disapproved or the effective date of the change order can be changed.

FACTORY MANUFACTURING SPECIFICATION (FMS) SYSTEM

The FMS stores a duplicate of the database in the MSS except for the unapproved change orders and spec types not applicable to the plant. The FMS automatically creates two new files to organize the spec references in a form which can more readily be married to the scheduling information to be received from the scheduling system.

One of the new files created in the FMS is the Product Definition file. This file contains a record for each product which is the subject of the scheduling system. That is, for each schedulable product a record is created. Schedulable products are products which are stored for use in a subsequent process step. For example, referring to FIG. 1, the output of the receiving and blending section as stored in the group blended strips area 104 is a schedulable product, as is the output of the product stored in the final blended strips area 106. Also, the output of the cutting and casing line as stored in the cut filler storage area is a schedulable product. In the making and packing area, the output on the palletizer to the finished goods area 128 is a schedulable product.

Figure 9:
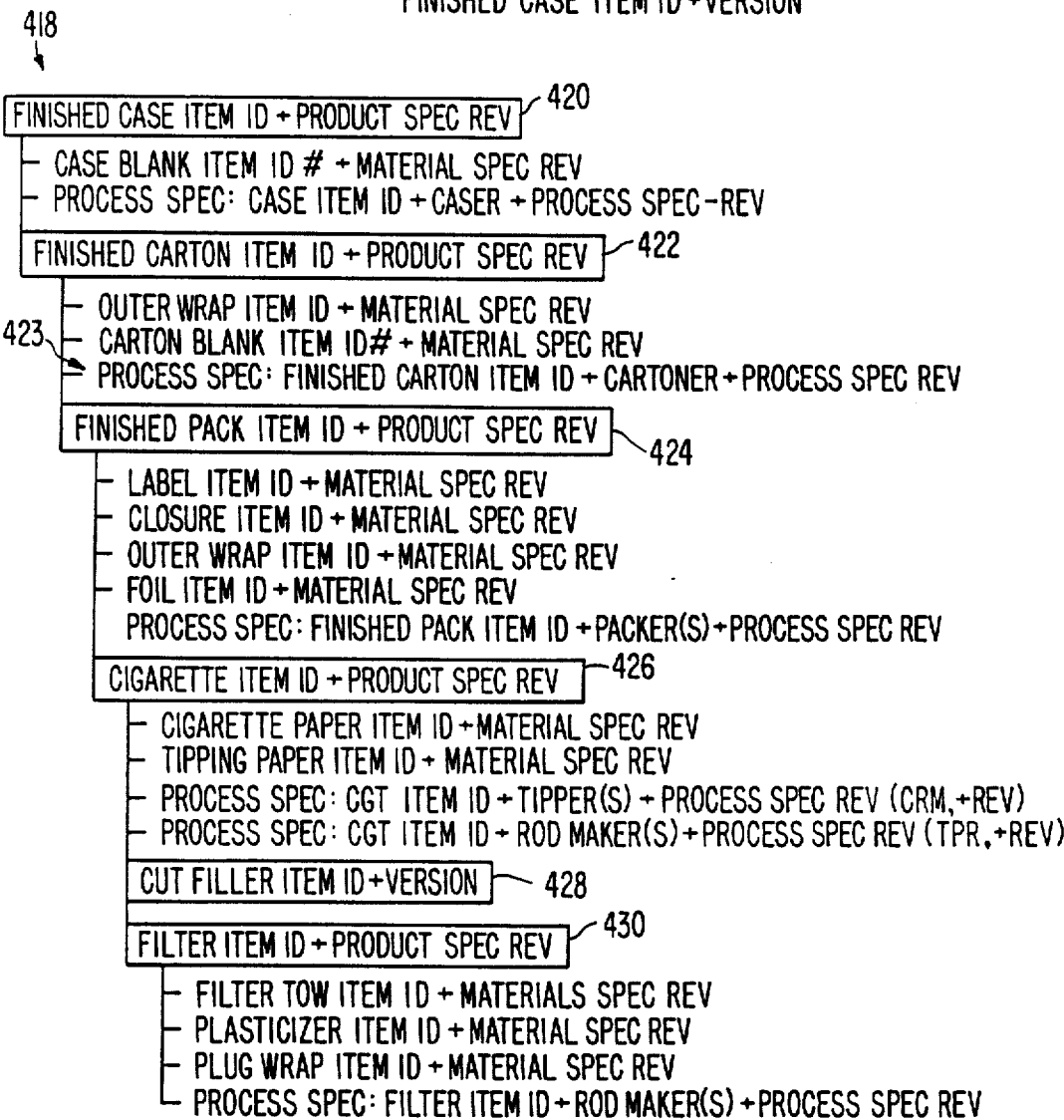
FIG. 9. shows the structure of the product definition file of the factory manufacturing standards system of the present invention.

The purpose of the Product Definition file is to place the specs in a condition which is more suitable for use by the plant management systems, just as the MSS files placed the specs in an organization which was easily usable by the corporate level personnel. FIG. 9 shows one record 418 of the Product Definition file. Each record of the Product Definition file is accessed by reference to the item id of the schedulable product and a version number of the product.

As shown in FIG. 9, the record 418 relates to finished cases of cigarettes and sets forth a full list of all material item ids, process item ids and product item ids needed to produce a finished case structure. Codes are included to distinguish products from materials and processes from products and materials so that the system can discern which components are associated with process specs, which components are associated with product specs and which components are associated with material specs. In FIG. 9, this coding is indicated by boxes surrounding the products and labelling on the processes. That is, from FIG. 9, it can be readily determined that the finished case structure 420, the finished carton 422, the finished pack 424, the manufactured cigarette 426, the cut filler 428 and the filter 430 are products to be manufactured. Accordingly, this information is used to point directly to the appropriate spec files which enable the system to quickly determine all specs of the manufactured product to be used to make that version. The process and material item ids are set forth below each product item id so that the product definition points directly to the materials and processes needed to produce a product. For example, the process spec 423 key is included for the finished carton so that the process specs can be obtained directly.

In addition, codes are included to indicate any other schedulable products in the Product Definition record. In record 418 this is indicated by giving a version number on the cut filler. Accordingly, the system knows that the cut filler is a shcedulable product and can directly access the Product Definition record for the cut filler.

The Product Definition records are assembled by the system using the connectivity relationships as explained with reference to FIG. 6. The system could be run without the Product Definition file by directly determining the relationships of the records as discussed with reference to FIG. 6 each time that this information was needed. However, the formation of the Product Definition file enables the system to operate more efficiently and provides a readily available mechanism for displaying the product definition on a display screen to a user monitoring the status of changes specs within the plant.

The version number of the item id in the Product Definition file relates to the change orders discussed above. Each time a change order is passed down from level IV, a new version of each Product Definition record affected by the change order is produced. In order to keep track of the versions and the dates of implementation of each version, a Configuration Matrix is assembled by the system and stored in the FMS.

FIG. 10 shows the structure of the Configuration Matrix. In FIG. 10, the column indicates the item id code of the schedulable assembly and the upper row indicates the date and shift of implementation. The entries in the matrix indicate the version of the item id to be run on a particular date and a particular shift. Therefore, when a particular item id is scheduled by the plant scheduling system to be run, the Configuration Matrix is accessed to determine the product definition version of the item id which should be used. That version of the product definition is then entered into the schedule and passed to the Primary Processing Management system and/or the Making and Packing Management system.

As discussed above, the date that a change order is to be implemented is passed to the plant level but the actual time of the implementation may be left to the plant level management system. The formation of the Configuration Matrix is a function of the change control administrator which has access to the schedule and to the inventory of the plant. The change control administrator has the flexibility of implementing the change order at the most convenient time for the plant and may make this decision based on factors such as inventory on hand. For example, if a new version of a finished case calls for a cigarette manufactured with a cigarette paper with different graphics, and there is large quantity of the prior cigarette paper on hand, the new version of the item id may not be implemented until late in the day that the change order became effective. Of course, the system could be produced without such flexibility in which case change order would include an actual shift for implementation and the Configuration Matrix would be simply a function of the change order with no input from the change control administrator. In fact, the implementation date of the change order can be accompanied by a code indicating implement immediately, implement as soon as possible, or implement when feasible to direct the actual implementation time. If the change order is accompanied by an implement immediately code, the change order would be implemented on the next shift after it becomes effectie regardless of the unused supply on hand. The change order administrator may be a manual function or software may be derived applying set rules to be followed in the event of the receipt of the codes associated with the implementation date of a change order.

The Configuration Matrix and the Product Definition file provide sufficient information or provide pointers to information in other files maintained in the FMS so that the specs for products to be produced can be accessed by the various management systems in a form which can readily be converted into instructions for the shop level machines. Further, the Product Definition file provides a convenient way in which the information from the scheduling system can access or marry the information from the spec system.

PRODUCTION PLANNING FUNCTIONS

As shown in FIG. 3, the production planning functions on level IV are divided into two general areas, scheduling 200 and material requirements planning 202. The scheduling system determines the quantities of product to be made to meet corporate needs and the materials requirement planning system 202 ensures that there are sufficient people, machines and materials available to meet the production schedule.

SCHEDULING

Figure 11:
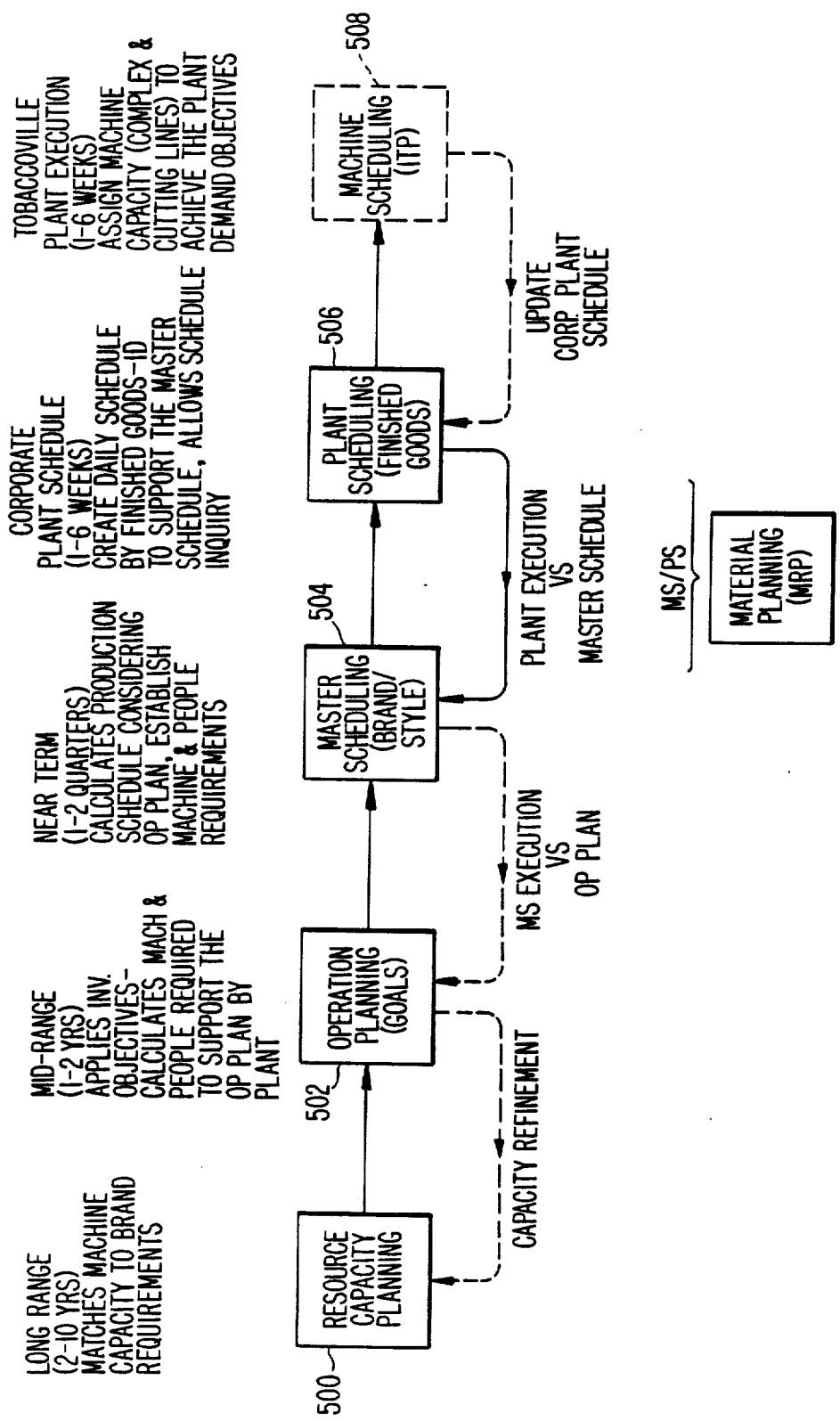
FIG. 11. shows an overall view of the scheduling functions performed in accordance with the present invention.

FIG. 11 shows an overview of the production planning function which forms the scheduling system 200. The Production Planning function starts with long range planning done by Resource Capacity Planning 500 which establishes the capacity requirements of the corporation by quarter. Operations Planning 502 is used to refine the quarterly capacity requirements by applying additional constraints in the form of inventory policies. New monthly goals and budgets can be created from the Op Plan whenever desired. A more refined capacity plan and special scheduling techniques necessary to meet the inventory policies is passed to the Master Production Scheduling function 504 which is responsible for maintaining inventory levels and supporting the Marketing effort on a near term planning horizon. The Master Schedule will apply the people on-roll and modify an existing machine line-up to utilize the people available. The projected inventory levels will reflect the results of utilizing current capacity. All planning up to this point is done by brand/style. That is, the plans are made out in terms of brands required (e.g. Camel, Winston, Winston Light, etc) and style (e.g. cartons, cases, etc).

Plant Scheduling 506 and Machine Scheduling 508 are performed at level III and take the Master Schedule's weekly brand/style requirements and create a detail daily (Plant Schedule) or hourly (Machine Schedule) schedule by specific finished good id for each M&P complex. These two functions define the detail necessary to operate the processing control systems used to operate the plants.

The resource planning 500, operation planning 502, and master scheduling 504 are performed on level IV while the plant scheduling and machine scheduling are carried out at level III.

Material is planned on a weekly basis with daily "call outs" to have material delivered to a plant on the day that the material is required to maintain a predetermined number of days safety lead time.

The production is reported at the end of each shift to provide the necessary information to compare the actual production made and the resources used to the plan production and the resources which were planned.

Figure 12:
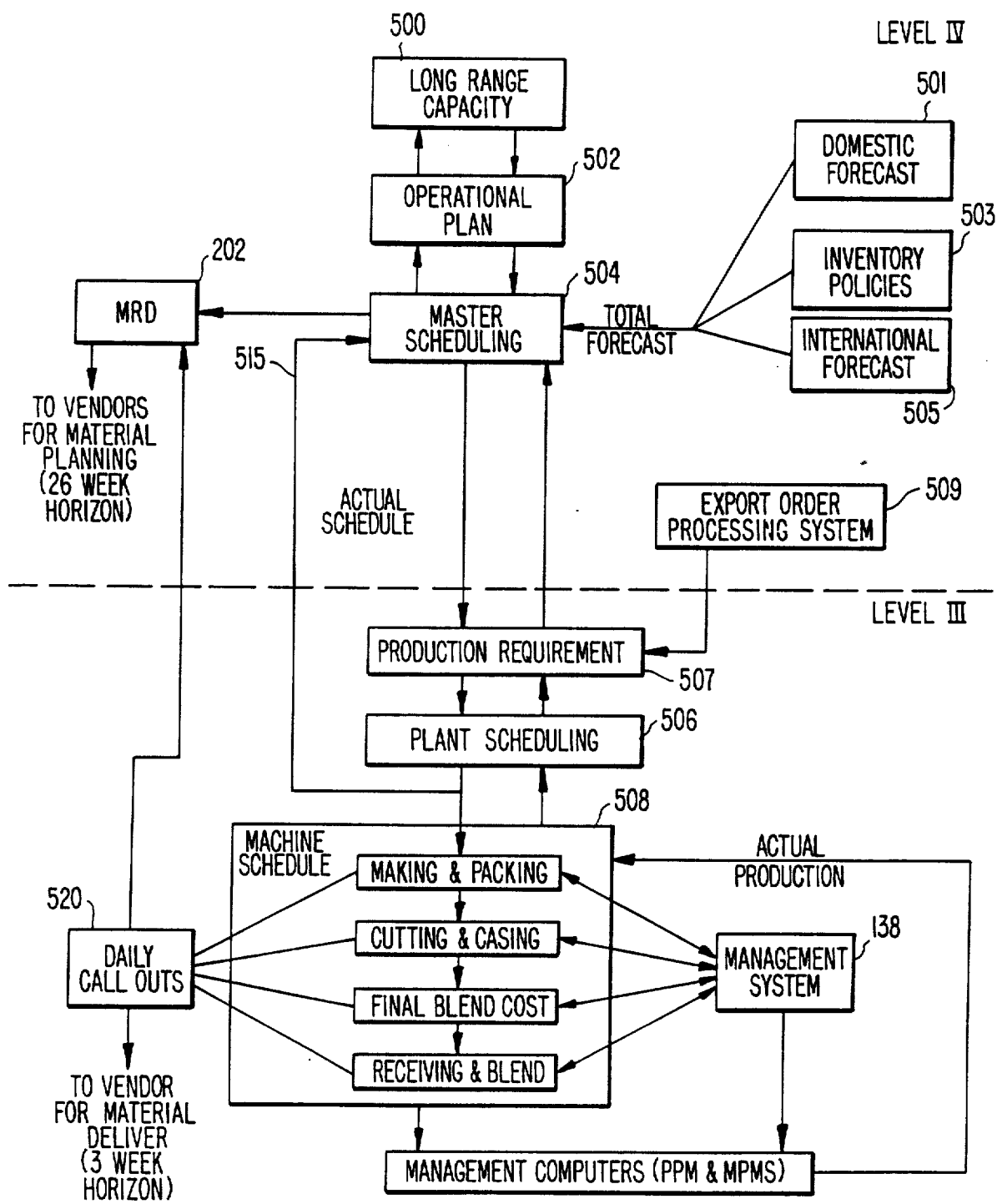
FIG. 12 is a block diagram showing the overall flow of information in the scheduling system of the present invention.

FIG. 12 shows the relationship of the scheduling system with the computer levels and the management systems of the plant. At level IV, the long range or resource capacity planning 500 inputs data relating to the projected long range needs of the company. The operational plan 502 can be a spread sheet type program which can be manipulated to determine the cost, time etc ramifications of different long range plans and different master schedules. In this sense, the operational plan acts as a simulator of the scheduling function. The operational plan results are passed to the master scheduling function 504 which actually creates the master schedule for the company. The master schedule is passed back to the operational plan block which can then model the master plan and determine probable outcomes of alterations to the master plan. All of the information from the operational plan function 502 is passed to the long range plan function 500 to assist in the long range planning of the company.

The master scheduling function receives an indication of the domestic demand from the domestic forecast function 501 which uses well known techniques to predict domestic demand. In addition, the master scheduling function 502 receives demand data from the inventory policies function 503 which determines the desired inventory levels above the domestic forecast in order to compensate for, for example, plant closings for vacation and the like and in order to provide a buffer if demand is above that predicted. Finally, the master scheduling function receives input from the international forecast function which determines the probable international demand for product. This results in a total forecast which must be scheduled by the maste scheduling function.

The master schedule is passed down to the production requirements functional block 507 on level III. The production requirements block 507 also receives orders form the export order processing system. This determines the total demand to be produced by the plant.

It should be understood that the system of FIG. 12 operates on an inventory demand or make to stock system for domestic product and operates on an order demand or make to order system for export product. Accordingly, while the domestic product is inventoried and the domestic forecast can be altered to account for greater demand periods or lower demand period than expected, the export orders are shipped as they are produced and must be given higher priority. Thus, the production requirements block 507 gives priority to the export production requirements and passes on the production requirements for both international and domestic to the plant scheduling block 506.

The plant scheduling block allocates the number of making and packing complexes to international requirements necessary to meet the international orders and allocates the rest of the production capacity to the production domestic product.

The actual plant schedule is passed back to the master schedule block 504 as shown by line 515. The master scheduling block 504 uses this information to adjust the master schedule. For example, if the demand for export was low, more domestic product would have been made by the plant then was called for by the master schedule and the master schedule is then adjusted to take this fact into account.

The machine scheduling block 508 receives the plant schedule and makes out a detailed run by run making and packing schedule to accomplish the plant schedule. From making and packing, the plant operations are back and the cutting and casing lines are scheduled to ensure that the proper product reaches the making and packing complexes at the proper time to meet the plant schedule. The final blended strips lines are then back scheduled from the cutting and casing lines and the receiving and blending lines are back scheduled from the final blended strips lines.

The detailed schedules are down loaded to the PPM and the MPMS and are used to access the product definition files in the plant management system which down loads the specs necessary to carry out the schedules.

The machine schedules are provided about three weeks in advance and are used to provide call outs in the call out function block 520. These call outs are supplied to vendors to order the materials needed to meet the schedule. The materials are then delivered by the vendor just in time to meet the schedule.

The call outs are also provided to the material requirements planning block which also receives the master schedule. The MRP reconciles this information to provide a long term (on the order of 26 weeks) forecast to the vendors for materials demand in the plants.

Also, the actual production figures from the management computers (PPM and MPMS) are sent to the machine scheduling block so that the detailed machine schedules can be adjusted to compensate for short term anomalies in the actual plant production. For example, if one making and packing complex is down for repairs, the production expected from that complex will have to be rescheduled. Any adjustments in the machine schedule are reported back to the plant schedule and to the master schedule so that the plant and master schedules can be appropriately adjusted.

Additional details of the functional blocks of FIG. 12 will now be set forth.

RESOURCE CAPACITY PLANNING

Long range capacity planning is well known in general and is used to match the machine capacity to a Srategic Plan on a one to ten year planning horizon. The main focus of this function is to allocate the machine capacity of a given configuration (85 mm length, 120 mm length, slim, etc.) to the Brand/Styles which make up the various production configurations. Brand/Style allocation to different plants is done to utilize the existing capacity of the plants. Any machine conversion to increase or decrease existing or future capacity is planned by this function. Simulations and 'What if . . . ' questions are answered using the information available to this function.

Long range manpower planning to support the machine capacity can be established by applying the Resource Capacity Planning (RCP) Labor Standards indicating the manpower needed to operate plants and machines. The manpower requirements by labor grade can be generated off the machine line-ups created by the RCP machine planning function.

The Primary capacity and tobacco requriements can be derived from the same machine line-up. Wrapping Material volume can also be calculated by extending the Bills-of-Material with the production volume generated by the machine line-up.

The brand/style placement, machines available, efficiency and the machine utilization created by this function is used to establish the capacity information used by the Operations Planning function.

OPERATIONS PLANNING

Operations Planning is an extension of the Resource Capacity Planning function. Operations Planning (OP Plan) expands the planning of capacity to the weekly horizon and applies additional planning constraints in the form of Inventory Policies. The capacity allocated by RCP may be good for the quarter planned; however, there may be capacity problems on a week to week basis which did not appear. The Op Plan is essentially a simulator of the plants and provides the ability to analyze the capacity problems on a weekly basis. The Op Plan is used to trial fit various scheduling solutions to meet the Inventory Policy objectives. The Op Plan can also be used for simulations and 'What if . . . ' questions.

The manpower requirements by labor grade can be generated by applying the Labor Standards to the line-up. This will calculate the labor requirements to support what is actually needed to meet the inventory objectives based on machine capacity. The machine line-up can be modified up or down to utilize the people on-roll. This modified machine line-up is based on an average men-per machine. The manpower requirements by labor grade can be matched to the Human Resources available for people planning.

Primary requirements, wrapping material and tobacco requirements can be developed using the machine line-up. This information would be on a weekly time horizon.

Manufacturing Goals and Budgets can be created to support the Op Plan upon request. Monthly Manufacturing Goals and Budgets are kept for two years-current and next years. New Manufacturing Goals and Budgets can be established throughout the yeat (Latest Estimate).

The weekly capacity information and the scheduling techniques used to satisfy the inventory objectives are used by the Master Production Schedule to schedule the near-mid term planning horizon.

MASTER SCHEDULING

The Master Production Schedule (MPS) projects the inventory on hand amount by brand/style for the next 78 weeks. The MPS balances the demand to the capacity (machine and/or people) available to establish the production rate by brand/style which the factories must meet in order for the MPS to be met. The MPS breaks the planning horizon into smaller planning periods called "smooth periods". Each "smooth period" has an inventory objective or target to meet as established by the domestic forecast, the international forecast and the inventory policies for the period. The MPS will calculate a smooth machine line-up to accomplish the inventory objective by brand/style based only on machine capacity. The scheduler has the option of applying the people on-roll to the machine line-up in order to modify the smooth line-up to reflect people available. This will cause the smooth line-up to be increased or decreased to utilize the people.

The machine line-up required to meet the MPS indicates how much production each plant must produce by brand/style. Inventory objectives are reconciled by the scheduler using the MPS information.

Labor requirements by labor grade are produced by applying the Labor Standards to the machine line-up. People movement to support the MPS is determined by matching the labor requirements to the Human Resources available.

Primary capacity and wrapping material requirements are established by extending the machine line-up through the Bills of Material.

The MPS generates the weekly machine line-up by brand/style which the plant follows. The first three weeks are in the control of the Plant Schedule. Weeks four through six are reconciled between the Plant Schedulers and the Master Scheduler. The MPS will create a new smooth line-up for weeks 7 through the end of the first "smooth" planning period.

The MPS calculates and maintains inventory by brand/style. Each brand/style has a standard finished goods id which is produced unless overridden by the Plant Scheduler. This standard finished goods id is used for all material planning functions generated from the MPS.

A new production plan is created each time the Master Production Schedule (MPS) is executed. The new production plan is based on the current inventory balances, the Plant Schedule for the first six weeks and the inventory policy (target levels) which the Master Scheduler is aiming to achieve. A new machine line-up is generated for weeks seven to the end of the planning period to utilize the people on-roll to accomplish the inventory policy. The machine line-up for the first six weeks may need modification to bring the Plant Schedule in line with the Master Schedule requirements or because the plant capacity may have changed. A Line-Up report is used by the Master Scheduler and the Plant Schedulers to reconcile the line-up. The machine line-up in the Master Schedule is modified to reflect the latest plant capacity as defined by the Plant Schedulers. A new Plant Schedule for weeks four, five and six is created from the new machine line-up established in the Master Schedule. The Plant Schedulers have complete control of the Plant Schedule for weeks one, two and three. These weeks are NOT modified by the Master Schedule.

The weekly machine line-up generated by the Master Schedule specifies the number of machines to run in each plant-department by brand/style. The assignment of brand/style production to the desired plant-department was made by the capacity priority established for each brand/style by the Master Scheduler. The weekly machine line-up assumes that same number of machines will be ran each day at the same efficiency rate. A machine line-up which is less than a whole machine represents a split daily production: ie a weekly machine line-up of 2.2 means a daily machine line-up of 2 machines for four days and 3 machines for one day.

PLANT SCHEDULE

The Plant Schedule takes the weekly MPS requirements and creates a daily machine line-up for the standard finished good id as defined by the MPS. The Plant Schedule allows for special finished good items to be scheduled. When a special finished good item is scheduled the Plant Schedule subtracts the amount from the standard finished good item. An example of this is the scheduling of export items. If 100 million cigarettes is scheduled for the standard domestic finished good item and 10 million cigarettes were scheduled for an export order the standard domestic finished good item would be reduced to 90 million cigarettes. The original target of 100 million cigarettes for the brand/style is maintained; however, the specific finished goods which make up the brand/style will change according to the demand for specific items.

The Plant Schedule provides the daily machine line-up and production volume which runs the plant. All supporting plant functions, such as material requirements, primary production, machine overhaul schedules, are scheduled from the Plant Schedule.

The Plant Schedule provides a daily run sheet which lists the items to be produced (by finished good id), the number of machines required to produce the volume required, the efficiency rate used to calculate the machine line-up and the labor staffing required to operate the machine line-up by labor grade. A "pick" list showing each wrapping material component required to produce each finished good item is also provided.

The Master Scheduling functions support the corporate inventory policies established to reach a corporate Business Plan. The first six weeks of the Master Schedule are refined and reconciled using current plant capacity information (people and machines) as defined in the Plant Schedule. The Plant Schedule for weeks four, five and six is regenerated to reflect this reconciliation. The Plant Schedule for weeks one, two and three are under control of the Plant Scheduler and can only be changed in the Plant Schedule which is than reflected in the first three weeks of the Master Schedule. This interaction between the Master Schedule and the Plant Schedule establishes a detail Making & Packing schedule. The Primary facilities are backed scheduled from the Making & Packing schedule. These functions are performed on the level IV system.

Each plant maintains their Plant Schedule on the plant level III computer. The Plant Schedule information is transferred between the corporate level IV computer and the plant level III computer. Bill-of-material and manufacturing specifications will vary between plants. The Plant Schedule maintained in each plant provides the ability for each plant to schedule where and when a Product will be produced. The Factory Manufacturing System maintained in each plant defines how a product is made and the material necessary to produce the product on the date which it is scheduled to be produced. The Machine Schedule generated from the Plant Schedule produces a detail sequence of runs by work center (complex or primary line) for each item-id and the date/shift it is to produced. The detail Machine Schedule is married to the product definition via the configuration matrix to determine the version of the product to produce based on the item-id and the date/shift it is scheduled to be produced. The marriage of the Machine Schedule and product definition determines where, when and how a product will be made.

The level II computer is a staging area for the detail runs waiting for processing. A one day to one week holding tank is maintained at this level. Minor alterations to the scheduled runs can be made at this level by authorized schedulers.

The actual processing of the runs is done by the level one computers. The level one computers provide information on the current run and the next run to be produced. The product to be made, the facilities to be scheduled and the Manufacturing Standards to use are loaded into the processing computers and displayed to the machine operators. Authorized machine operators can alter the schedule and/or components materials and process set points in order to maintain production requirements.

The Plant Schedule defines which complex(s) (Maker-Packer) produces which brand/styles. Daily capacity available is maintained for each complex-brand/style. The Plant Scheduler assigns a Priority to each complex which can produce a given brand/style. The machine line-up established by the Master Schedule is allocated to specific complex assigned by the Plant Scheduler. The following example shows how this is accomplished:

Machine line-up established by the Master Schedule is 11 machines for the week or 2.2 machines a day. Export requirements will need 3 machines during the week. The standard domestic finished goods item id to schedule is 5124010 and the generic export finished goods item is in 7924000 (this reserves capacity to produce specific export orders at a latter date).

| ARRAY | MON 12/15 | TUE 12/16 | WED 12/17 | THUR 12/18 | FRI 12/19 | WEEK | FG-ID |
|---|---|---|---|---|---|---|---|
| PRIORITY - 1 COMPLEX 5 | | | | | | | |
| MACH-AVAIL | 1 | 1 | 1 | 1 | 1 | 5 | |
| OVERHAUL | 0 | 0 | 0 | 0 | 0 | 0 | |
| EFFICIENCY | 62.3 | 62.3 | 52.3 | 52.3 | 62.3 | 62.3 | |
| DOM MACH SCHED | 0 | 0 | 0 | 1 | 1 | 2 | 5124010 |
| EXP MACH SCHED | 1 | 1 | 1 | 0 | 0 | 3 | 7924000 |
| PRIORITY - 2 COMPLEX 6 | | | | | | | |

| ARRAY | MON 12/15 | TUE 12/16 | WED 12/17 | THUR 12/18 | FRI 12/19 | WEEK | FG-ID |
|---|---|---|---|---|---|---|---|
| MACH-AVAIL | 0 | 0 | 0 | 0 | 1 | 1 | |
| OVERHAUL | 1 | 1 | 1 | 1 | 0 | 4 | |
| EFFICIENCY | 62.3 | 62.3 | 62.3 | 62.3 | 62.3 | 62.3 | |
| DOM MACH SCHED | 0 | 0 | 0 | 0 | 1 | 1 | 5124010 |
| EXP MACH SCHED | 0 | 0 | 0 | 0 | 0 | 0 | |
| PRIORITY - 3 COMPLEX 1 | | | | | | | |
| MACH-AVAIL | 1 | 1 | 1 | 1 | 1 | 5 | |
| OVERHAUL | 0 | 0 | 0 | 0 | 0 | 0 | |
| EFFICIENCY | 62.3 | 62.3 | 62.3 | 62.3 | 62.3 | 62.3 | |
| DOM MACH SCHED | 1 | 1 | 1 | 1 | 1 | 5 | 5124010 |
| EXP MACH SCHED | 0 | 0 | 0 | 0 | 0 | 0 | |
| PRIORITY - 4 COMPLEX 2 | | | | | | | |
| MACH-AVAIL | 1 | 1 | 1 | 0 | 0 | 3 | |
| OVERHAUL | 0 | 0 | 0 | 1 | 1 | 2 | |
| EFFICIENCY | 62.3 | 62.3 | 62.3 | 62.3 | 62.3 | 62.3 | |
| DOM MACH SCHED | 0 | 0 | 0 | 0 | 0 | 0 | |
| EXP MACH SCHED | 0 | 0 | 0 | 0 | 0 | 0 | |
| TOT MACH SCHED | 2 | 2 | 2 | 2 | 3 | 11 | |

The first complex to be scheduled is complex 5. There are five machines available during the week for this complex so all are used. Export requirements take three of the five days and are scheduled for Monday, Tuesday and Wednesday. The second priority is complex 6. This complex is being overhauled until Friday. The complex is scheduled on Friday when it becomes available. Only six machines have been scheduled on the first two priorities. The remaining five machines to schedule are done on complex 1 because the complex is available all week. Complex 2 is not needed by this brand/style and is available for another brand/style if required. A detail Plant Schedule by day for the specific finished goods id 5124010 and the generic export finished goods id 7924000 has been created.

The machine capacity reserved for export items is identified by the finished goods id 7924000. This reserved capacity will be consumed by actual export orders. Any capacity left over will be converted to the standard domestic finished goods item 5124010. Additional export capacity will be taken from the same standard domestic finished goods item.

During the creation of the Plant Schedule, all outstanding export orders are gathered for the next three weeks. The export orders are grouped by brand/style, due-date and blend. The export machine capacity is consumed by the specific export orders based on this grouping. The amount of machine time required to produce an export order is determined by the machine's rated speed and efficiency rate. Backing off the due-date by the amount of machine time required to produce this export order yields the start date/time. This information provides the Plant Schedule with the run sequence to schedule the export orders.

Returning to our example, we have four export orders to schedule for the current week. The following data is known:

| FINISHED GOODS ID | EXPORT ORDER | CASES | MM/CIG | DUE-DATE |
|---|---|---|---|---|
| 6924044 | 63373896 | 100 | 1.000 | 1/15 |
| 6924056 | 63394058 | 65 | .650 | 1/16 |
| 6924056 | 63394059 | 30 | .300 | 1/16 |
| 6924027 | 63365420 | 100 | 1.000 | 1/19 |

The complex to schedule can produce two million cigarettes based on the machine speed and the current efficiency rate. The first three export orders will be scheduled on Monday to meet the due dates. The remaining capacity of fifty-thousand cigarettes (2 million-1.950 million) will be scheduled as the standard domestic finished goods item. The last export order will be scheduled on Wednesday with the remaining capacity that day being converted to the standard domestic item. The export capacity reserved for Tuesday was not used; therefore, the capacity is scheduled for the standard domestic item. Note that this will cause the Plant Schedule to over schedule the domestic item and under schedule the export capacity requested by the International forecast. The total amount of the brand/style which was scheduled by the Master Schedule was maintained; however, the mix was not. The next Master Schedule run will take this over production into account when a new production schedule is generated.

A detail Plant Schedule has been created from the Master Schedule and outstanding export orders (the same logic of scheduling export orders is applied with specific domestic orders requested by Distribution such as test markets and cold storage items). The Plant Scheduler has the ability to manually override or add to the generated schedule. This is done by using the add request or the change schedule request. These functions are covered in the Plant Scheduling User Manual.

MACHINE SCHEDULING

The final step in scheduling the Production facilities is the Machine Scheduling function. This function takes the daily machine line-up from the Plant Schedule and provides a hourly run schedule to operate a specific complex (maker-packer combination) and make a specific finished good item. The Primary facilities are scheduled using the hourly run schedules. This information is passed to the processing systems which operate the facilities.

1. MAKING AND PACKING

A detail run schedule is created for each work center based on the Plant Schedule established in the above manner. The first Machine Schedule which is created is for the Making & Packing operations. The daily Plant Schedule is divided into the varius runs required to produce the finished goods scheduled. The start time and end time for each run is calculated using the machine speed and the current efficiency rate. The Cut Filler Storage (CFS) bulkers and the Feeder to support the complex are scheduled using the default assignment established by the Plant Scheduler. The Plant Scheduler can modify the CFS bulker and/or feeder assignment upon request. The following information is provided in the Machine Schedule for Making & Packing:

| WC | RUN | FG ID | ORDER # | S | DATE | START | DATE | END | FD | CASES |
|---|---|---|---|---|---|---|---|---|---|---|
| 5A_05 | 010 | 5124010 | 63373896 | 7 | 15-DEC | 00:00 | 15-DEC | 08:00 | 25 | 0195 |
| 5A_05 | 020 | 6924056 | 63373896 | 8 | 15-DEC | 08:00 | 15-DEC | 11:12 | 25 | 0100 |
| 5A_05 | 030 | 6924056 | 63394058 | 8 | 15-DEC | 11:12 | 15-DEC | 13:39 | 25 | 0065 |
| 5A_05 | 040 | 6924056 | 63394059 | 8 | 15-DEC | 13:39 | 15-DEC | 14:36 | 25 | 0030 |
| 5A_05 | 050 | 5124010 |  | 8 | 15-DEC | 14:36 | 15-DEC | 16:00 | 25 | 0023 |
| 5A_05 | 060 | 5124010 |  | 9 | 15-DEC | 16:00 | 15-DEC | 23:59 | 25 | 0195 |
| 5A_05 | 070 | 5124010 |  | 7 | 15-DEC | 00:00 | 16-DEC | 08:00 | 25 | 0195 |

Where WC is the Work Center (sub-unit and complex); RUN is the run sequence number; FG ID is the finished goods item to be produced; ORDER # is the specific order number; S is the shift: DATE is the day the run is to start on: START is the planned start time; DATE is the day the run is to end; END is the planned end time; FD is the feeder to use; CASES is the amount of cases to produce.

The Machine Schedule is matached with the configuration matrix to ascertain the version to be used for the finished goods item. The version to be used is the one in effect for the date of the run. Run 010 above for finished goods 5124010 needs to have the version in effect during the 7 shift on December 15th. The correct version is added to the detail runs created by the Machine Schedule.

The Primary facilitites are now ready to be back scheduled. There are three areas in Primary to be scheduled. They are the Casing & Cutting lines, the Final Blended Strip lines and the Receiving & Blending lines.

lated using this information. The CFS bulker replenishment schedule is derived by knowing when a bulker will be depleted and when it is required to be used again. A replenishment window exists when the Casing & Cutting line can be used to produce the run to replenish the bulker. Based on the replenishment window and the amount of time required to produce the amount of the blend needed, the four Casing & Cutting lines are scheduled to meet the CFS replenishment schedule.

Following is an example of a CFS bulker depletion schedule and the replenishment window necessary to fill a depleted bulker prior to the next schedule usage of that bulker.

|  | MONDAY | | | TUESDAY | | | WEDNESDAY | | | THURSDAY | | | FRIDAY | | |
|---|---|---|---|---|---|---|---|---|---|---|---|---|---|---|---|
| shift > | 7 | 8 | 9 | 7 | 8 | 9 | 7 | 8 | 9 | 7 | 8 | 9 | 7 | 8 | 9 |
| CFS 10 | \|ddd-H133-dd\| | | | | | | 4>\|dd-H133-dd\| | | | | | | 8>\|dd-F120-d\| | | |
| CFS 11 | | | | 2>\|ddd-H133-ddd\| | | | | | | 6>\|dd-H133-d\| | | | | | |
| CFS 12 | \|-G10-\| | | | | | | 3>\|ddd-G10-ddd\| | | | | | | 7>\|dd-G10-ddd\| | | |
| CFS 13 | | | | 1>\|dd-G10-dd\| | | | | | | 5>\|dd-G10-dd\| | | | 9>\|d-G10-\| | | |
| C&C 01 | 1G101 | | | 2H1332 | | | 4H1334 | | | 6H13367G107 | | | 8F12089G109 | | |
| C&C 02 | | | | 3G103 | | | 5G105 | | | | | | | | |

The projected CFS bulker depletion is shown as |dX99d|. The blend code is shown within the brackets. The replenishment window is the time between when the bulker is depleted and the next time it is scheduled for use. The first replenishment window for CFS 10 is between the 7th shift on Tuesday and the 7th shift on Wednesday. The blend, H133, can be produced anytime within this window to support the Making & Packing schedule which generated the need. The corresponding Casing & Cutting schedule is developed by meeting the replenishment windows. The Casing & Cutting runs are bracketed by the CFS replenishment run number.

The Machine Schedule created for the Casing & Cutting lines is illustrated below.

| WC | RUN | BLEND | S | DATE | START | DATE | END | DT | SO | POUNDS |
|---|---|---|---|---|---|---|---|---|---|---|
| CC_01 | 010 | G10 | 8 | 15-DEC | 08:30 | 15-DEC | 13:00 | 13 | 01 | 68,000 |
| CC_01 | 020 | H133 | 9 | 15-DEC | 16:00 | 15-DEC | 18:00 | 11 | 02 | 68,000 |
| CC_01 | 030 | H133 | 8 | 16-DEC | 12:30 | 16-DEC | 15:39 | 10 | 02 | 68,000 |
| CC_01 | 040 | H133 | 8 | 17-DEC | 09:30 | 17-DEC | 14:00 | 11 | 01 | 50,000 |
| CC_01 | 050 | G10 | 9 | 17-DEC | 16:00 | 17-DEC | 18:00 | 12 | 03 | 68,000 |
| CC_01 | 060 | F120 | 8 | 18-DEC | 13:00 | 18-DEC | 15:59 | 10 | 01 | 48,000 |
| CC_01 | 070 | G10 | 9 | 18-DEC | 16:00 | 18-DEC | 20:00 | 13 | 02 | 32,000 |

2. CASING AND CUTTING

The Casing & Cutting lines support the Cut Filler Storage bulker replenishment schedule. The first phase of the Casing & Cutting schedule is to determine the CFS bulker replenishment schedule. The Making & Packing run schedule specifies the CFS bulkers assigned to support each complex. The status of which CFS bulkers are currently in use, which blends are in the CFS bulkers and the amount of tobacco in each bulker is provided when a new schedule is to be calculated. The CFS bulker depletion projection is calculated.

Where WC is the Work Center (Casing & Cutting line); RUN is the run sequence number; BLEND is the item to be produced; S is the shift; DATE is the day the run is to start on: START is the planned start time; DATE is the day the run is to end; END is the planned end time; DT is the CFS bulker to receive the production: SO is the FBS bulker which will supply the tobacco for this run: and POUNDS is the amount of cut filler to produce.

The version of the blend to produce is derived from the Factory Manufacturing Standards in the same manner as the Making & Packing version number. The product definition for the blend is looked up in the configuration matrix and the version in effect for the date and shift is ascertained.

3. FINAL BLENDED STRIPS

The FBS lines are scheduled in the same fashion as the Casing & Cutting lines were. The FBS bulker depletion schedule is calculated using the FBS bulker status and the Casing & Cutting schedule generated above. Requests for additional FBS (Part 2) tobacco to support other facilities or international tobacco orders will be added to the Casing & Cutting schedule. The FBS replenishment schedule is then calculated to fit in the replenishment window. The two FBS lines are then scheduled to support the FBS bulker replenishment schedule. The same illustration shown for the Casing & Cutting schedule is appropriate for the FBS area.

4. GROUP BLENDED STRIPS

The FBS line schedule is used to calculate the GBS bulker depletion schedule. Using the same logic as defined for the Casing & Cutting and FBS areas applies for the GBS area. When the depletion schedule is known the replenishment window and schedule can be calculated. The three Receiving & Blending lines are than scheduled to support the GBS replenishment schedule.

MATERIAL REQUIREMENTS PLANNING

Material Requirements Planning is divided into two planning horizons. Long range material planning is done for a 26 week period. The material required to support the Master Schedule is calculated by taking the current balance on-hand and projecting when the material will be consumed. Material requirements are calculated for each of the 26 weeks in the planning horizon. The material requirements are based on the standard finished good item which is scheduled by the Master Schedule.

The "call outs" are created to support the detail Plant Schedule. The "call outs" are calculated by subtracting the daily material requirements from the inventory on-hand at the plant. Material is ordered to maintain a predetermined number of days safety lead time. The specific wrapping material is ordered to support the specific finished good ids which are scheduled by Plant Scheduling.

Actual production and the machine line-up used to produce the finished good items is reported at the end of each production shift. This information is entered into the Plant Scheduling function. This allows for the comparison of actual vs. plan. Various position-to-date comparisons are provided. The detail production and plan is summarized by various groupings up to the brand/style level. Performance measurements can compare actual labor vs. plan labor, actual material used vs. planned material usage, actual production volume vs. Master Schedule requirements, actual labor vs. Op Plan labor requirements, Master Schedule vs. Op Plan. Any number of other comparisons can be provided to evaluate the execution to the plan.

Actual material deliveries are compared to the daily "call outs" to evaluate the material delivery function.

PRIMARY PROCESSING

Figure 2B:
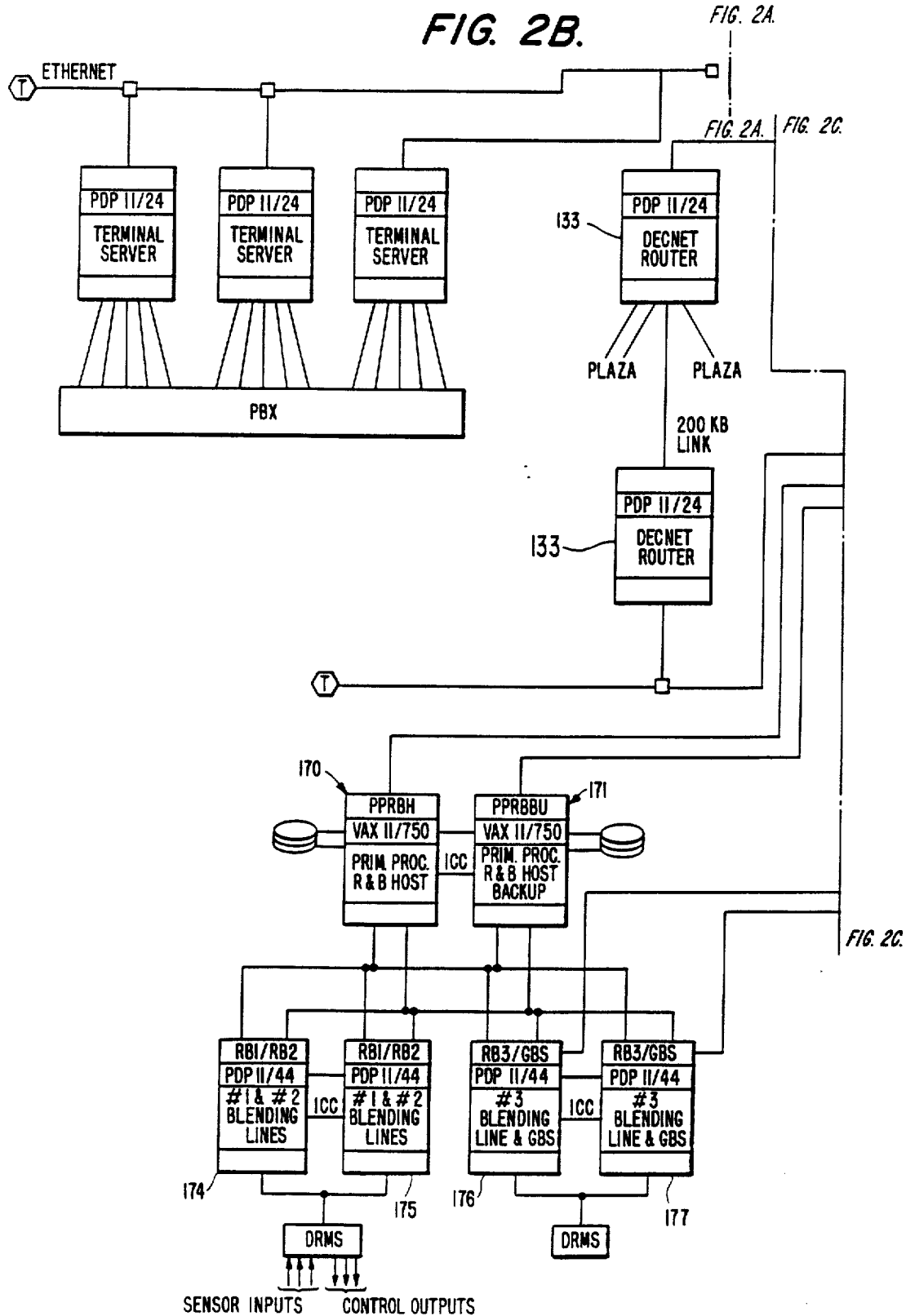

Primary Processing is broken into three major areas which consist of Receiving and Blending/Group Blended Strips including areas 100, 102 and 104 of FIG. 1, the Final Blended Strip area 106, and the Casing and Cutting/Cut Filler Storage comprising areas 108, 110, 112, 114 and 116. These areas are controlled by the Level III Primary Processing Manager 210 (FIG. 3), two redundant Level II host computer systems 170, 171 and 173, 173 (FIG. 2b) and a plurality of Level I node computers and Level 0 Distributed remote processors as also shown in FIG. 2b.

The basic configuration of the Level II, Level I and Level 0 computers is based on a hardware system sold under the name Anatec and a software system sold under the name CRISP provided by Anaconda Advanced Technology, Inc. CRISP 32 is used on the Level II system and CRISP 16 is used on the Level I system. CRISP is a conventional layered software package which permits application programs to written for the ANATEC system. The Anatec system uses DEC computers. The CRISP package includes databases which will be referred to below as CRISP databases. These databases are stored in the memories of the computers on the individual levels of the system. Communication is provided between the levels using CRISP routines, as will be referred to below. In addition to the CRISP routines, a DECnet router 133 (FIGS. 2a and 2b) is provided for communicating between disk storage on the different level computers, as will become apparent below. Also, a mailbox communication system is provided and a Network Sender/Receiver is provided. These are standard communication features the details of which are apparent to one of ordinary skill in the art. The Network/Receiver is an applications program which uses the DECnet router to communicate between different levels of the system.

The Primary Processing Management functions are divided between the level III system 210 of FIG. 3 and the level II host systems 170 and 171. That is, there is no clear distinction between functions performed on the Level II system which should be considered management functions and which should not. Therefore, the term Primary Processing Management System (PPMS) will be used hereafter to refer to the functions performed both by the system 210 and the hosts systems 170 and 172. A distinction will be made, however, by referring to either the PPMS level II system or the PPMS, level III system where appropriate to indicate the functions performed on each level.

In addition to the Primary Processing Management System, a Distributed Processor Control System (DPCS) is provided to control the operation of the DRMs on Level 0. The DPCS is a software function which resides on Level 1.

It will be understood that a large number of programs are used to carry out the functions discussed below. What is important to the present invention is the function being carried out and the system level on which the function is performed as well as the level on which data is stored to enable the function to be performed. Once this information is clear, it is considered to be a routine matter to provide the coding to carry out the functions. Therefore, a detailed description of the coding will be omitted from the present discussion.

The PPMS is an area management system which assists many departments in the plant as well as outside the plant in providing two types of control: material and production.

From a material standpoint, the PPMS is accountable for maintaining real-time inventories in an Inventory function. In order to maintain such inventories, the system provides the following:

(1) up-to-date inventory balances and status by item and plant location for each raw material and work-in-process;

(2) an Inventory Control function with inventory position transactions by item, location and run level each shift;

(3) integration between other systems to effect the transfer of inventory detail simultaneously which physical material movement.

The Inventory function provides several subfunctions. A Material-On-Hand sub-function provides plant management with status of displays of in-process and floor inventories of all materials used or produced in the Primary process. These displays are updated every sixty seconds to give real-time data to the viewer.

PPMS also contains an In-Plant Inventory Update sub-function which is responsible for keeping the in-plant inventory records up-to-date based on:

(1) receipt and shipment data as collected at a receiving area where this information is input to the system;

(2) inventory adjustment data as collected from other systems;

(3) batch/run history data as collected from the Level I system and supplied to the PPMS Batch/Run History sub-function.

It should be understood that the receiving area where information is input to the system concerning receipt and shipment data is referred to as the Primary Receiving System (PRS). The PRS keeps track of inventories of tobacco and other materials being brought into the plant and inventories of product being shipped. This information is input to the system and used as discussed below.

PPM's Batch/Run History sub-function is actually a combination of an Inventory function and a Production Reporting function. This function is responsible for:

(1) collecting end of run data from Level I, (2) notifying the Inventory function about the availability of data, (3) updating a Transaction Logger with the new data, (4) furnishing the Scheduling system with the proper data about the finished run, and (5) providing plant personnel with displays and hard copies of the run's data.

The Transaction Logger collects all of the inventory transactions that occur in a given period (receipts, shipments, adjustments, usage, and production) and provides the data daily to the Level IV systems for a variety of uses.

The PPMS Production Reporting function uses data supplied by a Material-On-Hand function and the Transaction Logger to provide shift and daily reports on items such as material usage and inventory status.

A Receiving and Blending (R&B) Grade Entry Interface at the Grade Entry area 100 (FIG. 1) provides R&B personnel with the proper bale material identification as bales are prepared to be consumed in the R&B operation. This data is based on scanning of bar codes on the tobacco bales as the bales are prepared to be processed. The bar code data is input to the system relative to each bale received and supplies in real-time the data necessary to determine if the bale should be used at a particular point in time.

In regard to the production control, the PPMS ensures the ability of the Level I systems to meet the required standards for making product in Primary. For this purpose, the PPMS includes a Recipe and Operating Instruction function which, along with the Manufacturing Standards System and the Factory Manufacturing Standards System, marries corporate controlled specifications with plant controlled specifications to supply the Level I computers with the necessary recipe components and operating instructions for the production runs. The Recipe and Operating Instruction function produces a Recipe File and an Operating Instruction File using information from the MSS database and information relating to plant owned data. The records in these files are then passed down to the lower levels for use in controlling the processes of Primary Processing.

The PPMS also includes a Scheduling function which aids in keeping an orderly and coordinated sequence to the production runs. In conjunction with the Plant Scheduling System 203 (FIG. 3), PPMS supplies the tools to adjust the schedule to accommodate problems which develop in the system.

LEVEL III PPMS SOFTWARE

The Level III software provides all of the direct user interface with the PPMS. Additional user interface in Primary Processing (but not with the PPMS) may be had at the Distributed Processor Control System (DPCS) which resides in Level I and actually controls the operation of the distributed remote processors (DRMs of FIG. 2b). All PPMS displays, edits, and requests for hard copy reports are made through Level III software.

In addition to the PPMS user interface, the Level III software provides interface between the PPMS and:

(1) the Manufacturing Standards System 204 (FIG. 3) via the Factory Manufacturing Standards System 208 (FIG. 3), (2) the Plant Scheduling System 203 (FIG. 3), and (3) the Material Requirements Planning function 202 (FIG. 3) on Level IV to pass off inventory transaction data.

DATA COLLECTION/USER INTERFACE RECIPE AND OPERATING INSTRUCTIONS

The PPMS organizes and provides the plant personnel with the necessary display and edit capabilities of the recipe and operating instructions required to make the various blending runs in Primary Processing. The recipe and operating instructions must be available at Level I before a production run can be made.

Recipe data is generally characterized as data contained in a particular blend's Bill of Material. Operating Instructions are the various set points, limits and ranges for items like temperatures and moisture levels that are used to control and monitor the making of blends.

Recipes and operating instructions are the standards by which the various processes are controlled. In some cases, the data is provided by the Level IV system through the MSS and this data is considered to be corporate data and is stored in the common disc storage area 166 (FIG. 2a) as part of the FMS database. The corporate data associated with any particular blend can be accessed by reference to the appropriate record of the Product Definition File which points to the pertinent records and files of the FMS database. In other cases, the data is controlled at the plant level and is considered to be plant-owned.

By reference to the appropriate Product Definition File record, the PPMS forms two files. One file, referred to hereafter as the Operating Instruction File, contains a record for each blend/version indicating the operating instructions for that blend/version. The operating instructions comprise actual operating parameters such as set points, pressures, flow rates, etc. The other file, referred to hereafter as the Recipe File, contains a record for each blend/version indicating the recipe for that blend/version. The Recipe File contains quantities of the components to be used in a particular blend/version such as the amounts of the different types of tobacco to be used to make a blend/version.

It should be noted that in the Primary Processing area the schedulable items are in fact different tobacco blends being prepared for use in the Making and Packing area. Accordingly, during the remainder of this discussion, the term "blend" will be used interchangeably with the term "scheduable item."

In the case of the Recipe File and the Operating Instruction file, the data is maintained at PPMS Level III in the common disc storage area 166. The plant owned data in these files actually augments the corporate data by adding to information which is specific to the equipment in that plant and is necessary to produce product on machines of that plant. Examples of plant owned data may include set point ranges of particular equipment, ranges of valves settings to provide a certain flow rate, etc.

The entries in the Operating Instruction File and the Recipe File which contain corporate data cannot be changed by the plant personnel. For corporate data, the PPMS provides display-only capability for the user of this information. This means that if the data needs to be altered, it must be done through a change order in the MSS at Level IV and then resupplied to the PPMS. The interface of the PPMS to the MSS is described below.

The entries of the Operating Instruction File and the Recipe File which comprise plant data can be altered by the plant personnel. Plant owned data can be edited through the PPMS. Editing of plant-owned data will also be described in more detail below.

The plant owned data and the corporate data are merged in the Operating Instruction File and the Recipe File stored in the PPMS once the corporate data is available to the Level III system. In regard to this merging, there are three cases to consider, as follows:
(1) handling the interface to a new blend (a new item id which is to become a new schedulable item);
(2) interfacing to a new blend/version which has at least one previous version on the system (adding plant owned data to a new version of an existing schedulable item); and
(3) changing plant owned data for a blend when the corporate data is not being changed (altering plant owned data in a record for an existing item id + version).

In the first case, when a new blend is introduced to a plant, none of the plant-owned data exists for the particular blend/version. Before the blend can become a schedulable item, plant personnel must enter at Level III the plant-owned specifications which are required to enable that plant to produce the new blend. This data is then merged by PPMS with the corporate-owned data in the Operating Instruction File and the Recipe File. This provides a complete set of data to be passed to Level I so that any run that has been scheduled with the new blend will not be prevented from being passed to Level I due to a lack of proper data.

The second case involves providing a set of plant-owned data for a new version of a blend that already existed on Level III as a previous version. Upon receiving notification of a new version of a blend, Level III PPMS surveys the Recipe and Operating Instruction Files to determine if this blend already exists in some form as a previous version. If a previous version is found, PPMS will use its plant owned data as the default set for the new version of the blend. Management procedures must be in place to assure that the data that is being used in the revised blend specifications are the required values.

In case three, there is a desired change to the plant-owned data but the corporate data does not require a change. The user will request the particular blend/version to be modified. The user will make the required changes and then accept the changes. The new plant-owned data will automatically replace the old plant-owned data for the particular blend/version without changing the identifying blend/version. In other words, the identifying blend/version number is based on the corporate data and revisions in the corporate data only will produce a new version number.

As will be understood from the foregoing discussion, only one set of plant-owned data will be kept for any individual blend/version. Once the changes are made at Level III, the changes are made known to Level II and subsequently Level I such that when the particular blend/version is next called for in the schedule, the new set of plant-owned data will be used.

The computers of the Level I system store in memory buffers as a part of their CRISP database only the blend/version records for the current run and the next subsequent run. If the blend/version requiring a change in the plant-owned data is already in the current run buffer or the next run buffer in the Level I system, the data will not change unless the buffers are cleared and the blend/version is re-requested.

The corporate and plant-owned data for each section of the plant can be displayed for review and editing purposes. Of course, only the plant-owned data can be edited, as discussed above.

The data for the Receiving and Blending area is displayed in two screens. One screen is used to display the recipe or bill of material type information. The second screen is used to edit and display the various operating instructions required to control the process.

Two screens are used to display and edit the information relating to the Final Blended Strip area. One screen is used to display the recipe or bill of material type information. The second screen is used to edit and display the various operating instructions required for the Final Blended Strip part of the operation.

Three screens are used to display the information relating to Casing and Cutting and Cut Filler areas. One screen is used to display the recipe or bill of material type information. This screen also allows for the edit and display of the high/low, minimum/maximum values for each of the material data items supplied by corporate. These ranges are plant-owned and are stored in the same record as the data item to which they relate. The second screen is used to edit and display parameters in the process which have set points, high/low limits and minimum/maximums associated with them.

These parameters may also be plant owned and are stored in the Operating Instruction File. The third screen allows the edit and display of the operating points for moisture meters used in some processes and data for the top dressing tank number used in the casing process and the display of the top dressing menthol indicator used to indicate the production of menthol product.

The number of screens used and the information displayed on each screen depends on the total amount of information to be displayed and the need to review the information. Also, the format of the displayed information is discretionary, although a standard column display has proven very effective. In every case, the information to be displayed on accessed based on the blend/version code of the product to which it relates.

SCHEDULING

PPMS Level III provides plant personnel with the capability to display, edit, and print the schedules for each line in the Primary Processing area. Schedules are generated at Level IV and passed down to Level III. As part of the Level III Plant Scheduling and Machine Scheduling functions, any necessary modifications are made to the schedules and the schedules are finalized or committed. The main purpose of the editing of the schedule at Level III is to make last minute changes to the schedule or to add runs that were rejected by the down loading procedure. Before a schedule is passed down to Level II or to Level I, the schedule must be committed through a Level III Commit function. This is a manual function which authorizes the schedule to be used. This is done each time that a schedule is changed at a higher level, even if no changes are made at the PPMS Level III.

In most instances, the schedule will be used as provided by the higher level systems. However, in the event that changes are necessary, manual intervention through the PPMS commit function is possible. The manual intervention is in the form of alterations in the schedule made by displaying the current schedule, altering the schedule as needed and then storing the altered schedule. This type of manual intervention provides flexibility to the system to accommodate unpredictable events which cause unexpected alterations in the schedule.

INVENTORY

One of the important functions of an automated manufacturing system is the collection of data relating to inventory. An accurate indication of inventory on hand is necessary to ensure that the schedule can be carried out in a timely manner and to ensure that orders for replacement materials can be made in a timely manner.

The inventory data collection function of the present invention is divided into two sections. The first section pertains to the Material On-Hand function. The second section is the inventory adjustments programs.

PPMS provides numerous displays to allow the user to view various inventory items in the Primary Processing areas. The inventory items include floor items which consist of types and amounts of unprocessed tobacco on hand as well as partially processed tobacco received into the plant from another location but not yet used in any processes within the plant, and material held in bulkers such as the amounts types of flavorings on hand and the amounts and types of partially processed tobacco on hand in bulkers. Inventory data at Level III is stored in one major Inventory File which is stored in the common disc storage area 166. This file is a collection of data from the Level II R&B host computers 170,171 (FIG. 2b) and the Level II Casing and Cutting host computers 172,173. The data is gathered approximately every 60 seconds from the Level II computers and provides an accurate snapshot of the amount of each item contained in the Primary inventory.

Individual displays can be provided for each type of item in the inventory. For example individual displays can be provided for processed tobacco inventory, various types of floor inventories and the status of various bins. This provides an immediate visual indication of the on-hand amount of the various materials in the plant.

In addition to providing current inventory displays, PPMS provides programs to permit the updating of the plant's inventory maintained at the plant and the updating of the plant's inventory maintained at Level IV. These programs allow for modifying inventories of various types of materials. For example, different types of tobacco may be handled by different programs. One program may be provided for modifying Redried Leaf tobacco inventory. A second program may be provided for modifying Oriental Leaf tobacco inventory. A third program may be provided to permit the changing of miscellaneous floor inventory other than Redried Leaf or Oriental Leaf. Three adjustment displays are used to update the in-plant inventory maintained by PPMS and the Level IV plant inventory for the three types of inventories being kept. The operation of each display is functionally the same. The user requests one of the screens. The user then enters the pertinent data that will identify the material to be adjusted. The program, based on the key data, will search the proper inventory file for data relating to the material. The information is then displayed to the user. After the user makes the appropriate changes, the new information is used to update the PPMS in-plant inventory. The changes made are also logged to update the Level IV plant inventory at the end of the day.

The foregoing discussion of inventory adjustment programs relates to adjustments of floor items which consist primarily of unprocessed tobacco but may also include partially processed tobacco received into the plant but not yet used in any process in the plant. Another program is provided for allowing the entry of adjustments to materials stored in bulkers (in process tobacco within the plant) or tanks (such as flavorings). Normally, the levels of materials in bulkers or tanks is indicated by sensors in the bulkers or the tanks. If one of these sensors fails to provide an accurate indication, an adjustment may be made to the indicated level in the inventories at the scheduling system and Level IV using this program. Entries made through this program indicate an inventory transaction to the higher level inventory but do not alter the in-plant inventory maintained by PPMS. That is, the level indication by the faulty sensor will remain until the sensor is repaired. Manual adjustments to the inventory must be made until the sensor is repaired.

EXTERNAL SYSTEMS INTERFACE

Level III of PPMS interfaces with the Factory Manufacturing Standards system, with the Level II of PPMS and Level I. These interfaces are for the purpose of passing information upward from lower level systems to higher level systems and for passing information downward from higher systems to lower level systems.

The interface with the Factory Manufacturing Standards is to collect specification data supplied by corporate systems for the various new and revised blends. PPMS marries this data with information supplied by plant personnel for items considered to be plant owned specifications.

The interface with Level II of PPMS is to supply the combined data mentioned above to the various areas of Primary Processing. This is done to insure that each area has its data when the schedule requires the particular blend to be run. A similar interface occurs with Level I to assure that a copy is available at the lowest level for backup purposes.

PPMS maintains a list of the various blend/revision combinations of specifications that it has supplied from Level III to Levels II and I. When a scheduled run indicates a blend/revision combination that PPMS does not have a record of down loading to the lower levels, PPMS access the Factory Manufacturing Standards database to get the proper corporate data to prepare for down loading to the lower levels.

The data that is collected from the Factory Manufacturing Standards is merged with data input at the plant level that is also part of the specifications for making a particular blend/revision combination. Upon completion of the merging of corporate and plant data, a message is sent to Levels II and I that the data is available to be copied to the respective levels. The manner in which the data is copied to the lower levels is discussed in greater detail below.

The data that is copied is a combination of the new data and the old data. This data replaces whatever was previously stored at Levels II and I. After the corporate data has been combined with the plant data, the file containing the Receiving and Blending data is transmitted to the Level II PPMS and to the level I DPCS.

The Level II system is notified via the Network Sender/Receiver that the data is ready to be moved to Level II. PPMS at Level II then copies all of the specification data for the area from Level III to disk storage associated with the host computers at Level II. This action is performed by a direct disk to disk transfer to the disks of the active and idle Level II systems. At this point, the data replaces the previous specification information for the area.

In passing the data to Level I, the data is pushed from Level III directly to Level I. The Level I computers also have disk storage available to them. A copy of the all the specifications pertinent to the Level I computers is maintained in the disk storage of these computers as backup data.

Also, as will be discussed in greater detail below, each Level I computer has a current run memory buffer and a next run memory buffer which are part of their CRISP database and are loaded from the Level II system with the specification data for the current and next runs, respectively. This is the information which is actually used to carry out the processes in Primary.

As mentioned above, the information to be stored on the disks of the Level I system is sent via a direct disk to disk transfer. As is the case for Level II, the data replaces old specification data on both the active and idle computers of the redundant computer systems at Level I. As will be discussed in greater detail below, the data stored on the disk storage for the Level I computers acts as backup for the data loaded into the current and next run memory buffers by the Level II system in the event that there is a failure in the system.

The operation for handling the R&B, Final Blended Strip and Casing and Cutting areas is the same except that only one set of computers is involved at Level I for the Final Blended Strip area whereas there are two sets involved in the R&B area and the Casing and Cutting area, as can be seen with reference to FIG. 2b.

Level III of PPMS also interfaces with the Plant Schedule System 203 (FIG. 3) which generates the Plant Schedule and the Machine Schedule. The interface between the PPMS and the Plant Schedule System occurs after the Plant Schedule System receives a new schedule from Level IV. The new schedule is married with the specs in the FMS and the schedule information is passed on to the PPMS. The new schedule is then validated by the PPMS Level III. Upon completion of the work at Level III, the user signifies to the system that the schedule for a line needs to be committed to Level II. PPMS Level III then signifies through the Network Sender/Receiver that there is a new schedule for a line. Level II then brings the new schedule down and replaces the old schedule. The new schedule is then ready for use by the Level II system to supply next run and shift schedules to the CRISP database on Level I. These schedules are also maintained on Level I as a backup measure in the event that there is a failure in the loading procedure wherein the Level II system Loads only the current run specifications and the next run specifications in the memory buffers of the Level I computers.

There are three interfaces between Level III of PPMS and the other systems in relation to inventory reporting. These interfaces involve the accumulation of information from lower levels and reporting the information to higher levels for use in the Level IV Material Requirements Planning system 202 and Scheduling System 204.

The first interface is for Material On Hand displays. This interface involves getting data from Level II and making it available via CRT to the user. Additionally, the data collected is made available to the scheduling systems at Levels III and IV and to Production Reporting functions. The second interface involves making adjustments to in-plant inventories in Primary. This interface is between the Level III and Level II systems. Displays are provided by Level III to the user. The changes made are indicated to Level II for updating the inventories maintained by the plant as well as notifying the Transaction Log function of the changes. The third interface, the Transaction Log, involves collecting data regarding inventory transactions and making the data available to Level IV. Also, the Level III production reporting uses the data collected for shift and daily reports.

The Material On Hand function comprises collecting data on the R&B Level II computers and the Cutting and Casing Level II computers and copying the data up to Level III at regular intervals. The data includes information on tobacco inventories in bulkers, tanks and bales. No notification is required from Level II that the Material On Hand data is available. Level III acts independently from Level II in bringing the data to Level III. The data that is brought up to Level III replaces the old data each time. The data is then available for viewing by the users. If there is a problem with acquiring new data, PPMS notifies the user that the data being viewed is not up-to-date.

The inventory adjustment interface accesses three different inventory data storages maintained at Level II.

These three storages relate to the three types of items being used—Redried Leaf, Oriental Leaf, and Miscellaneous Materials. When the user requests data about a particular bale or item id, the program remotely accesses the Level II active system to find the information requested. After the data is displayed or modified, Level III Inventory Adjustment notifies Level II of the changes to be made. Changes are made on an individual bale or item id. Data is not accumulated for many changes and then sent all at once for updating the plant inventory files. Upon receiving the notification from Level III, Level II makes the appropriate changes to inventory. These changes are also reflected in the Transaction Log for notification to Level IV.

The Transaction Log is a chronological inventory event recorder that is used in the reporting function to produce shift and daily reports at Level III. It is the source for all data regarding Primary inventory movements for use by Level IV systems. Level III collects the data on a regular basis from the Primary Receiving System, Level II Receiving and Blending, and Level II Cutting and Casing. Each of these systems updates a Transaction Log file with data from material receipts, shipments, adjustments, and production histories. From the Transaction Log files created at the lower systems, Level III PPMS creates a single data storage. At the end of the production day, Level III schedules a batch job to send all of the day's transactions to Level IV. The data is also stored at Level III for a length of time before being deleted.

Batch/Run history data is collected at Level III of PPMS. The Run/Batch history is data accumulated for each processing run of Group Blended Strips, Final Blended Strips and Cut Filler. These reports contain indications of the amount of the product produced, the amount of each component consumed to produce the product, and the characteristics of the product including moisture levels, etc. After PPMS Level II has collected the required data for a production run, Level II notifies Level III of the availability of the Batch/Run History. Upon receiving the message of what file is to be brought from Level II to Level III, Level III will copy the file up. The data in the individual file is merged into an area Batch/Run History file. For example, the data coming from Level II is in a file for run 1, on line 2 in the Final Blended Strips area on the 8 shift of 1/28/87. No other runs' data is in this file. Once the data is at Level III, it is moved into the area file known as FBSBATCH.DAT. The data is maintained in this file for a predetermined time, such as three months. PPMS provides displays and hard copies of the Batch/Run History reports for the various areas of Primary Processing.

Inventory position reports are also provided. The inventory position reports are a set of shift and daily reports that indicate the various transactions that can occur to products produced in the Primary Processing area. The products covered in the reports are Group Blended Strip, Final Blended Strip, Cut Filler, and Casing. The transactions involved are beginning inventories in cans and bulkers and total weight, receipt of material, production, usage, material shipped, adjustments to inventory, and final inventory. The beginning and final inventories are based on snapshots of the material on hand data at the beginning of each shift. The remaining transactions are based on entries made into the Transaction Log from receiving, shipping, inventory adjustment and batch/run history routines. A variance is calculated by taking the beginning inventory, adding receipts and production, subtraction shipments and usage, and either adding or subtracting adjustments. The value gathered by this calculation is then compared to the final inventory. The difference between the calculated value and the snapshot value is then displayed as the variance for each material id.

A set of reports similar to the Inventory Position reports is provided for materials that are considered to be raw materials for a particular blending process. Raw materials are purchased materials for use in a process rather than materials produced by the plant, which are referred to as products. In the Receiving and Blending and Group Blended Strips areas, the raw materials could be redried and oriental tobaccos, for example. In Cutting and Casing, the raw materials would include, for example, flavorings. The transactions involved are beginning inventory, receipt of material, usage, material shipped, adjustments to inventory, and final inventory. The reports are provided on a shift and a daily basis. The beginning and final reports are based on snapshots of the material on hand data at the beginning of each shift. The remaining transactions are based on entries made into the Transaction Log from receiving, shipping, inventory adjustment and batch/run history routines. A variance is calculated by taking the beginning inventory, adding receipts, subtracting shipments and usage, and either adding or subtracting adjustments. The value gathered by this calculation is then compaed to the final inventory. The difference between the calculated value and the snapshot value is then displayed as the variance for each material id.

LEVEL II SOFTWARE

Receiving and Blending and Group Blended Strip

PPMS Level II has several functions which it is responsible for in the areas of Receiving and Blending and Group Blended Strip. The functions involve interfacing with the distributed processor control system (DPCS) on the node computers on Level I, with the Level II computers, with the PRS which carries out the receiving functions and with other functions with PPMS.

All of the PPMS software in this area runs on the dual 11/750 VAX computer configuration for the Receiving and Blending area comprising computers 170 and 171 shown in FIG. 2b. PPMS software runs at all times on both computers. The only difference in the activities from one computer to the other is that software running on the "active" machine will actually write data, when required, to the DPCS and Level III computers. The PPMS software running on the "idle" computer will receive the same inputs from these external systems but will not write to them unless the computer becomes the "active" machine.

It should be understood that the computer systems of Level II and Level I are based on a commercially available hardware system sold under the name Anatec and layered software system sold under the name CRISP by Anaconda Advanced Technology, Inc. The software used on these levels based on the CRISP software CRISP databases are stored in the memories of the Level II and Level I computers. In particular, the software run on the Level II computers uses CRISP 32 and the software on Level I uses CRISP 16.

When PPMS is providing data to Level I, it can occur in two ways. Each Level I computer maintains its own files in a CRISP database and also has disk storage specific to that computer. The first method involves PPMS writing data directly into the memories of the Level I computers using CRISP routines. In this case, PPMS is only able to place data on the "active" Level I computer. It is the responsibility of the level I software to assure that the data is transferred to the "idle" Level I computer.

The second method involves the use of the DECnet system 133 shown in FIG. 2a. DECnet is a Digital Equipment Corp. communication product which is used to allow PPMS to perform a disk to disk transfer to place data directly onto the disks of both Level I computers (active and idle) for a particular work center or group of work centers. The new data is written over any old data on the disk thereby eliminating the old data and updating the information available to the Level I systems. The data on the disk storage acts as a backup for the data stored in memory. That is, during normal processing procedures, CRISP database memory buffers in the Level I computers are updated only with the current run data and the next run data for the sections for which the computers are responsible. This information is used to run the processes. However, if some failure should occur with the updating, the information to carry out the runs is available in the disk memory for each computer and can be used to avoid the need to shut down the production line.

The following functions are performed by PPMS in the Receiving and Blending area:
1. Controlling the down load of recipes/operating instructions to the DPCS.
2. Controlling the down load of next run data and shift schedules to the DPCS.
3. Retrieving batch/run history data from the DPCS, updating plant inventories with the information, updating the transaction log file with the batch data, and supplying the Level III PPMS with historical data for scheduling and reporting purposes.
4. Updating the Redried Leaf and Oriental Leaf inventories with receipt, shipping and inventory adjustment data.
5. Collecting Redried and Oriental floor inventory data on a periodic basis for inventory status display purposes at Level III.

Each of these functions is described in more detail below in each of the system functional areas.

DATA COLLECTION

Recipe and Operating Instructions

All of the data collection involved with Recipe and Operating Instructions at this level is handled through external system interfaces. These interfaces will be discussed below.

SCHEDULING

All of the data collection involved with Scheduling at this level is handled through external system interfaces. These interfaces will be discussed below.

INVENTORY

There are two major parts to the handling of inventory data in Receiving and Blending. The first part involves the updaating of Redried Lead, Oriental Leaf, and Group Blended Strip floor inventories by way of receipts, shipments, inventory adjustments, and production runs. These updates are all handled via external system interfaces.

The second part involves the periodic collection of the floor inventories of Redried Leaf and the Oriental Leaf for use by Level III. This part is not considered to be part of an external system interface because it reads data from inventory files maintained by PPMS on the R & B Host computer.

Data is collected approximately every sixty seconds from the Redried Leaf inventory files and from the Oriental Leaf inventory file. The data is reconstructed into another file (RBMATONHAND.DAT). The RBMATONHAND.DAT file is copied to the Level III system every sixty seconds.

Only one copy of the RBMATONHAND.DAT file is maintained at any point in time. When a new set of data is ready to replace the old data, a temporary file is created. This file is renamed to RBMATONHAND.DAT when it is known that there are no programs accessing the old file. When the rename is done, the old file is deleted and the new file is renamed once again to being the first version of RBMATONNHAND.DAT.

BATCH/RUN HISTORY

Data for the R & B batch/run history is collected from three sources. The first source is a data file provided by the Level I computers at the end of a run. The software collects the data on the Level I computers and brings the file up to the R & B Host computer at Level II. When the file has reached the R & B Host computer, the Level I software notifies PPMS software that a batch/run history is available for use by PPMS.

Once OPPMS receives notification that a batch/run is available, the PPMS Batch/run software notifies the Scheduling software that a particular run has ended. In addition, the Batch/run software notifies the PPMS Inventory Update software about the batch/run.

The software then waits for the Scheduling and Inventory Update functions to indicate that they are done with the Batch/run history.

After the Batch/run software has been notified that the other PPMS functions are through with the particular batch/run, the Level III system is notified that a batch/run is available for transmission from Level II.

EXTERNAL SYSTEMS INTERFACE

Recipe and Operating Instructions DPCS Interface

PPMS is responsible for providing the R & B Level I systems with the required recipe and operating instructions for making Group Blended Strip runs. PPMS provides recipe and operating instructions to the DPCS in two ways. The first way is based on a next run data request from the control system. The second method is based on notification from Level III that there is a new set of recipe and operating instruction data for the work center. In the first case, when PPMS is notified by the DPCS that there is a need for next run data and after the PPMS has determined what the next run should be for the particular work center, the PPMS will check its Recipe File and Operating Instructions File to make sure that the recipe called for by the schedule exists on the Level II computer. The key to the files is a combination of blend code and spec version.

After it has been verified that the Level II computer has the required data, PPMS will write through CRISP calls the recipe/operating instructions into the next run area of the memory buffer. PPMS will then set a flag associated with this memory buffer to indicate to the control system that PPMS has completed its down load of data to satisfy the next run request.

Under this first method, no data is written to the Level I computer disk storage, only to the memory buffer. Level I does not take this data and write it out to disk. To satisfy the need to have recipe and operating instructions on the Level I for backup purposes, the second procedure mentioned below is used.

In this second method, Level II PPMS receives notification from Level III that there is now recipe and/or operating instruction data for the work area (i.e. R&B/GBS). Level II will bring a copy of the recipe and operating instructions maintained at Level III down to Level II. Level II PPMS then will copy the newest data down to Level I as a set with the unchanged data for other sets of recipes and operating instructions. When moving the data from Level III to Level II and Level II to Level I, DECnet file transfers are used to move the data in a disk to disk transfer. The new files are written directly over the old files so that the information on the Level I disks is updated.

LEVEL III INTERFACE

The Level II software will receive notification from Level III of availability of a revised set of recipes and operating instructions in the form of new or revised records for the Recipe and/or the Operating Instruction File. The notification will be in the form of a message through the Network Sender/Receiver software. Upon receiving the message, Level II will issue a copy command to copy the files down to Level II. The files have already been created on Level III from data in the FMS database and from the plant owned operating instruction database. The data is then ready to be supplied to Level I.

SCHEDULING

DPCS Interface

The Level II PPMS Scheduling function provides run data to the Level I system in the form of next run data and shift schedules. The next run data is used to prepare the particular line for the next run. The shift schedule is a list of the next eight to ten runs that are scheduled for a particular line.

The Level II PPMS software monitors certain flags in the Level I computer memory which will indicate when a particular line has moved data in its next run buffer to its current run buffer, therefore leaving space for PPMS to provide the next run's data.

Upon receiving the notification, Level II PPMS checks to make sure that the runs it expects to be in the particular memory buffers match what are in the buffers. If there are any discrepancies between expected and actual run numbers, blend code or blend revision, PPMS will not down load any data to Level I until the schedule has been corrected or Level I is corrected. This situation is what is referred to as a "line lock" condition. It does not mean that the line is physically stopped from running. It only means that PPMS has recognized a discrepancy and does not want to down load data that is possibly erroneous until the scheduler has corrected the situation. The scheduler in this case may be in the form of manual intervention.

Providing everything checks out satisfactorily, PPMS will proceed to down load to Level I the next run data. This process includes validating that the required recipe and operating instructions are available and calling a recipe function routine to place the blend/version of the recipe specified in the schedule into the next run buffer.

In the process of down loading the next run data, Level II PPMS will utilize the schedule weight of the run and the recipe for the run to create a list of the required poundage for each item on the recipe. These poundages are then checked against inventory to make sure that enough material is available for use in the run. If enough material is found, PPMS will commit the inventory required so that it is considered unusable for further runs. If there is not enough availabe, PPMS will print out a message to warn production personnel of the lack of material. In each case, however, the required data for next run and recipe will still be down loaded to Level I.

When the next run data for the schedule and the recipe/operating instructions have been down loaded to Level I, PPMS then notifies Level I that the next run data is in the database and available for use. PPMS will then proceed with updating the shift schedule information at Level I for the work center with the next eight to ten runs. As discussed above, Level I maintains a shift schedule for backup purposes. In the event that this information is needed, it can be displayed on screen for the user to review.

Another possibility for Level I to receive shift schedule data involves the committing of a new schedule for a particular work center. When a new or revised schedule is committed for Level III to Level II, Level II proceeds to down load the next eight to ten runs for the work center into the work center's Level I database. The down load of this new/revised schedule is not dependent on a run having been completed in the work center. The only requirement is notification from Level III of a new committed schedule. The handling of this commit function is discussed in the next section.

LEVEL III INTERFACE

Level III PPMS is the source of the schedule for each R&B work center. Level II PPMS is notified that a new/revised schedule is to be incorporated via the Network Sender/Receiver communications software. A message is placed into the network indicating which work center is to receive the schedule. The new schedule data is then copied down from Level III to Level II.

Each Level II computer (active and idle) is notified separately of the schedule availability. Each makes its own copy from the Level III data. The new work center schedule data is constructed on Level II such that is replaces, in whole, the old schedule at Level II. This committing of a new schedule happens independently of what is happening at Level I.

Once the new schedule is at Level II, the data is supplied to Level I in the manner described in the previous section.

INVENTORY

DPCS Interface

The interface to Level I data is actually an indirect interface. Data collected by the Batch/Run History function from the Level I software is used by the Inventory Update function to modify the in-plant inventories of Redried Leaf and Oriental Leaf as well as any Group Blended Strip floor tobacco that may be used in a production run.

Notification of an available batch/run history is sent in a message through mailbox communications. Mailboxes are nothing more than a method of having a program place message in a large storage area and having a program read these messages in that order they are received and performing some action based on the message received.

The data supplied in the batch/run with regard to Redried Leaf involves consumption data on individual bales. Information dealing with actual pounds consumed and remnant weight is married with a bale bar code number to determine if a bale should be removed from inventory or if its data should be revised. The information is used to update, for example, the batch/run data with information pertaining to weight errors between actual consumed and remaining weight and the weight the bale was received or last weighed at.

Additionally, the individual bale is used to update inventory data representing the amount of particular tobacco type available. This procedure also handles modifying the amount of tobacco which has been reserved or committed to runs in R&B.

Another interface that utilizes inventory data is the Grade Entry Level I-Level II interface. Each Redried bale is wanded with a bar code reader at each line's grade entry station. At this time, a PPMS Level II program detects that a bar code is in the database. This signals that a request is outstanding for PPMS to identify the bale for Level I.

PPMS Level II will take the barcode and look for the bale's inventory information in the inventory file. If the bale is found in inventory, a comparison of its grade/belt/crop year/cell code will be made against each recipe item that is being used on the line in question. If a match is found, PPMS will notify Level I as to which item the bale matches. If no match is found, PPMS will signal Level I that the bale is on file but does not match any of the recipe items.

In the event that the bale is not on file, PPMS will provide the proper signal to Level I that the bale's data could not be found.

PRS INTERFACE

Each time a bale of tobacco is received, shipped or adjusted, the programs through which the user is interfacing with the receiving system have the responsibility of passing to the PPMS Level II Inventory Update program the data associated with the bale in question.

The data is passed to both the idle and active R&B host computers via the Network communications software. The data is passed in the form of a message buffer. Along with information pertaining to the bale's barcode, grade, belt, crop year, cell code and weight, the data also includes information about the bale's receipt or shipment.

A flag is included in the message which indicates what is to be done with the data. It may indicate that the bale is to be added, changed, or deleted.

The data is passed to each system as each bale is recognized at the docks and the in-plant inventory is immediately updated. This happens in a real-time mode as opposed to waiting for the shipment to be completely received or shipped because of the need to inform the grade entry stations about a bales' identifiers when the bale is being prepared for consumption. It is possible for a bale to go directly from the docks to grade entry without being stored.

The data about the individual bale is also used to update the inventory that is based on material id.

BATCH/RUN HISTORY

DPCS INTERFACE

At the completion of a batch/run, the Level I system will collect all of the run data that is present on the node computers at Level I. Level I is responsible for transferring the data from the node computers to the Level II host computers. This is accomplished by file transfers via DECnet communications. Level I must get a copy of the batch/run data up to each of the R & B host computers.

Once the batch/run file is located on each of the R&B host computers in the form expected by Level II PPMS, Level I software will notify PPMS level II of the file availability with a message deposited in a message storage urea known as a mailbox.

Upon reading the message, Level II PPMS will proceed to process the file.

LEVEL III INTERFACE

After processing of the batch/run file is completed by all Level II programs, Level II PPMS will notify Level III PPMS of the data availability. This is done using the Network Sender/Receiver software. The message passed includes the name and location of the file to be copied.

REPORTING

No reports are generated at the R & B Level II system. All hard copy and video display reports are handled at Level III.

FINAL BLENDED STRIP

PPMS has several functions which it is responsible for in the area of Final Blended Strip (FBS). The functions involve interfacing with the DPCS computers, with the Level III computers, with the Primary Receiving computer and with other functions within PPMS.

All of the PPMS software in this area runs on the dual 11/750 VAX computer configuration for the Casing and Cutting area comprising the C&C host computers 172 and 173 in FIG. 2b. PPMS software runs at all times on both computers. The only difference in the activities from one computer to the other is that software running on the "active" machine will actually write data, when required, to the DPCS and Level III computers. The PPMS software running on the "idle" computer will receive the same inputs from these external systems but will not write to them unless the computer becomes the "active" machine. When PPMS is providing data to Level I, it can occur in two ways. The first method involves PPMS writing data directly into the computer memory which stores Level I databases based on the CRISP system provided by Anatek. In this case, PPMS is only able to place data on the "active" Level I computer. It is the responsibility of the Level I software to assure that the data is transferred to the "idle" Level I computer.

The second method involves the use of DECnet, to place data onto the disks of both Level I computers (active and idle) for a particular work center or group of work centers.

The following functions are performed by PPMS in the Final Blended Strip area:
1. Controlling the down load of recipes/operating instructions to the DPCS, 2. Controlling the down load of next run data and shift schedules to the DPCS.
3. Retrieving batch/run history data from DPCS, updating plant inventories with the information, updating the transaction log file with the batch data, and supplying the Level III PPMS with historical data for scheduling and reporting purposes.
4. Updating the miscellaneous material inventories with receipt, shipping and inventory adjustment data.
5. Collecting miscellaneous tobacco floor inventory data, Group Blended Strip bulker data and Final Blended Strip bulker data on a periodic basis for inventory status display purposes at Level III.

Each of these functions are described in more detail below in each of the system functional areas.

DATA COLLECTION

Recipe and Operating instructions

All of the data collection involved with Recipe and Operating Instructions at this level is handled through external system interfaces.

SCHEDULING

All of the data collection involved with scheduling at this level is handled through external system interfaces.

INVENTORY

There are two major parts to the handling of inventory data in Final Blended Strip. The first part involves the updating of miscellaneous tobacco and Final Blended Strip floor inventories by way of receipts, shipments, inventory adjustments, and production runs. These updates are all handled via external system interfaces.

The second part involves the periodic collection of the floor inventories of miscellaneous tobacco and various bulker inventories for use by Level III. This part is not considered to be part of an external system interface because it reads data from inventory files maintained by PPMS on the C&C host computers or the data is collected from data storage maintained on the C&C host computers without the need to communicate with the Level I computer that the data is being collected.

Data is collected approximately every sixty seconds from the Miscellaneous Material Inventory file (MISCMATINV.DAT). The data is reconstructed into another file (CCMATONHAND.DAT). The CCMATONHAND.DAT file is copied to the Level III system every sixty seconds.

The operation of collecting material inventory data for Final Blended Strip form the MISCMATINV.DAT file is handled by the same program that handles the data gathering for the Casing and Cutting area. The data from these areas is placed into the same CCMATONHAND.DAT file.

Additionally, PPMS reads the CRISP databases maintained on the C&C host computer on a periodic basis to collect current information about the Group Blended Strip bulkers and the Final Blended Strip bulkers used to store the group blended strips and the final blended strips, respectively. This data is also placed in the CCMATONHAND.DAT file.

Only one copy of the CCMATONHAND.DAT file is maintained at any point in time. When a new set of dat is ready to replace the old data, a temporary file is created. This file is renamed to CCMATONHAND.DAT when it is known that there are no programs accessing the old file. Once the rename is done, the old file is deleted and the new file is renamed once again to being the first version of CCMATONHAND.DAT.

BATCH/RUNHISTORY

Data for the FBS batch/run history is collected from two sources. The first source is a data file provided by the DPCS at the end of a run. The DPCS has collected the data on the Level I node 11/44 computers 178, 179 and has brought the file up to the C&C host. When the file has reached C&C host, DPCS software notifies PPMS software that a batch/run history is available for use by PPMS.

Once PPMS receives notification that a batch/run is available, the PPMSs Batch/run software notifies the Scheduling software that a particular run has ended. In addition, the Batch/run software notifies the PPMS Inventory Update software about the batch run. The software then waits for the Scheduling and Inventory Update functions to indicate that they are done with the batch/run history.

After the Batch/run software has been notified that the other PPMS functions are through with the particular batch/run, the Level III system is notified that a batch/run history is available for transmission to the Level III.

EXTERNAL SYSTEMS INTERFACE

Recipe and Operating Instructions DPCS Interface

PPMS is responsible for providing the FBS Level I systems with the required recipe and operating instructions for making Final Blended Strip runs. PPMS provides recipe and operating instructions to the control system in two ways. The first way is based on a next run data request from the control system. The second method is based on notification from Level III that there is a new set of recipe and operating instruction data for the work center.

In the first case, when PPMS is notified by the DPCS that there is need for next run data and after the PPMS has determined what the next run should be for the particular work center, the PPMS will check its recipe files (FBSRECIPE.DAT) and operating instructions file (FBSOI.DAT) to make sure that the recipe called for by the schedule exists on the Level II computer. The Key to the files is a combination of blend code and spec version.

After it has been verified that the Level II computer has the required data, PPMS will write through CRISP calls the recipe/operating instructions into the next run area of the CRISP database which is also referred to as the next run buffer of the Level I computer. PPMS will then set a flag in the CRISP database in the Level I computer memory to indicate to the control system that PPMS has completed its down load of data to satisfy the next run request.

Under this first method, no data in written to the Level I computer disk storage, only to the CRISP database. Level I does not take this data and write it out to disk. To satisfy the need to have recipe and operating instructions on the Level I for backup purposes, the second procedure mentioned above is used.

In this second method, Level II PPMS receives notification from Level III that there is new recipe and/or operating instruction data for the work area (i.e. R & B/GBS). Level II will bring a copy of the recipe and operating instructions maintained at Level III down to Level II. Level II PPMS then will copy the newest data down to Level I as a set with the unchanged data for other sets of recipes and operating instructions. When moving the data from Level III to Level II and Level II to Level I, DECnet transfers are used to move the data.

LEVEL III INTERFACE

Level II software will receive notification from Level III of availability of a revised set of recipes and operating instructions. The notification will come in the form of a message through the Network Sender/Receiver software.

Upon receiving the messages, Level II will issue a copy command to bring the files down to Level II. The files have already been created on Level III from data in the FMS database and from the plant-owned operating instruction database. The data is then ready to be supplied to Level I.

SCHEDULING

DPCS Interface

The Level II PPMS Scheduling function provides run data to the Level I system in the form of next run data and shift schedules. The next run data is used to prepare the particular line for the next run. The shift schedule is a list of the next eight to ten runs that are scheduled for a particular line.

The Level II PPMS software monitors flags in the CRISP database which are associated with individual FBS lines (there may be a plurality of such lines in any one plant) and indicate when the associated line has moved its data from its next run buffer to its current run buffer, therefore leaving space for PPMS to provide the next run's data.

Upon receiving the notification, Level II PPMS will check to make sure that the runs it expects to be in the particular CRISP buffers match what are in the buffers. If there are any discrepancies between expected and actual run numbers blend/revision codes, PPMS will not down load any data to Level I until the schedule has been corrected or Level I is corrected. This situation is what is referred to as a "line lock" condition. It does not mean that the line is physically stopped from running. It only means that PPMS has recognized a discrepancy and does not want to down load data that is possibly erroneous until the scheduler has corrected the situation.

Providing everything checks out satisfactorily, PPMS will proceed to down load to the Level I CRISP database the next run data. This process includes validating that the required recipe and operating instructions are available and calling a Recipe function routine to place the blend/version of the recipe specified in the schedule into the next run buffer.

When the next run data for the schedule and the recipe/operating instructions have been down loaded to Level I, PPMS then notifies Level I that the next run data is in the CRISP database and available for use. PPMS will then proceed with updating the CRISP shift schedule database for the work center with the next eight to ten runs.

Another possibility for level I to receive shift schedule data involves the committing of a new schedule for a particular work center. When a new or revised schedule is committed form Level III to level II, Level II proceeds to down load, via CRISP routines, the next eight to ten runs for the work center into the work center's Level I CRISP database. The down loading of this new/revised schedule is not dependent on a run having completed in the work center. The only requirement is notification from Level III of a newly committed schedule. The handling of this commit function is discussed in the next section.

LEVEL III INTERFACE

Level III PPMS is the source of the schedule for each FBS work center. Level II PPMS is notified that a new/revised schedule is to be incorporated via the Network sender/Receiver communications software. A message is placed into the network indicating which work center is to receive the schedule. The new schedule data is then copied down from Level III to Level II.

Each Level II computer (active and idle) is notified separately of the schedule availability. Each makes its own copy from the Level III data. The new work center schedule data is constructed on Level II such that it replaces, in whole, the old schedule at Level II. This committing of a new schedule happens independently of what is happening at Level I.

Once the new schedule is at Level II, the data is supplied to Level I in the manner described in the previous section.

INVENTORY

DPCS Interface

The interface to Level I data is actually an indirect interface. Data collected by the Batch/Run History function from the Level I software is used by the Inventory Update function to modify the in-plant miscellaneous tobacco inventory as well as any FBS floor tobacco that may be used in a production run.

Notification of an available batch/run history is sent in a message through mailbox communication.

LEVEL III INTERFACE

Level II PPMS is responsible for collecting miscellaneous tobacco floor inventory status approximately every sixty seconds. There is no message transmission involved with Level III in this function. Level III copies the data up independent of the gathering of the data at Level II.

PRS INTERFACE

Final blended strips produced in a plant may be used in the cutting and casing line of that plant or may be shipped to another plant for use. Likewise, final blended strips may be received from another plant. Each time FBS is received, shipped or adjusted the programs through which the user is interfacing with PRS have the responsibility of passing to the PPMS Level II Inventory Update programs the data associated with the material in question. The message is passed via the Network Sender/Receiver software.

BATCH/RUN HISTORY

DPCS Interface

At the completion of a batch/run, the Level I systems will collect all of the run data that is present on the Level I computers. Level I is responsible for transferring the data from the Level I computers to the Level II host computers. This is accomplished by file transfers via DECnet communications. Level I must get a copy of the batch/run data up to each of the C&C hosts.

Once the batch/run file is located on each of the C&C hosts in the form expected by Level II PPMS, Level I software will notify PPMS Level II of the file availability with a message deposited in a mailbox.

LEVEL III INTERFACE

After processing of the batch/run file is completed by all Level II programs, Level II PPMS will notify Level III PPMS of the data availability. This is done using the Network Ssender/Receiver software. The message passed includes the name and location of the file to be copied.

REPORTING

There are no reports generated at the C&C Level II system. All hard copy and video display reports are handled at Level III.

CASING AND CUTTING/CUT FILLER STORAGE

PPMS has several functions which it is responsible for in the area of Casing and Cutting/Cut Filler Sstorage. The functions involve interfacing with the DPCS computers, with the Level III computers, with the Primary Receiving computer and with other functions within PPMS.

All of the PPMS software in this area runs on the host computers 172, 173 which are in the form of a dual 11/750 VAX computer configuration for the Casing and Cutting area. PPMS software runs at all times on both computers. The only difference in the activities from one computer to the other is that software running on the "active" machine will actually write data, when required, to the DPCS and Level III computers. The PPMS software running on the "idle" computer will receive the same inputs from these external systems but will not write to them unless the computer becomes the "active" machine.

When PPMS is providing data to Level I, it can occur in two ways. The first method involves PPMS writing data directly into the CRISP Level I databases. In this case, PPMS is only able to place data on the "active" Level I computer. It is the responsibility of the Level I software to assure that the data is transferred to the "idle" Level I computer.

The second method involves the use of DECnet to place data onto the disks of both Level I computers (active and idle) for a particular work center or group of work centers.

The following functions are performed by PPMS in the Casing and Cutting/Cut Filler Storage area:
1. Controlling the down load of recipes/operating instructions to the DPCS.
2. Controlling the down load of next run data and shift schedules to the DPCS.
3. Retrieving batch/run history data from the DPCS, updating plant inventories with the information, updating the transaction log file with the batch data, and supplying the Level III PPMS with historical data for scheduling and reporting purposes.
4. Updating the miscellaneous material inventories with receipt, shipping and inventory adjustment data.
7. Collecting miscellaneous tobacco floor inventory data, Cut Filler bulker data, and casing tank dataon a periodic basis for inventor status display purposes at Level III.

Each of these functions are described in more detail below in each of the system functional areas.

DATA COLLECTION

Receipe and Operating Instructions

All of the data collection involved with Recipe and Operating Instructions at this level is handled through external system interfaces.

SCHEDULING

All of the data collection involved with Scheduling at this level is handled through external system interfaces.

INVENTORY

There are two major parts to the handling of inventory data in Casing and Cutting/Cut Filler Storage. The first part involves the updating of miscellaneous tobacco and Cut Filler floor inventories by way of receipts, shipments, inventory adjustments, and production runs. These updates are all handled via external system interfaces. The second part involves the periodic collection of the floor inventories of miscellaneous tobacco and various bulker and tank inventories for use by Level III. This part is not considered to be part of an external system interface because it reads data from inventory files maintained by PPMS on the C&C host or the data is collected from data storage maintained on the C&C host computers without the need to communicate with the Level I computer that the data is being collected.

Data is collected approximately every sixty seconds from the Miscellaneous Material inventory file (MISCMATINV.DAT). The data is reconstructed into another file (COMATONHAND.DAT). The CCMANTONHAND.DAT file is copied to the Level III system every sixty seconds.

The operation of collecting material inventory data for Casing and Cutting/Cut Filler Storage from the MISCMATINV.DAT file is handled by the same program that handles the data gathering for Final Blended Strip area. The data from all of the above mentioned areas is placed into the same CCMATONHAND.DAT filed.

Additionally, PPMS reads the CRISP databases maintained on the C&C host computer on a periodic basis to collect current information about the Cut Filler bulkers and the casing tanks used to distribute casing during the Casing and Cutting operation. This data is also placed in the CCMATONHAND.DAT file.

Only one copy of the CCMATONHAND.DAT file is maintained at any point in time. When a new set of data is ready to replace the old data, a temporary file is created. This file is renamed to CCMATONHAND-.DAT when it is known that there is no programs accessing the old file. Once the rename is done, the old file is deleted and the new file is renamed once again to being the first version of CCMATONHAND.DAT.

Data for the C&C batch/run history is collected from two sources. The first source is a data file provided by the DPCS at the end of a run. The DPCS has collected the data on the Level I computers and has brought the file up to the C&C host computer on Level II. When the file has reached the C&C host, DPCS software notifies PPMS software that a batch/run history is available for use by PPMS. Once PPMS receives notification that a batch/run is available, the PPMS Batch/run software notifies the Scheduling software that a particular run has ended. In addition, the Batch run/software notifies the PPMS Inventory Update software about the batch- /run. The software then waits for the Scheduling and Inventory Update functions to indicate that they are done with the batch/run history.

After the Batch/run software has been notified that the other PPMS functions are through with the particular batch/run, the Level III system is notified that a batch/run is available for transmission to the Level III.

EXTERNAL SYSTEMS INTERFACE

Recipe and Operating Instructions DPCS Interface

PPMS is responsible for providing the C&C Level I systems with the required recipe and operating instructions for making Casing and Cutting runs. PPMS provides recipe and operating instructions to the control system in two ways. The first way is based on a next run data request from the control system. The second method is based on notification from Level III that there is a new set of recipe and operating instruction data for the work center.

In the first case, when PPMS is notified by the DPCS that there is a need for next run data and after the PPMS has determined what the next run should be for the preiodic work center, the PPMS will check its recipe files (CNCRECIPE.DAT) and operating instruction file (CNOCOI.DAT) to make sure that the recipe called for by the schedule exists on the Level II computer. The key to the files is a combination of blend code and spec version.

After it has been verified that the Level II computer has the required data, PPMS will write through CRISP calls the recipe/operating instructions into the next run area of the CRISP database. PPMS will then set a flag in the CRISP database to indicate to the control system that PPMS has completed its down load of data to satisfy the next run request.

Under this first method, no data is written to the Level I computer disk storage, only to the CRISP database. Level I does not take this data and write it out to disk. To satisfy the need to have recipe and operating instructions on the Level I for backup purposes, the second procedure mentioned above is used.

In this second method, Level II PPMS receives notification from Level III that thereis new recipe and/or operating instruction data for the work area (i.e. C&C). Level II will bring a copy of the recipe and operating instructions maintained at level III down to level II. Level II PPMS then will copy the newest data down to Level I as a set with the unchanged data for other sets of recipes and operating instructions. When moving the data from Level III to Level II and from Level II to Level I, DECnet file transfers are used to move the data.

LEVEL III INTERFACE

The Level II software will receive notification from Level III of availability of a revised set of recipes and operating instructions. The notification will come in the form of a message through the Network Sender/Receiver software.

Upon receiving the message, Level II will issue a copy command to bring the files down to Level II. The files have already been created on Level III from data in the FMS database and from the plant-owned operating instruction database. The data is then ready to be supplied to Level I.

SCHEDULING

DPCS Interface

The Level II PPMS Scheduling function provides run data to the Level I system in the form of next run data and shift schedules. The next run data is used to prepare the particular line for the next run. The shift schedule is a list of the next eight to ten runs that are scheduled.

The Level II PPMS software monitors flags in the CRISP data base which are associated with individual C&C lines and indicate when a particular line has moved data from its next run buffer to its current run buffer, therefore leaving space for PPMS to provide the next run's data.

Upon receiving the notification, Level II PPMS will perform a number of checks to make sure that the runs it expects to be in the particular CRISP buffers match what are in the buffers. If there are any discrepancies between expected and actual run numbers, blend code or blend revision, PPMS will not down load any data to Level I until the schedule has been corrected or Level I is corrected. This situation is what is referred to as a "line lock" condition. It does not means that the line is physically stopped from running. It only means that PPMS has recognized a discrepancy and does not want to down load data that is possibly erroneous until the scheduler has corrected the situation.

Providing everything checks out satisfactorily, PPMS will proceed to down load to the Level I CRISP database the next run data. This process includes validating that the required recipe and operating instructions are available and calling a Recipe function routine to place the blend/version of the recipe specified in the schedule into the next run buffer.

When the next run data for the schedule and the recipe/operating instructions have been down loaded to Level I, PPMS then notifies Level I that the next run data is in the CRISP database and available for use. PPMS will then proceed with updating the CRISP shift schedule display database for the work center with the next eight to ten runs.

Another possibility for Level I to receive shift schedule data involves the committing of a new schedule for a particular work center. When a new or revised schedule is committed form Level III to Level II, Level II proceeds to down load, via CRISP routines, the next eight to ten runs for the work center into the work center's level I CRISP database. The down loading of this new/revised schedule is not dependent on a run having completed in the work center. The only requirement is notification from Level III of a newly committed schedule. The handling of this commit function is discussed in the next section.

LEVEL III INTERFACE

Level III PPMS is the source of the schedule for each C&C work center. Level II PPMS is notified that a new/revised schedule is to be incorporated via the Network Sender/Receiver communications software. A message is placed into the network indicating which work center is to receive the schedule. The new schedule data is then copied down from Level III to Level II.

Each Level II computer (active and idle) is notified separately of the schedule availability. Each makes its own copy from the Level III data. The new work center schedule data is constructed on Level II such that it replaces, in whole, the old schedule at Level II. This committing of a new schedule happens independent of what is happening at Level I.

Once the new schedule is at Level II, the data is supplied to Level I in the manner described in the previous section.

INVENTORY

DPCS Inventory

The interface of Level I data is actually an indirect interface. Data collected by the Batch/Run History function from the Level I software is used by the in-plant miscellaneous tobacco Update function to modify the in-plant miscellaneous tobacco inventory as well as any CFS floor tabacco that may be used in a production run.

Notification of an available batch/run history is sent in a message through mailbox communications.

LEVEL III INTERFACE

Level II PPMS is responsible for collecting miscellaneous tobacco floor inventory status approximately every sixty seconds. There is no message transmission involved with Level III in this function. Level III copies the data up independent of the gathering of the data at Level II.

PRS INTERFACE

Each time Top Dressing and CFS is received, shipped or adjusted, the programs through which the user is interfacing with PRS have the responsibility of passing to the PPMS Level II Inventory Update programs the data associated with the material in question.

The message is passed via the Network Sender/Receiver software. The data in the message indicates either a file needs to be copied from PRS and be processed or data is included about a particular tote tank of Top Dressing. In both cases, the data involves updating the amount of a particular item id in inventory. Additionally, the Top Dressing tanks are tracked like Redried Leaf bales (by barcode). Data received on tote tanks of Top Dressing is kept at the container level, as well as at the item id level.

BATCH/RUN HISTORY

DPCS Interface

At the completion of a batch/run, the Level I system will collect all of the run data that is present on the Level I computers. Level I is responsible for transferring the data from the Level I computers to the Level II host computers. This is accomplished by file transfers via DECnet communications. Level I must get a copy of the batch/run data up to each of the C&C host.

Once the batch/run file is located on each of the C&C hosts in the form expected by Level II PPMS, Level I software will notify PPMS Level II of the file availability with a message deposited in a mailbox.

Upon reading the message, Level II PPMS will proceed to process the file.

LEVEL III INTERFACE

After processing of the batch/run file is completed by all Level II programs, Level II PPMS will notify Level III PPMS of the data availability. This is done using the Network Sender/Receiver software. The message passed includes the name and location of the file to be copied.

REPORTING

There are no reports generated at the C&C Level II system. All hard copy and video display reports are handled at Level III.

MAKING AND PACKING

The scheduling and specification information which is married on the Level III Plant Manager System is also passed to the Making and Packing Management system (MPMS) 230 discussed above with reference to FIG. 2. The MPMS communicates with the Plant management system through the Ethernet communication link shown in FIG. 2 and stores a list of approximately one week of scheduled runs for the M&P complexes. The specs for the current and next scheduled run for each complex are sent to the individual complexes. Each time a run is completed, the CATC notifies the MPMS and a new set of specs for the next run is sent to that complex.

Figure 13:
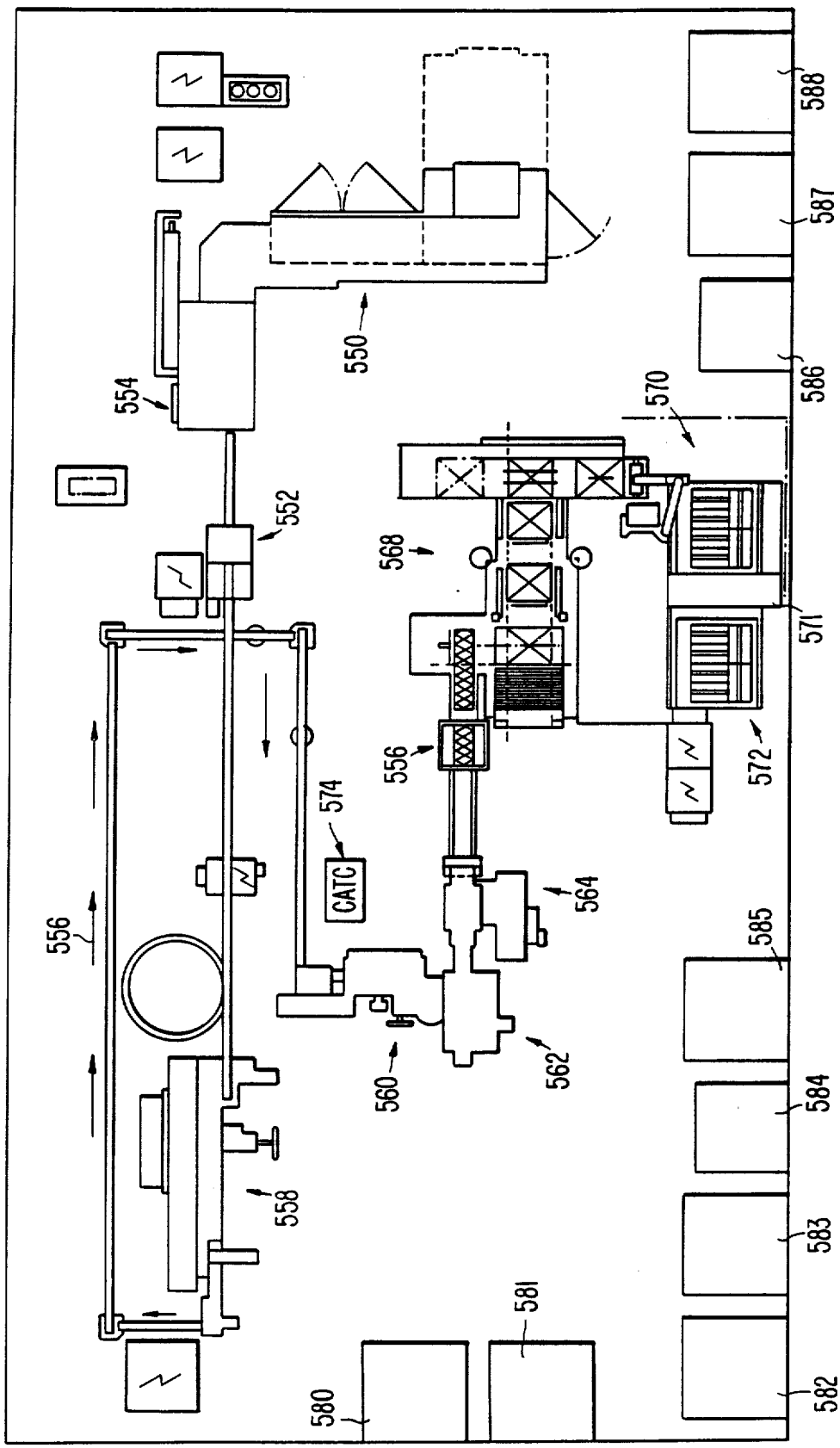
FIG. 13. shows a detailed view of one making and packing complex.

As discussed above with reference to FIG. 1, each M&P complex includes a rod making area 118, a packing area 120, a carton packing area 122, a case packing area 124 and a pelletizing area 126. FIG. 13 shows in top plan view the layout and details of one making and packing complex. As discussed above, there can 72 or more making and packing complexes in one plant. Each making and packing complex operates autonomously as a miniplant. The making and packing complex as shown in FIG. 13 has a rod making area with a rod making machine 550 and a filter tip attaching machine 554. The rod making machine is a conventional device manufactured by Hauni-Werke Koerber & Co. KB of W. Germany and sold under the tradename "Protos." The filter tip attachment machine 554 is also a conventional piece of equipment know under the trade name "Max 80" and sold by Hauni-Werke. The filter tipper 554 sends the completed cigarette rod through an inspection station 552. From the inspection station 552, the cigarettes are sent to a vertical spiral accumulator 556 which is manufactured and sold by the G.D. company under the designation S-90. The accumulator 556 provides short term storage of the cigarette rods so as to provide a buffer between the rod making area and the packing area. The storage facility 556 feeds a package making machine 558 which is a conventional G.D. packer sold under the designation X1 roll packer. The packages of cigarettes go to a package wrapper 560 and then to a cartoner 562. The package wrapper and cartoner are sold as a unit by G.D. under the designation 4350/Pack-s complex. For certain export products, it is necessary to have the cartons overwrapped. An overwrapper 564 is provided for this purpose. The overwrapper is also a conventional G.D. product. A vertical carton accumulator 566 receives the cartons for temporary storage as a buffer between the cartoner and the casepacker 568. The accumulator and the casepacker 568 are conventional pieces of equipment sold by Focke & Co. The cartons are taken from the accumulator 566 and cased in case packing machine 568. The finished cases are palletized by the palletizer 570, which is also conventional and sold by Focke & Co. The palletizer stacks the finished cases on pallets to be removed by the automatic guided vehicle system.

Each piece of equipment discussed above relative to FIG. 13 is conventional and includes an individual computer control system. Although the equipment is conventional, the layout and interconnection of the pieces as shown in FIG. 13 is not conventional. The layout was selected to facilitate operator control and observation of the equipment as it is running. Also, the layout shown reduces noise transmission throughout the factory since the noise emitting portions of the machines are oriented to muffle sound.

The control systems on the conventional equipment are also conventional. These control systems are modified to make them compatible with the MPMS computer and are connected to a CATC 574 to receive data for controlling the runs. The CATC 574 includes a display screen to be viewed by an operator of the complex.

Each complex has one CATC and there is one filter making machine for each complex. The filter makers are grouped together in an area separate from the complexes. There is one CATC for every 18 filter markers.

Each complex also has a plurality of AGV accessible locations for storing non-tobacco materials to be used at the complex as well as for storing rejects and debris to be removed by the AGV.

The tobacco materials are delivered through a pneumatic delivery system directly to the rod making machine 550. From the rod making area, the finished cigarette rods are delivered through a conveyor to the package making machine 558 and from the package making machine 558, the packages are delivered through a conveyor to the package wrapping machine 560. The conveyors for carrying the product are configured to enable the machines to be laid out in the configuration shown in FIG. 13 with the rod making machine and the package making machine forming substantially an L-shape and the package wrapping machine 560 perpendicular to the package making machine 558. The filters are delivered pneumatically to the tipping area 554.

There are also two pallet locations 571 and 572. The pallet location 571 is nearer the palletizer, has one vertically movable pallet platform which holds one pallet to be filled by the palletizer. This pallet is filled with the pallet platform in the lower position. The other pallet location 572 has two vertically spaced pallet platforms. The upper platform holds a filled pallet to be taken away by the AGV and the lower pallet platform holds an empty pallet brought by the AGV. When the pallet on the platform in position 571 is filled, it is lifted by an elevator mechanism and moved sideways onto the platform in the upper position of location 572 by a conveyor. The platform in location 571 is then lowered and the empty pallet is moved by conveyor onto the platform in location 571 to be filled by the palletizer.

As soon as a full pallet is placed in the upper position of location 572, a sensor determines the presence of the full pallet and notifies the AGV management system directly that a full pallet is ready to be delivered to the finished goods area. The sensor signal is coded to indicate to the AGV management system the location of the full pallet and the AGV management system also causes the AGV control system to bring an empty pallet to the complex. It takes about 40 minutes to fill a pallet so that there is ample time for the AGV to bring an empty pallet and remove the full pallet before the next pallet is full.

The storage positions 580–588 hold items such as labels, foil, film, cartons, scrap, cases, paper, etc. which may be used by the various machines in the complex. The storage locations are at the periphery of the complex so that they are easily reached by the AGVs. The storage locations may be in communication with the various machines in order to provide the non-tobacco materials directly to the machines, or an operator can hand feed the machines as the need arises. In either case, when the supply of non-tobacco materials becomes low, a signal is sent through the CATC to the factory service management system to send the appropriate material to the complex. In the case that the operator feeds the machines, the signal may be manually input to the CATC. Otherwise, the signal may be automatically sent based on a quantity sensor at the non-tabacco storage location. The quantity sensor may be a weight sensor, a height sensor or the like, depending on the type of material being sensed.

As shown in FIGS. 2 and 3, the CATCs are in communication with the Making and Packing management system. Each CATC collects data from the maker, packer, cartoner, case packer, palletizer, and cigarette inspection station at the complex and forwards this information to the Making and Packing Management system. This data is also stored at the CATC and available for display to operators, technicians and repair people. The data collected also includes data input directly by the operators such as operator id and requests for additional materials, as discussed above, or requests to remove rejects or accumulated debris. Also, it may happen that non-tobacco materials are moved directly from one complex to another. In this case, the operator can notify the CATC of the move of the materials so that the CATC can adjust its inventory.

The type of data accomulated by the CATC from the machines themselves for transmission up to the MPMS includes production data from each machine including production counts in the form of attempts to make cigarettes, attempts at tipping, movement of cigarettes from the maker into the accumulator, attempts at packaging, attempts at package wrapping, finished cases produced, etc. The CATC also reports the down time of the complex, in terms of both the reason for the down time and the duration of the down time, and the rejects produced by the complex.

Furthermore, the schedule can be modified at the MPMS to a limited extent. Runs can be inserted, deleted or modified. Any such modification must be authorized and is reported to the plant management system in order to modify the plant schedule.

The CATCs actually communicate accumulated data to the MPMS by transmitting all of the gathered data relating to machine operation to the data concentrators 144 and 146 via the Ethernet system as shown in FIG. 2 for storage in the common storage area 166 which can also be accessed by the MPMS. This data is transmitted at five minute intervals.

In like manner, the CATCs receive data from the microcomputers on the individual machines. This information is updated about every 15 seconds.

Also, specification data is sent by the MPMS to the CATCs through the common storage area. The spec data sent to the CATCs includes data which is necessary for the CATCs to order new non-tobacco materials to be delivered, data relating to the type of finished product being produced and the destination of the finished product, product and process parameters to be down loaded to the computer control systems on the various operating machines in the complex, targets and control limits for cigarette testing, menthol and regulator indicators for the product being produced in order to assist in ordering the AGVs to dump empty non-tobacco containers in menthol or regular bins in order to segregate these two types of products, and machine specification parameters, such as gear teeth numbers, to assist mechanics and the like in repairing, setting up or testing machines in the complex.

The MPMS is able to access the data stored in the common storage area by the CATCs and receives messages from the CATCs through the Ethernet network. For example, a CATC may transmit a request to the MPMS for more non-tobacco material to be delivered. The CATC stores the item id and version of the product being produced on each complex so that the CATC knows the exact specs of the material required. The CATC sends the request to the MPMS which sends the request on to the factory service management system which oversees delivery of the material to the requesting complex and reports back to the MPMS when the delivery is completed.

The MPMS serves the generate reports to users. Such reports include production and efficiency reports to supervisors and managers as well as reports on the status of the equipment control systems and the CATCs which are provided to the process control engineers and the maintenance people. The reports can be in both table format and graphic and are generated on CRT screens as well as in hard copy through printers. The reports may also be stored in the common disc storage area for future reference.

DATA COLLECTION SYSTEM

As discussed above with reference to FIG. 13, microcomputers are provided at the various pieces of equipment in each complex. These microcomputers provide the lowest level of data collection. They monitor the making and packing equipment through numerous sensors. The CATC, a DEC PDP11/83, polls the microcomputers at each complex to obtain production data, data regarding the number of reject products produced, and data regarding the downtime of each individual piece of equipment. The data is stored by day, shift, and run. The data gathered by the CATC is available for access by the Making & Packing Data Concentrator System (DCS).

Also as discussed above, the DCS consists of two VAX 11/750 computers 142 and 144 (FIG. 2a) for data collection, each reading data from half of the CATCs in the plant to distribute the load. The DCS places the data in the common disk storage area 166. This data is referred to as the Making & Packing Generic Process data (GPD). The MPMS accesses the GPD and summarizes and displays the data using various reports. The Making & Packing Management System computer 146 (also a VAX 11/750) together with the two DCS VAX 11/750 computers is known as the Making and Packing System. Due to size constraints, the Making & Packing System only keeps data for one week. The Plant Manager System 138 on Level III archives the data for historical use.

All data is collected on a complex basis. The data is broken down by run, shift, and day. Each day a new file is created to which all data for that day is posted. For each day, data is collected in three ways: by shift (historical), by run (historical) and dynamically (current).

SHIFT DATA

Shift data is collected at the CATC during every shift. At the end of the shift, the CATC saves the data in a shift record. The shift record contains information about the production, rejects, and downtimes that accumulated during the shift. A shift record can be uniquely identified by the complex id, the shift and the date. At the end of the shift the DCS collects the data to store in the GPD file. The shift record has no run specific information.

A shift is defined locally on the Making and Packing System. Each shift has a start time, end time, and a break start time and a break end time defined on the Making & Packing System. These times can be defined differently for each subunit of the making & packing floor. If the shift definition ever changes, the new shift information can be down loaded to the CATCs of each subunit. The CATCs will then perform shift changeovers based on the new shift schedule. A time synchronization process runs once an hour on the DCS to insure that CATCs remain on the same schedule as the Making & Packing System.

RUN DATA

Run data are collected based upon the complex's production schedule. The run record contains information about the product being produced, and the production, rejects, and downtimes that occurred during that run. A run record can be uniquely identified by the complex schedule. When a run change occurs, all data are posted to a run record on the CATC. The DCS then collects the data to store in the GPD file. Short runs may provide several run records per shift, with a maximum of six runs per complex per shift. A run that is longer than a shift will be broken into run records that are based on shift boundaries. This allows information to be reported either on a shift basis or on a full run basis. The manner in which run records are kept is illustrated below for a day which is broken into three parts, the 7 shift which runs from midnight to 8 am, the 8 shift which runs from 8 am to 6 pm and the 9 shift which runs from 6 pm to midnight:

One day's data - stored in a file by complex, shiftand run:

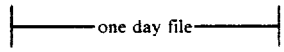

One shift record per complex stored in the day file:

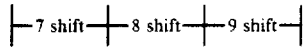

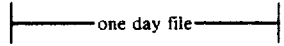

One run record for each run/shift for each complex in the day file:

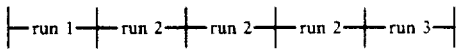

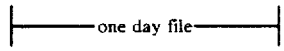

TREND DATA

The CATC can record selected data on a periodic basis and keep a selected number of data points in a trend record. The trend period can be from 15 seconds to 15 minutes. The number of trend points can be up to 32 points. Trends can be maintained of up to 50 data items and can be enabled or disabled for each individual CATC. This trend information is accessible on MPMS and is stored in the GPD.

DYNAMIC PROCESS DATA

A snapshot record is created whenever a run starts. This provides a record of the accumulated production and rejects when the run began. The DCS collects the snapshot record and stores it in the GPD file. Throughout the shift, accumulated shift data is collected from the CATC by the DCS and used to update the shift record for each complex. Current run data is determined by taking the difference between the snapshot values and the current accumulated shift values. At the end of a run or shift, the snapshot record is deleted from the GPD file and replaced with historical run record (as collected from the CATC).

SYSTEM LOGGING

Transaction Logging

Messages are communicated between the CATC and the DCS, between the DCS and the MPMS, and between the MPMS and other Level II systems, and between the MPMS and the Level III Plant Manager System. All of the messages successfully received from or sent to other systems are logged either by the DCS or by the MPMS. An example is a material order message sent by a CATC requesting additional inventory of an item needed by the complex served by the CATC. The message received by the DCS from the CATC, passed to the MPMS, which passes the massage to the Factory Service Management System (FSMS). The message contains information about the order, such as complex needing an item such as foil, paper or the like, the item identifier, the type of material, and the finished product item identifier. When the item is brought, the AGV brings the item on a pallet and removes the old pallet in the storage location in which new pallet is to be placed. The message originally sent to the FSMS also indicates whether the old pallet still contains material. The transaction is logged on the DCS when the DCS successfully gives the message to MPMS, and again the MPMS when MPMS successfully sends the message to FSMS. If the transaction does not complete successfully, it will be logged to an error log.

ERROR LOGGING

Applications residing on the MPMS and the DCS log all errors to a file called the Message Log. The Message Log is generally only used by Systems personnel for testing and debugging purposes.

CATC SIGN ON AND SIGN OFF LOGGING

When an operator, technician, repairer, or supervisor signs on to a CATC, the CATC notifies the Making & Packing System of the user class and an account number of the person signing on. When the operator, repairer, or technician signs off, the CATC notifies the Making & Packing System. The Making & Packing System uses this information to track all users currently signed on to the CATCs. The Making & Packing system keeps a log file of all sign on and sign offs for a minimum of one week. A report is provided for viewing current CATC sign on. The log file is generally used for testing and tracking purposes.

EDIT LOGGING

Some Making & Packing reports provide the user with the ability to change system information (schedules, configuration data, etc.). When one of these reports is used, an entry will be made in an Edit Log file indicating the users name, the time of the edit, and the terminal id if applicable. The log file is generally used for testing and tracking purposes.

MESSAGE LOGGING

Action and informational messages can be logged at the CATC. Action messages originate at the microcomputer level on the machines of a complex and indicate some event which should be transmitted immediately to the operator. For example, an action message could indicate the failure of a machine such as a tipper. Action messages appear on the crt of the CATC dynamically in real time when they are generated and are listed in chronological order in the message log. Informational messages contain information about less vital occurences in the complex, such as the completing of a pallet, material being ordered, etc. Informational messages are not displayed dynamically on the CATC crt, but are stored in the message log and can be accessed through the message log. Up to 500 messages can be maintained in the log.

REPORTING SYSTEM

A Making & Packing Reporting System provides a comprehensive set of on-line reports for users of the Making & Packing Management System. A menu system based on target user and type of report provides easy access to the reports.

The top level of "Root" menu for each user group provides both submenu selections and general utility selections. User group submenus are provided for Line Supervisors, Department Managers, Production Managers, the Operations Manager, Maintenance Personnel, and Plant Schedulers. Each user group submenu is further divided into submenus by report type. Report types include production, scheduling, reject overview, and downtime.

All of the Making & Packing reports are designed to use a standard set of control keys. Reports using dynamic data are updated on a one to ten minute basis, depending on the type of report and the frequency of data updates.

PRODUCTION REPORTING

Production reports summarize data pertaining to runs or shifts. The data may be displayed in various ways depending on the report, but is generally either run (brand) oriented or shift oriented. Reports targeted for higher level management summarize the production data by shift, department, or brand. Goal information is provided from a Plant Performance Reporting System on Level III and is used by the MPMS to produce a comparison against actual production.

REJECT REPORTING

Reject reports display sumarized and actual reject counts as collected by the CATC. Reject data may be displayed as a summary by type or reject, or as actual reject counts for certain sensors. Actual reject data is collected by the CATC. Some of the reject data displayed is calculated based upon information provided by the CATC.

PERSONNEL REPORT

A personnel report is provided to display all current sign on at the CATC. When an operator, repairer, on technician signs on to a CATC, the CATC notifies the Making & Packing System of the according number and user class for the sign on. When the operator, repairer, or technician signs off, the CATC notifies the Making & Packing System. The Making & Packing System uses this information to monitor all users currently signed on to the CATCs. The personnel report uses the account number for the current sign on to determine the name and labor grade of the person signed on. This information is then displayed on the report with an indicator showing where the sign on occurred.

OVERVIEW REPORTING

Overview reports provide a summary of Status, Production, and Downtime information.

Overview status reports provide information on the current status of the equipment on the floor. This includes micros, maker, packer, cello and case packer, and palletizer.

Overview production reports present a summary of production, rejects, and efficiencies. Goal information for production, rejects, and efficiency is provided for comparison.

Downtime reports display summarized and actual downtime information as collected by the CATC. Downtime data may be displayed either as "generic" downtimes or actual sensor reasons. A generic downtime is a general downtime reason that may have been captured by any of a number of actual sensors. This provides a generalized summary of the types of downtimes that have occurred. Actual sensor downtimes are specific to each sensor provided on the making and packing equipment. The CATC provides the Making & Packing System with both types of downtime information.

SCHEDULE REPORTING

Schedule reports provide information about the current Making & Packing Schedule. Reports display information on a complex basis, either displaying all runs for a complex, or displaying current and next runs for all complexes of a subunit.

The report Current and Next Schedules for a subunit provides information on the current run, and what information is available for the next run. The current information provided is the run number, the scheduled start time, the actual start time, the scheduled stop time, the quantity to be produced, the current quantity produced, and the termination criteria for the run. Information provided for the next run includes the run number, the scheduled start time, the scheduled stop time, the quantity to be produced, and the termination criteria. The report will flag any runs that have an actual production close to the scheduled production. This will help indicate to the Line Supervisor when a run change may be necessary in the near future.

INTERFACES TO LEVEL II SYSTEMS

The Making & Packing System has interfaces with four other Level II systems; Factory Service, Finished Goods, Automatic Guided Vehicles, and Primary Processing Management System.

AUTOMATIC GUIDED VEHICLE SYSTEM INTERFACE

An interface with the Automatic Guided Vehicles Management System (AGVMS) provides AGVMS with information on finished product available for pickup, and notifies the AGVMS when pallets need to be removed from a complex.

When the palletizer moves a pallet of finished production onto the pickup location 571 (FIG. 13) the CATC is notified that a pallet is complete. The CATC uses the run information to determine what is on the pallet, the product code, and the destination the finished product. The CATC also gets the number of cases on the pallet from the palletizer. This information about the pallet is then provided to the Making & Packing System. The pickup location on each complex is provided with a sensor to detect when a pallet of finished product is ready for pick up. This sensor is wired directly to the AGV system, so that an AGV can be dispatched to pick up the pallet. The AGVMS will then make a request to the Making & Packing Management System for the information associated with that pallet.

The AGV interface provides a means of removing empty or partial pallets from the complex storage positions 580-588 without ordering new materials. This is called a purge and is provided as a CATC menu option. The CATC notifies the Making & Packing System when the operator requests a purge. The Making & Packing System then notifies AGVMS about the items that need to be removed. Materials and pallets would be removed this way when the complex is being taken out of production and materials need to be returned to Factory Service. AGVMS will return a status indicating if the removal was completed successfully or if an error occurred during the move.

FACTORY SERVICE SYSTEM INTERFACE

An interface with the Factory Service Management System provides the means for the making, packing, and filter operators to order materials. The operator orders materials through a CATC material ordering screen. The CATC notifies the Making& Packing System when the operator has made a selection. The request for that material is given to the Factory Service Management System. The Factory Service Management System will check the material inventory and determine if the material is available. If the material is available, the Factory Service Management System will notify the Making & Packing System, which will notify the CATC that the material order was completed successfully. If the material cannot be ordered successfully, the Factory Service Management System will provide a reason that the material is not available. The Making & Packing System will provide this information to the CATC for display to the operator.

FINISHED GOODS SYSTEM INTERFACE

An interface is provided with the Finished Goods Management System (FGMS) to notify Finished Goods when a manual (non-AGV) product transfer has been made at a complex. The ability to log the manual transfer is provided by the CATC. The CATC notifies the Making & Packing System when a manual transfer has been logged. This information is then provided to FGMS.

PRIMARY PROCESSING MANAGEMENT SYSTEM INTERFACE

The Making & Packing accesses a shared file provided by the Primary Processing Management System (PPMS) Level II to obtain cut filler storage information. PPMS updates the file on a dynamic basis. The Making & Packing System will ignore the provided data if it is out of date.

The file provides the Making & Packing System with information about the bin, feeder, and blend code for each complex. The making & Packing System compares the CFS blend code against the scheduled blend code for each complex. If a discrepancy exits, the Making & Packing System notifies the CATC about the possible error. The CATC will display a message about the discrepancy to the operator.

After the CATC has been notified of the possible error, the Making & Packing System will track the discrepancy and notify the CATC if the problem is corrected.

INTERFACES TO LEVEL III SYSTEM

Interfaces with the Level III system are used to get information from other systems and provide information to other systems. These interfaces provide the Making & Packing system with M&P schedules and Manufacturing Standards. The interfaces also provide other systems with information on finished goods production, local schedule changes, on floor inventory, and plant performance data.

SCHEDULING SYSTEM INTERFACE

The Scheduling System provides a means of specifying what product is to be made at each work center (complex). The scheduling system provides:
1. a means for getting a schedule from Level III,
2. entry, modifications, and viewing at the Making & Packing Management System, and
3. a means for down loading schedules to the CATC.

The schedule is a collection of runs for each work center. A run defines what finished product is to be made at one work center. A run specifies the finished good and version, the work center identification, the start and end times the planned production, termination criteria, and special instructions. The schedule is a sequential list of runs that will be executed in the given order. Only one set of specifications apply to a run; therefore only one set of materials, product and process specifications, and cut filler storage lineup apply to the run. If any materials change, a feeder changes, or a specification changes a new run must be scheduled, or the existing run modified.

The run is identified by a run number that is used to easily identify the run. The run number is used for documentation purposes only.

The master copy of the schedule resides on the Making & Packing System. The Level III system can request a copy of the schedule from MPMS, insert a fence between runs to divide the runs into those that can be executed and those that are on hold, commit a new schedule, or abort a Level III edit and remove fences.

MPMS provides the means of modifying a workcenter's schedule through the use of a schedule edit report. Runs can be added, deleted, or modified. This local edit takes priority over a Level III edit and will cause the automatic abort of a Level III edit in progress. A Level III edit places a fence between runs and the fence may be placed between any two runs or at the end of the schedule. No editing can be done at the CATC.

Edits cannot be done on current runs. Edits can be done on the next run and all subsequent runs. The CATC contains a current and a next run. When the next run is edited, the next run at the CATC is zeroed out along with the associated specifications. When a new next run is committed, the run and its specifications are down loaded to the CATC. A local edit on MPMS always allows edit of the next run.

The completion of a current run and transition of the next to the current is called a run change, and can only be done at the CATC. When a run change is started at the CATC, the end of run event is sent to Making & Packing System, which adjusts the schedule to complete the current run and make the next run current. This also closes out the Generic Process Data record for the current run and causes a new current run record to be created. There can be a maximum of six runs per shift per complex.

SPECIFICATION SYSTEM INTERFACE

The specification System provides product, process, and material specifications for products that are scheduled for Making & Packing runs. The specifications that are provided through MPMS are a subset of the specifications available through the Manufacturing Standards System (MSS) that are needed by Making & Packing to support material ordering, finished goods delivery, making, packing, and palletizer processing, and quality testing.

MPMS contains the specifications for all product that is currently scheduled for Making & Packing, and that which is scheduled as the next product. Specifications are obtained from MSS via the plant Level III system. The specifications are maintained on MPMS and distributed to the CATCs. A set of specifications is identified by a finished goods identifier (FGID) and a version number. Only one copy of each set of specifications is maintained. Multiple work centers may share the same specifications.

A set of specifications apply to the entire work center. All of the materials, products, and processes for making, packing, and palletizing are specified by the product id and version. Sets of specifications are maintained for all products scheduled for current and next runs.

At the time a product is scheduled as the next run, the Making & Packing System Specifications are checked to determine if the specifications are already being maintained on the Making & Packing System. If they are not available locally, a request is made to Level III for them. If they are locally available or when they become available through Level III, they are down loaded to the CATC. If specificatins are not available either locally or from Level III, the CATC will not get the next schedule and the associated specifications. When a run record is created in the GPD file, certain specifications are copied into the run record for use by reporting functions.

There are no user functions that allow viewing or editing of specifications on MPMS. A data base maintenance function deletes specifications that are no longer needed for current or next runs.

PLANT PERFORMANCE REPORTING SYSTEM INTERFACE

The CATC collects data for use by the Plant Performance Reporting System (PPRS). This data provides detailed information about production and reject information on an operator level, and about downtimes that have occurred on the making & packing equipment.

Operator data includes operator sign on time, operator sign off time, total production (either tipper accepts for maker operator or cases palletized for packer operator), and the number of downtimes that have occurred during the sign on.

Downtime data includes the time that the equipment went down, the time that is resumed operation, the sensor reason for the downtime, and the account number of the operator signed on when the downtime occurred. If a repairer or technician is called to asist bringing the equipment back up, the CATC will include the time that the repairer or technician signed on and the account number for the repairer or technician. No information is recorded about repairer/technician response if the repairer or technician does not sign on to the CATC.

The CATC also provides a means of allowing operator entries for each downtime. These entires can be made by operator, repairer, or technician through the use of a menu process. By moving through the menu, a code is built that describes the nature of the problem, the part of the equipment that problem was associated with, and the action that was taken by the user to correct the problem. The information provided by the menus for the selection process is provided by the PPRS system through the interface. The information provided by the PPRS system for the menus is manually transmitted to the Making & Packing system from PPRS to be down loaded to the CATCs by Systems' personnel.

After each shift, a process on the DCS will collect all of the PPRS data that has been logged by the CATC for that shift. The DCS places all of this data in a shared file accessible by the MPMS. Daily, MPMS notifies PPRS when the data is available for transmission.

INVENTORY REPORTING

On floor inventory of Factory Service materials stored in the storage location 588 is tracked on a shift basis by the CATC. When materials are received from Factory Service, the inventory for that item is increased by the amount on the pallet. The CATC calculates that amount of material used for producing the finished product, and subtracts this usage from the pallet inventory. The DCS collects this information on a dynamic and on a shift basis and stores the information in the Process Data file.

On floor inventory of finished product is provided by the CATC on a "snapshot" basis. The Level III system notifies the Making & Packing System of the time that a product inventory snapshot should take place. The Making & Packing System then notifies all CATCs of the snapshot time. At the time provided by Level III, each CATC will determine the current product inventory at it's complex and notify the Making & Packing System of the amount. All of these inventory snapshot messages received from the CATCs will be routed to the Level III system.

FACTORY SERVICE SYSTEM

The factory service system comprises an automated warehouse type storage and retrieval system which is of conventional design and controlled by a factory service control system which stores non-tobacco materials and retains informatin for locating the stored materials. The control system operates under the direction of a Factory Service Management System (FSMS) which communicates with the MPMS and the AGVMS to ensure that requested materials are delivered to the various complexes which require them. The FSM, as shown in FIG. 1 is one computer within a distributed network of computing machines. It is required that the FSMS be able to send to and receive messages from the MPMS as well as the AGVMS. The FSMS must also have access to the common storage area 166.

OPERATION DESCRIPTION

Receiving Operator-Wrapping material will arrive by truck at the Factory Service Dock. The truck driver will deliver a transfer document (inter-company material) or a Bill of Lading (purchased material) to the Receiving Operator. The Receiving Operator will decide if the material will be stored. The Receiving Operator will validate the shipment by accessing the Plant Management System. The pertinent data for entry is either the transfer location number (from the transfer manifest) or the purchase order number (from the bill of lading). For purchased material, the FSM will access the Expected Receipts file on the Plant Management System. If the purchase order is found, the expected receipts will be displayed to the Receiving Operator. Should the purchase order number be invalid (non-existent or closed), or should any material not be listed as expected, the Receiving Operator will be required to communicate directly with the plant management for authorization to accept the shipment.

Inter-plant transfers of material are handled similar to purchased material. Each Item ID will be handled as a separate shipment receipt.

All accepted shipments will be assigned a unique Shipment Receipt Number by FSM comprised of twelve digits (YYMMDDHHMMSS). This number will be written on all shipping documents. All shipment information is sent to the corporate computer (nightly), and all pallets for that shipment have passed the data entry station.

The fork truck operator, upon receiving permission to unload a truck, will place the material on a slave pallet. When the fork truck operator backs his vehicle away, floor sensors will detect the completion of the input process. The pallet will then be released into the system.

The pallet ID of the salve pallet should already be known to FSCS at the time the operator is ready to place material upon it. If a pallet No-Read condition should be encountered, an alarm will be activated which will instruct the fork truck operator to remove the pallet in question. Every pallet received into the system will, of necessity, be delivered to the data entry station. Each pallet will be scanned for its pallet ID and weighed by FSCS when it arrives. This information will be displayed to the Data Entry Operator, when available, along with the shipment receipt number when known. The operator should have the ability to input any missing data before proceeding.

Any pallet ID detected by the scanner or input by the operator will be validated against a list of pallets enroute to the data entry station. In the case where the pallet ID is unexpected, the operator will be so notified and will be requested to confirm the pallet id.

When the communication link between FSCS and FSM is esablished, FSM will send to FSCS an available for store bin map. When a pallet arrives at an input pick up and delivery station (P&D), FSCS will select a storage location within the aisle using the available for store bin map. FSCS will then issue a command to the SRM to pickup the pallet. If the SRM successfully reads the pallet ID when picking up the load, the pallet will be stored and a store completion transmitted to FSM. If the SRM was unable to read the pal)et ID, the pallet will be deposited on the staging area output P&D stand. FSM will be notified of the "flush" of the "unknown" pallet. If a full bin error occurs, FSCS will notify FSM of the error and will then select another bin location to store the load. Full bin errors will be logged for manual investigation and recovery.

Material Retrieval-Material may be ordered in two ways: automatically by request from the M&P Manager and manually by video display terminal (VTD) request to FSM. (Material may also be removed by VDT input to FSCS whenever FSM is down.)

M&P REQUEST—These requests must include the following data: complex number, manufacturing-ID, item-ID, item type, pallet empty/return, quantity (optional), and export order invoice number (optional).

VDT REQUEST—Manual requests can be made to FSM by any the following:
Item-ID
Pallet Number
Bin Location Material retrieval will index forward to the end of the output P&D lane. The AGV system senses the presence of the pallet at the end of the lane and commands the AGV to move the pallet to a staging area stand. The staging area operator will inform FSM that the load has arrived on a staging area.

Before shipping any material to the production floor, a pallet must be delivered to the staging area where all outerwraps (bands, stretch wrap, etc.) can be removed. The disbursements operator will "receive" a pallet into staging by either scanning the pallet bar-code or by typing the pallet ID on the VDT keyboard. FSM will then supply the operator with relevant instructions (e.g. prepare pallet for shipment to M&P complex). The disbursements operator will then release the load and FSM will notify the AGV Manager of the pallet transport request. Should the AGV manager system be "down", the operator must enter the move command on the AGV Control System.

The Item Master File will distinguish between Full Pallet and Pick Pallet material. In general, the following are examples of some items which should be delivered as full pallets: tow, plug wrap, purchased filters, cigarette paper, tipping, foil, wrappers, pack film cartons cases.

Material that is not delivered to the production floor in full pallet quatities must be picked at the staging area and delivered to the floor in one of two ways: as part of some other shipment to the specified complex or by three sided cart. After picking, the pallet is returned to storage unless the entire contents are removed, in which case the slave pallet willbe directed (by operator entry) to a slave pallet collector. The following are examples of items which will be delivered in partial pallet quantities: tear tape, stamps, wax in bags carton overwrap wrapping.

MAKING AND PACKING ORDERS

M&P sends orders for material to FSM. These orders indicate whether an empty pallet should be removed or a partial pallet should be returned to storage. When FSM accepts an order, it instructs the AGV Manager to remove the slave pallet presently residing at the deposit point (the FSM will always assume that this pallet is present, even though it might not be). The FSM may then issue an order for the pallet to be retrieved from a bin in AS/RS.

INTERFACES

AGV Interface-FSM has only a single transactional interface with the AGVS Manager: a MOVE command. Each MOVE command is comprised of at least four (4) items of information: the source-(pickup) location, the destination (deposit) location, the ID of the pallet involved, and the type of material associated with the pallet. Optionally, a postion within a complex and a move priority will be included in the comman. The AGVS Manager is required to notify FSM at the time the MOVE command is completed or if the move had failed. The following is a listing of examples of these locations:
All staging area positions
Every M&P complex
Each position at every filter complex
Every slave pallet collector station
Possible error conditions include:
No pallet at specified source location
Pallet already present at specified destination
Pallet placed at wrong position
Pallet delivered to wrong location
AGV cannot complete delivery Making and Packing Interface—FSM will recognize a single transaction sent by the M&P Manager: a delivery request. In this transaction, the M&P Manager supplies the complex-ID, manufacturing-ID, item-ID, item type, pallet empty/return, quantity, position within the filter complex, and export order invoice number. FSM will then schedule the appropriate pallet movements to deliver the required material. Once delivered, FSM will so inform the M&P Manager. If the request cannot be satisfied, the full request will be rejected with an appropriate alarm code. When complete, FSM will transmit an order completion message to the M&P Manager indicating complex-ID, manufacturing-ID, item-ID, item category, quantity delivered, pallet-ID, and export order invoice number.

Possible error conditions include:
Not in inventory
In transit—temporarily unavailable
Equipment out-of-service
Item status is obsolete
Item category does not match item-ID
Item is in export room
AGV failure
Invalid message Plant Management Interface—FSM is responsible for providing four (4) specific services to level IV systems (via tbe Plant Management System):
(1) Notification of any changes to inventory on-hand such as:

Arrival of purchased materials at the dock from a vendor. The information transmitted is as follows:
- Loc-number
- Date
- Order-number
- Item-id
- Quantity Received
- Shift
- Carrier
- Carrier-number
- Documents Factory Service from M&P Floor. The following information is transmitted:
- Loc-number
- Item-id
- Quantity
- Shift
- Adjustment Code
- Date (2) Shipments to vendor for Credit.
Request for credit for rejected purchased materials to be returned to the vendor. The information to be transmitted includes:
- Loc-number
- Item-id
- Credit-number
- Vendor-number
- Quantity
- Shift Delete a request for credit for rejected Factory Service materials to be returned to the vendor. The following information is transmitted:
- Loc-number
- Credit-number Disposal for credit of purchased materials returned to the vendor for credit. The following information is transmitted:
- Loc-number
- Credit-number
- Adjustment Code
- Sign (3) Shipments for Material Disposal
Authorized disposal of purchased materials destroyed because of obsolescence, damage, etc. The following information is transmitted:
- Loc-number
- Item-id
- Quantity
- Adjustment Code
- Date To provide the vital functions described above, the FSM must be capable of accessing the Plant Management System for the following:

VENDOR FILE
- Vendor-number
- Vendor-name

PURCHASE ORDER FILE
- Order-number
- Po-item-id
- Po-vend number
- Po-status
- Po-order-quantity
- Po-balance-due ITEM FILE
- Item-id
- Description
- Quantity-per-pallet
- Unit-of-measure
- Status
- Category
- Type LOCATION FILE
- Loc-number
- Loc-discription In addition, FSM must be capable of updating the Plant Management System with the following:
- FSCS System Performance Statistics
- FSCS Equipment Performance Statistics The foregoing is intended as an illustrative description of the present invention but is not intended to limit the scope of the invention in any way. Clearly, numerous modifications by way of additions, deletions, and substitutions can be made to the invention without departing from the scope thereof as set forth in the claims which follow.

What is claimed is:

1. A multilevel computerized process control system, comprising:

a first level computer system comprising at least one first computer for controlling a plurality of individual processes for producing a plurality of different products, said first level computer system comprising:

a plurality of sensor inputs for receiving process monitoring sensor signals from sensors at respective process stations, a plurality of control outputs for providing control signals for processes to be controlled, p1 storage for storing process control parameters for processes to being carried out, storage for storing bill of materials records containing indications of materials necessary for products being produced;

storage for storing values of said sensor signals, and programs for producing said control signals to control said processes as a function of said sensor signal values and said process control parameters for processes being carried out;

a second level computer system comprising at least one second computer connected to said first level computer system and storing a database having a plurality of files containing process control parameters associated with different processes which may be required to be performed by said first level computer system to produce different products, said files including a process specification file containing records indicating process control parameters necessary for producing said different products and a bill of materials file containing records indicating materials necessary for producing said different products, said second level computer system:

being connected to receive scheduling information indicative of scheduled process controls to be carried out by said first level computer system to produce scheduled products, being programmed to provide selected ones of said control parameters necessary to carry out said scheduled process controls to said first level computer system as said control parameters for processes being carried out and to provide selected records from said bill of materials file indicating materials necessary for producing said scheduled products as said materials for products being produced, and being programmed to receive indications of said values of said sensor signals; and a third level computer system connected to said second level computer system, said third level computer system being programmed to generate said database and transmit said database to said second level computer system and being connected to receive modification instructions for modifying records of said database, said modification instructions being contained in a modification instruction file containing information for modifying said records and information as to times at which modifications to said records are to be implemented.

2. A system as set forth in claim 1 wherein said second level computer system includes monitor drivers for displaying said values of said sensor signals on operator console monitors.

3. A system as set forth in claim 1 wherein said database includes a product specification file having records with data related to specifications of a product to be produced.

4. A system as set forth in claim 3 wherein said third level computer system stores an item master file containing records having purchasing data, and accounting data related to products produced and materials purchased.

5. A system as set forth in claim 4 wherein said third level computer system stores a revision control file containing information on revisions to any other file.

6. A system as set forth in claim 1 including an automated material delivery system for providing material to said process stations, and a further second level computer system for controlling operation of said automated material delivery system in response to commands for material received from said processing stations.

7. A system as set forth in claim 1 wherein said first level computer system comprises a lower level of computers having a plurality of identical computers programmed to carry out specific process functions, and a higher level computer connected to other first level computer systems in a communication network, said higher level computer being connected to said plurality of lower level computers and being programmed to receive process control parameters required for said lower level computers to carry out their specific process functions from said second level computer system, transmit said received process control parameters to said respective lower level computers as required for said lower level computers to carry out their programmed specific process functions, receive sensor signal values from said respective lower level computers and transmit said received sensor signal values to said second level computer system.

8. A system as set forth in claim 7 wherein said second level computer system comprises a superior level computer and an inferior level of computers, said inferior level of computers comprising a plurality of identical computers connected together in a communication network and being connected to a respective plurality of higher level computers of said first level computer network, said inferior level of computers being programmed to display said received sensor signal values on display consoles, and receive from said superior level computer and store respective portions of said database required for said lower level computers to carry out their specific process function.

9. A system as set forth in claim 1 wherein said scheduling information comprises a production schedule for a first predetermined period of time, and said second level computer system provides to said first level computer system a second production schedule which covers a second period of time shorter than said first period of time.

10. A system as set forth in claim 8 wherein said scheduling information comprises a production schedule covering a first period of time received by said superior level computer and wherein said superior level computer provides scheduling information to said inferior level computers which covers a shorter period of time and said superior level computer provides said respective portions of said database to said inferior level computers which contain process parameters required over said shorter period of time to meet said production schedule.

11. A system as set forth in claim 1 wherein said second level computer system stores a product definition file having a record for each product to be scheduled, each record of said product definition file containing information indicating all bill of material records for a particular product to be scheduled and all process control parameters for the particular product to be scheduled.

12. A system as set forth in claim 11 wherein said second level computer system accesses one of said product definition file records in response to said scheduling information indicating a product to be produced and passes the accessed product definition file record to said third level computer system.

13. A system as set forth in claim 12 wherein said third level computer system receives said accessed product definition file record and produces said control signals by determining process variable set points from said process control records.

14. A system as set forth in claim 7 wherein said third level computer comprises a plurality of individual higher level computers interconnected by a networking system.

15. A system as set forth in claim 14 wherein said networking system comprises a collision system.

16. A systemas set forth in claim 14 wherein said lower level computers are connected to said higher level computers by a second networking system.

17. A system as set forth in claim 16 wherein said second networking system comprises a polling system.

18. A systemas set forth in claim 1 wherein said second level computer system comprises a plurality of individual second level computers interconnected by a second level networking system.

19. A system as set forth in claim 18 wherein said second level networking system comprises a collision system.

20. A system as set forth in claim 1 including a common disc storage area and wherein said second and third level computer systems are connected to said common disc storage area.

21. A system as set forth in claim 1 wherein said third level computer system stores a modification file containing records, each modification order record containing a modification order number, approval data corresponding to said modification order number and change reason data indicating a reason for the modification corresponding to said modification order number.

22. A multilevel computerized process control system, comprising:

a first level computer system comprising at least one first computer for controlling a plurality of individual processes for producing a plurality of different products, said first level computer system comprising:

a plurality of sensor inputs for receiving process monitoring sensor signals from sensors at respective process stations as well as sensors for receiving indications of material levels of products in process, a plurality of control outputs for providing control signals for processes to be controlled, storage for storing process control parameters for processes to being carried out, storage for storing bill of materials records containing indications of materials necessary for products being produced;

storage for storing values of said sensor signals, and programs for producing said control signals to control said processes as a function of said sensor signal values and said process control parameters for processes being carried out;

a second level computer system comprising at least one second computer connected to said first level computer system and storing a first database having a plurality of files containing process control parameters associated with different processes which may be required to be performed by said first level computer system to produce different products, said files including a process specification file containing records indicating process control prameters necessary for producing said different products, and a bill of materials file containing records indicating materials necessary for producing said different products, and a second database storing plant production and inventory records containing inventory levels and plant production data, said second level coputer system: p1 being connected to receive scheduling information indicative of scheduled process controls to be carried out by said first level computer system to produce scheduled products, being programmed to provide selected ones of said control parameters necessary to carry out said scheduled process controls to said first level computer system as said control parameters for processes being carried out and to provide selected records from said bill of materials file indicating materials necessary for producing said scheduled products as said materials for products being produced, being programmed to receive indications of said values of said sensor signals and update said plant production and inventory records; and a third level computer system connected to said second level computer system, said third level computer system being programmed to generate said first database and transmit said first database to said second level computer system and being connected to receive modification instructions for modifying records of said first database, said modification instructions being contained in a modification instruction file containing information for modifying said records of said first database and information as to times at which modifications to said records of said first database are to be implemented.

23. A system as set forth in claim 22 wherein said second level computer system also stores an operating instruction file containing information from certain records of said first database relating to operating instructions for producing said different products, and a recipe file containing information from certain records of said first database relating to components for producing said different products, and said operating instruction file and said recipe file comprise said selected ones of said control parameters provide to said first level computer system.

24. A system as set forth in claim 22 wherein said second level computer system provides material on hand displays based on information relating to material being processed provided from said first level computer system.

25. A system as set forth in claim 24 wherein said second level computer system further comprises means to permit manual adjustment of inventory levels in said second database.

26. A system as set forth in claim 24 wherein said second level computer system provides a transaction log for indicating chronological inventory events.

27. A system as set forth in claim 22 wherein said second level computer system includes means for accumulating information relating to raw material inventories and for producing a raw material inventory report indicating the inventory level of said raw materials.

28. A system as set forth in claim 22 wherein said second level computer system includes means for accumulating information relating to products produced and producing a position report indicating the inventory level of said products produced.

29. A system as set forth in claim 23 wherein said second level computer system down loads into active memory of said first level computer system recipes and operating instructions from said recipe and operating instruction file for a current run and a next subsequent run, and said first level computer system also stores a copy of said recipe file and said operating instruction file.

30. A system as set forth in claim 22 wherein said first level computer system receives and stores data relating to production based on operating day, operating shift, and operating run.

31. A multilevel computerized process control system according to claim 1, wherein said first level computer system comprises a plurality of first computers disposed in a plurality of manufacturing plants and said second level computer system comprises at least one second computer in each said manufacturing plant, and wherein said third level computer system is connected to all of said second level computers to provide centralized multi-plant control.

32. A multilevel computerized process control system according to claim 1 wherein said third level computer system is programmed to generate a master schedule and transmit said master schedule to said second level computer system as said scheduling information.

33. A multilevel computerized process control system according to claim 32 including in said first level computer system inputs for receiving signals indicative of inventory levels of materials required to produce scheduled products and wherein data indicative of material levels of products in process and inventory levels of materials required to produce scheduled products are transmitted by said first level computer system to said second level computer system, and said second level computer system generates individual schedules for the individual processes based thereon and based on said master schedule.

34. A multilevel computerized process control system according to claim 33 wherein said second level computer system is programmed to provide call outs to vendors for ordering materials required by said individual schedules.

35. A multilevel computerized process control system according to claim 32 wherein said third level computer system is programmed to receive and generate said master schedule based on data indicating a long range forecast of demand for products to be produced and data indicating long range capacity production capacity.

36. A multilevel computerized process control system according to claim 34 wherein said call outs are generated by said second level computer system by subtracting daily material requirements as determined from said individual schedules from inventory in the plant.

37. A multilevel computerized process control system according to claim 1 wherein said first level computer system comprises a plurality of computers connected to control a plurality of said individual processes in a sequential processing line.

38. A multilevel computerized process control system according to claim 37 wherein said sequential processing line is a cigarette manufacturing line.

39. A multilevel computerized process control system according to claim 38 wherein said cigarette manufacturing line includes means for conditioning tobacco to carry out a tobacco condition process as one of said sequential processes.

40. A multilevel computerized process control system according to claim 39 wherein said cigarette manufacturing line includes means for cutting tobacco to carry out a tobacco cutting process after said tobacco conditioning process.

41. A multilevel computerized process control system according to claim 40 wherein said cigarette manufacturing line includes means for making cigarette rods from cut tobacco after said tobacco cutting process to carry out a cigarette rod making process.

42. A multilevel computerized process control system according to claim 41 wherein said cigarette manufacturing line includes means for packing cigarette rods into a cigarette pack after said cigarette rod making process to carry out a cigarette packing process.

43. A multilevel computerized process control system according to claim 42 wherein said cigarette manufacturing line includes means for cartoning cigarette packs after said cigarette packing process to carry out a carton packing process.

44. A multilevel computerized process control system according to claim 43 wherein said cigarette manufacturing line includes means for palletizing cigarette cartons after said carton packing process.

* * * * *

UNITED STATES PATENT AND TRADEMARK OFFICE
CERTIFICATE OF CORRECTION

PATENT NO. : 4,827,423

DATED : May 2, 1989

INVENTOR(S) : Thomas B. BEASLEY et al.

It is certified that error appears in the above—identified patent and that said Letters Patent is hereby corrected as shown below:

Column 2, line 18, change "being" to --be--;

line 44, change "contrl" to --control--;

line 68, change "continuing" to --containing--.

Column 3, line 11, change "materials" to --material--.

Column 4, line 64, change "grded" to --graded--.

Column 6, line 21, change "pelletizing" to --palletizing--;

line 30, change "cigareete" to --cigarette--;

line 68, change "art" to --at--.

Column 8, line 9, change "etc" to --etc.--;

line 11, change "contrl" to --control--.

Column 9, line 12, change "ry5" to --ry 5--;

line 49, change "etc" to --etc.--;

line 50, change "DRMS" to --DRM--.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 11, line 5, change "assessable" to --assessible--;

line 51, change "Uled" to --uled--;

line 68, change "etc" to --etc.--;
      line 6, change "scheduable" to --schedulable--.

Column 13, line 3, change "processes" to --process--;

line 59, delete "the" before "used".

Column 15, line 42, change "filers" to --filters--.

Column 16, line 35, change "etc" to --etc.--;

line 66, change "ech" to --each--.

Column 17, line 2, change "recods" to --records--;

line 13, change "etc" to --etc.--;

line 32, change "appliable" to --applicable--;

line 51, change "CONROL" to --CONTROL--.

Column 18, line 28, change "Identifis" to --Identifies--;

line 48, change "spec re" to --spec. rev.--.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 19, line 34, change "fo" to --of--;

line 44, change "item id" to --ITEM ID--;

line 45, change "rev level" to --REV LEVEL--.

Column 20, line 10, change "rev level" to --REV LEVEL--;

line 12, change "rev" to --REV--;

line 15, change "rev levels to --REV LEVELS-- and change "rev" to --REV--;

line 16, change "items ids" to --ITEMS IDS--;

line 17, change "rev level" to --REV LEVEL--;

line 49, after "in" insert --a--;

line 60, change "cost" to --Cost--.

Column 21, line 16, change "are" to --a--;

line 37, change "th" to --the--;

line 38, change "cigaretted" (both occurrences) to --cigarette--;

line 42, change "rev level" to --REV LEVEL--;

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above-identified patent and that said Letters Patent is hereby corrected as shown below:

line 47, change "of" to --in--;

line 56, change "rev" to --REV--;

line 57, change "level" to --LEVEL--;

line 63, change "ass" to --as--;

line 68, change "rev" to --REV--.

Column 24, line 2, change "etc" to --etc.--.

Column 25, line 39, change "shcedulable" to --schedulable--.

Column 26, line 34, change "effectie" to --effective--.

Column 27, line 21, change "id" to --ID--;

line 44, change "etc" to --etc.--.

Column 28, line 1, change "maste" to --master--;

line 6, change "form" to --from--.

Column 29, line 27, change "requriements" to --requirements--.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 30, line 1, change "yeat" to --year--.

Column 31, line 13, change "ran" to --run--;

line 15, change "ie" to --i.e.--;

Column 32, line 43, change "complex(s)" to --complex(es)--;

line 58, change "latter" to --later--.

Column 32, line 21, after "to" insert --be--;

Column 34, line 52, change "a" (first occurrence) to --an--;

line 64, change "varius" to --various--.

Column 38, line 11, change "173" (first occurrence) to --172--;

line 21, after "to" insert --be--.

Column 39, line 14, change "which" to --with--.

Column 43, line 66, after "amounts" insert --and--.

UNITED STATES PATENT AND TRADEMARK OFFICE
CERTIFICATE OF CORRECTION

PATENT NO. : 4,827,423

DATED : May 2, 1989

INVENTOR(S) : Thomas B. BEASLEY et al.

It is certified that error appears in the above—identified patent and that said Letters Patent is hereby corrected as shown below:

Column 45, line 48, delete "the".

Column 48, line 2, delete "subtraction" and insert --subtracting--;

line 15, change "could" to --would--;

line 29, delete "compaed" and insert --compared--;

line 43, change "with" to --within--. (2nd occurrence)

Column 49, line 5, change "level" to --Level--;

line 64, change "updaating" to --updating--.

Column 50, line 32, delete "OPPMS" and insert --PPMS--;

line 33, change "Batch" to --batch--;

line 35, change "Batch" to --batch--;

line 39, change "Batch" to --batch--;

line 40, change "Batch" to --batch--.

Column 52, line 4, change "schedule" to --scheduled--;

line 11, delete "further" and insert --future-- and change "availabe" to --available--;

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

line 33, change "load" to --loading--;

line 36, change "new" to --newly--.

Column 53, line 2, change "message" to --messages--;

line 3, delete "that" and insert --the--;

line 29, change "barcode" to --bar code--;

line 47, change "program" to --programs--.

Column 54, line 5, change "system" to --systems--;

line 17, change "urea" to --area--.

Column 55, line 52, change "form" to --from--;

line 65, change "dat" to --data--.

Column 56, line 5, change "BATCH/RUNHISTORY" to --BATCH/RUN HISTORY--;

line 15, change "PPMSs" to --PPMS--;

line 58, delete "in" and insert --is.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 57, line 13, change "messages" to --message--;

line 33, after "therefore" insert a comma;

line 65, delete "form" and insert --from--.

Column 59, line 8, delete "Ssender" and insert --Sender--;

line 21, change "Sstor-" to --Stor--;

line 63, change "7" to --5--;

line 64, change "dataon" to --data on--;

line 65, change "inventor" to --inventory--.

Column 60, line 3, change "Receipe" to --Recipe--;

line 42, change "filed" to --file--;

line 67, change "Batch run/software" to --Batch/run software--.

UNITED STATES PATENT AND TRADEMARK OFFICE
CERTIFICATE OF CORRECTION

PATENT NO. : 4,827,423

DATED : May 2, 1989

INVENTOR(S) : Thomas B. BEASLEY et al.

It is certified that error appears in the above—identified patent and that said Letters Patent is hereby corrected as shown below:

Column 61, line 24, change "preiodic" to --periodic--;

line 45, change "thereis" to --there is--;

line 64, change "Level II" to --Level I--.

Column 62, line 47, change "form" to --from--.

Column 63, line 5, change "Level In" to --Level I in--;

line 11, change "of" to --to--;

line 41, change "barcode" to --bar code--;

line 54, change "host" to --hosts--.

Column 64, line 26, after "can" insert --be--;

line 53, delete the period after "conventional";

line 56, change "casepacker" to --case packer--;

line 57, change "casepacker" to --case packer--.

Column 65, line 17, change "markers" to --makers--.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 66, line 10, change "tabacco" to --tobacco--;

line 30, change "accomulated" to --accumulated--.

Column 67, line 3, change "machanics" to --mechanics--;

line 18, change "the" to --to--.

Column 68, line 39, change "shiftand" to --shift and--.

Column 70, line 18, change "crt" to --CRT--;

line 21, change "occu" to --occur--;

line 24, change "crt" to --CRT--;

line 63, change "sumarized" to --summarized--;

line 64, change "or" (first occurrence) to --of--.

Column 71, line 66, change the semicolon to a colon.

Column 72, line 13, after "destination" insert --of--.

UNITED STATES PATENT AND TRADEMARK OFFICE
CERTIFICATE OF CORRECTION

PATENT NO. : 4,827,423
DATED : May 2, 1989
INVENTOR(S) : Thomas B. BEASLEY et al.

It is certified that error appears in the above—identified patent and that said Letters Patent is hereby corrected as shown below:

Column 73, line 45, insert a comma after "times";

line 49, after "therefore" insert a comma.

Column 74, line 32, delete "and" (first occurrence);

line 59, change "specificatins" to --specifications--.

Column 75, line 19, change "asist" to --assist--;

line 27, change "entires" to --entries--.

Column 76, line 7, change "informatin" to --information--;

line 56, change "salve" to --slave--.

Column 77, line 12, change "pickup" to --pick-up--;

line 15, change "pal)et" to --pallet--;

line 33, after "any" insert --of--;

line 47, change "bar-code" to --bar code--;

line 63, change "quatities" to --quantites--.

UNITED STATES PATENT AND TRADEMARK OFFICE
CERTIFICATE OF CORRECTION

PATENT NO. : 4,827,423

DATED : May 2, 1989

INVENTOR(S) : Thomas B. BEASLEY et al.

It is certified that error appears in the above—identified patent and that said Letters Patent is hereby corrected as shown below:

Column 78, line 3, after "bags" insert a comma;

line 25, change "comman" to --command--;

line 65, change "level" to --Level--;

line 66, change "tbe" to --the--.

Column 80, line 6, change "discription" to --description--;

line 31, delete "pl";

line 33, delete "being".

Column 82, line 44, change "systemas" to --system as--;

line 49, change "systemas" to --system as--.

Column 83, line 14, change "being" to --be--;

line 32, change "prameters" to --parameters--;

line 38, change "coputer" to --computer-- and delete "pl".

UNITED STATES PATENT AND TRADEMARK OFFICE
CERTIFICATE OF CORRECTION

PATENT NO. : 4,827,423

DATED : May 2, 1989

INVENTOR(S) : Thomas B. BEASLEY et al.

Page 13 of 13

It is certified that error appears in the above-identified patent and that said Letters Patent is hereby corrected as shown below:

Column 84, line 8, change "provide" to --provided--.

Signed and Sealed this

Nineteenth Day of March, 1991

Attest:

HARRY F. MANBECK, JR.

*Attesting Officer*

*Commissioner of Patents and Trademarks*